United States Patent [19]
Ryals et al.

[11] Patent Number: 5,431,161
[45] Date of Patent: Jul. 11, 1995

[54] METHOD AND APPARATUS FOR INFORMATION ACQUISTION, PROCESSING, AND DISPLAY WITHIN A MEDICAL CAMERA SYSTEM

[75] Inventors: Carl J. Ryals, Fremont; Stanley H. Wong, Cupertino; Edward M. Goldberg, Sunnyvale; Robert C. Hudson, San Jose, all of Calif.

[73] Assignee: ADAC Laboratories, Milpitas, Calif.

[21] Appl. No.: 48,751

[22] Filed: Apr. 15, 1993

[51] Int. Cl.$^6$ ............................................. A61B 5/05
[52] U.S. Cl. ................................. 128/653.1; 382/131
[58] Field of Search ............... 128/653.1; 364/413.13, 364/413.14, 413.15, 413.22; 382/6, 16, 19

[56] References Cited

U.S. PATENT DOCUMENTS

| | | | |
|---|---|---|---|
| 4,101,961 | 7/1978 | Reiber | 382/6 X |
| 4,125,858 | 11/1978 | Hounsfield et al. | 382/6 X |
| 4,245,646 | 1/1981 | Ionnou et al. | 128/653.1 |
| 4,294,259 | 10/1981 | Picunko et al. | 128/653.1 |
| 4,382,184 | 5/1983 | Wernikoff | 128/653.1 X |
| 4,458,688 | 7/1984 | Von Behren | 364/413.13 X |
| 4,547,892 | 10/1985 | Richey et al. | 128/653.1 X |
| 4,716,904 | 1/1988 | Meno | 128/654 |
| 4,945,478 | 7/1990 | Merickel et al. | 382/6 X |
| 5,046,498 | 9/1991 | Fishman | 128/653.4 |
| 5,065,435 | 11/1991 | Oe | 364/413.13 X |
| 5,072,384 | 12/1991 | Doi et al. | 364/413.13 |
| 5,111,820 | 5/1992 | Axel et al. | 128/653.2 |
| 5,127,408 | 7/1992 | Parsons et al. | 128/634 |
| 5,241,473 | 8/1993 | Ishihara et al. | 364/413.25 |
| 5,255,187 | 10/1993 | Sorensen | 382/6 X |
| 5,255,683 | 10/1993 | Monaghan | 128/662.02 |
| 5,274,549 | 12/1993 | Almasi | 382/6 X |
| 5,287,273 | 2/1994 | Kupfer et al. | 128/653.4 X |
| 5,311,427 | 5/1994 | Ichihara | 304/413.23 |

Primary Examiner—Lee S. Cohen
Assistant Examiner—Brian L. Casler

[57] ABSTRACT

A system for acquisition, processing and display of gated SPECT imaging data for use in diagnosing Coronary Artery Disease (CAD) in nuclear medicine. The present invention provides a physician with two parameters for evaluating CAD: information relating to the distribution of blood flow within the myocardium (perfusion) and information relating to myocardium wall motion (function). One aspect of the present invention provides the physician with a display of functional images representing quantitative information relating to both perfusion and function with respect to selected regions of interest of the subject heart at end-diastole and end-systole segments of the cardiac cycle. The functional display consists of arcs of varied width depending on wall motion and color coded to illustrate degrees of myocardial perfusion for different pie shaped sections of a selected region of interest within a given short axis slice of reconstructed volume data. The present invention also provides a series of display images allowing facilitated access, display, and comparison of the numerous image frames of the heart that may be collected during gated SPECT sessions. The present invention also offers the ability to define and recall parameter files representative of data acquisition and processing parameters and protocol for use in gated SPECT studies. The invention also includes a semi-list processing mode to increase efficiency of data acquisition within a camera computer system.

62 Claims, 22 Drawing Sheets

PROCEDURE ID: GATED SPECT — 300

SPECT PARAMETERS

DEGREES IN ORBIT: _____ 301
IMAGES IN ORBIT: _____ 303
MATRIX SIZE: _____ 305
STARTING LOCATION: _____ 307
ROTATION DIRECTION: _____ 309
ORIENTATION: _____ 311
ORBIT (CIRCULAR): _____ 313
FLOOD CORRECTION: _____ 315
ACQUISITION METHOD: _____ 317

GATED PARAMETERS

NO. OF GATED FRAMES _____ 331
% R-R INTERVAL VARIANCE
MAX % WINDOW _____ 333
MIN % WINDOW _____ 335
R-R INTERVAL FIXED _____ 337
R-R INTERVAL VARY _____ 339
NO. EXCLUDE AFTER VARIANCE _____ 341
TIME PER ECT AZIMUTH OR TOTAL BEATS _____ 343

ISOTOPE ID: _____ 351
PATIENT ID: _____ 353
VIEW ID: _____ 355

| PROCESSING |
| --- |
| 357 |

TIME _____ AVG R-R _____
FRAME NO. _____ GATED FRAMES _____
MAX FRAME _____ MAX FRAMES _____
COUNTS/SEC _____
BEATS _____

[Help]  [Quit] [icons] [FILES] [icon] [icon] DEFAULTS  [Proceed] — 563

— 535                                              — 561

PROCESSING

METHOD: ○ BOTH — 510

SAVE: ○ gSPECT FILES — 511

RECONSTRUCTION PARAMETERS

SLICE THICKNESS: ○ 1 — 512

ORIENTATION: ○ ACC — 514

DECAY CORRECT: ○ ON — 516

↙ 5

SAVE OBJECTS — 540

☑ RAW TRANSVERSE
☑ REORIENTED TRANSVERSE/SHORT AXIS
☑ CORONAL/HORIZONTAL LONG AXIS
☑ SAGITTAL/VERTICAL LONG AXIS

FILTER PARAMETERS

WINDOW: ○ BUTTERWORTH — 520

Y - AXIS FILTER: ○ SMOOTHING — 525

AXIS OF ROTATION: 0.00 — 526

FREQUENCY CUTOFF: 0.35 — 527

ORDER: 5 — 528

RECONSTRUCTION LIMITS

START LIMIT: 32 ⎱ — 529
END LIMIT: 45 ⎰

SEGMENTS TO PROCESS — 530

☑ GATED SEGMENT 1    ☑ GATED SEGMENT 9
☑ GATED SEGMENT 2    ☑ GATED SEGMENT 10
☑ GATED SEGMENT 3    ☑ GATED SEGMENT 11
☑ GATED SEGMENT 4    ☑ GATED SEGMENT 12
☑ GATED SEGMENT 5    ☑ GATED SEGMENT 13
☑ GATED SEGMENT 6    ☑ GATED SEGMENT 14
☑ GATED SEGMENT 7    ☑ GATED SEGMENT 15
☑ GATED SEGMENT 8    ☑ GATED SEGMENT 16

FIG. 12

METHOD AND APPARATUS FOR INFORMATION ACQUISTION, PROCESSING, AND DISPLAY WITHIN A MEDICAL CAMERA SYSTEM

BACKGROUND OF THE INVENTION

1. Field of the Invention

The present invention relates to the field of nuclear medicine camera systems. More specifically, the present invention relates to the field of nuclear medicine camera systems utilizing gated SPECT acquisition techniques, 2. Prior Art In an attempt to more accurately diagnose Coronary Artery Disease (CAD) and generally diseases of the heart, specialized nuclear medicine camera systems have been developed to provide physicians with vital information regarding the structure of the heart and myocardial wall tissue. The images of the heart structure provided by these non-intrusive nuclear medicine camera systems illustrate tissue and structure that would not be otherwise visible without the application of nuclear medicine or other non-intrusive method. Gamma cameras of the Anger type are well known cameras in the field of nuclear medicine. These cameras receive energy emissions from a radio-pharmaceutical that is introduced into a patient and concentrates or localizes within the organ or tissue of interest for imaging. Such cameras are used extensively in nuclear medicine as radiation detectors for establishing the distribution of the radio-pharmaceutical within the organ or tissue of interest. Such a camera is described in detail in U.S. Pat. No. 3,011,057 issued to Anger in which a typical gamma camera apparatus is disclosed for collecting information after introduction of radionuclides via inhalation, injection or ingestion.

Single Photon Emission Computerized Tomography (SPECT) is a type of nuclear camera imaging system wherein the radiation detector of the camera system is rotated about an organ or tissue (referred as an object of interest) and images of the object of interest are recorded at discrete angles of rotation. By projecting back each image of the object at these different rotation angles, a total image or reconstructed volume can be generated and images may be observed at different slices within the object volume itself. In other words, three dimensional image information can be generated by SPECT camera systems of the object of interest. Typically the camera detector rotates 180 degrees or full 360 degrees around the object (patient) during the image acquisition phase of the SPECT camera system. Once the image data is collected by the camera system, it is processed by a computer system where the tomography is performed and the images may be generated qualitatively and studied on a computer display screen. Such SPECT camera systems are well known in the art of nuclear medicine.

With respect to prior art SPECT camera systems used in non-gated cardiac perfusion studies, heart tissue is studied for infarct areas and ischemic areas by examining the heart under two different conditions, a stress condition and a rest condition. Perfusion refers to the blood flow to the heart in the areas of interest. The radionuclide introduced to the heart will follow the blood flow and thus perfusion is determined by monitoring the resultant radiation from the radionuclide. An infarct area is an area of the heart that is not functional and may be composed of dead tissue. This area may not take up much if not any of the introduced radio-pharmaceutical. An ischemic area of the heart is an area that may perhaps function normally during rest conditions, but will not function normally during cardiac stress conditions. In order to detect an ischemic area, non-gated SPECT systems must collect image data at cardiac rest and stress conditions, requiting two sessions. Therefore, according to the two conditions under study as described above, the ischemic area will be detected by comparing the images of the heart during the stress condition and the rest condition. In this prior art system, SPECT camera systems are used to examine the heart after the heart is subjected to a stress condition, typically by having the patient run a treadmill. The heart imaging session of the prior art camera systems takes approximately 30 minutes. Next, the patient is allowed to rest for at least four hours and a new imaging session is performed on the heart during a rest condition. The physician then compares the results of the imaging at rest and at stress. An ischemic area may show up as a myocardial defect on images of the heart taken during stress conditions but may show up normally on images of the heart taken during rest conditions. An infarct area should show up as a defect in the heart at both rest and stress conditions.

The above prior art non-gated SPECT perfusion method for determining CAD, such as infarct areas and ischemic areas, is not the most advantageous system. This is the case because two imaging sessions must be performed in order to adequately detect and diagnosis cardiac disease. For instance, a cardiac rest session and a cardiac stress session are required in the prior art that consume at minimum 30 minutes per session. Further, the patient must be allowed to rest for at least four hours in between cardiac stress/rest sessions. Taking in to account preparation and analysis time, the entire non-gated SPECT imaging session could consume well over six hours in total. Therefore, it would be advantageous to provide a system capable of accurately detecting infarct areas and ischemic areas of the heart without the need for two separate scan sessions performed in conjunction and without the intermediary rest period in between. The present invention offers such advantageous capability.

Further, prior art camera systems employing SPECT imaging, in non-gated perfusion studies, do not offer an advantageous method for detecting false positive determinations of an infarct area or an ischemic area of the heart. This is the case because other effects, such as attenuation of the radiation signal or statistical variations of the radiation distribution may cream artifacts within the image system that mimic diseased areas of an image. It is difficult to accurately and efficiently determine whether particular regions of images from these non-gated SPECT systems are actually an infarct or ischemic area or rather simply an artifact as a result of one of the above effects. For example, a resultant image from a male heart often contains artifacts (false positives) in the inferior heart area as a result of radiation attenuation of the diaphragm, which varies due to the diaphragm size. Also, a resultant image from a female heart often contains artifacts (false positives) in the anterior lateral to anterior septal areas of the heart as a result of radiation attenuation from the breasts, which may vary due to breast size. In these cases for both males and females, it is desirable to be able to detect and correct for these false positives. It would be advantageous to provide an efficient system for quantitatively testing false positive ischemic and infarct areas of the heart. The present invention offers such advantageous functionality.

Gated SPECT camera systems are similar in nature to the non-gated SPECT camera systems described above, however, the imaging of the object is gated at discrete intervals of time during the cardiac cycle for each discrete angle of rotation of the camera detector. Gated SPECT increases the sensitivity and specificity of diagnosis as compared to non-gated SPECT procedures because gated SPECT allows the observation of both characteristics of perfusion and function within cardiac physiology. For cardiac gated SPECT camera systems, the timing intervals are synchronized to different segments of the cardiac cycle. The heartbeat cycle contains locations indicating a systolic phase of the heart where the heart tissue is contracting to pump blood and a diastolic phase of the heart where the heart is expanding and filling with blood. By synchronizing the collection of imaging information from the heart (the object of interest in cardiac studies) at the diastolic and systolic phases of the cardiac cycle, the gated SPECT camera system can provide physicians with images of the heart during both contraction and expansion. This information is utilized in diagnosing heart disease, such as CAD. Gated SPECT camera systems can be utilized to image the heart at any timing segment within the heartbeat cycle (cardiac cycle). Typically in gated SPECT techniques, the image of the heart at the end of the diastolic phase (end-diastole) is recorded and studied and the image of the heart at the end of the systolic phase (end-systole) is recorded and studied.

According to gated SPECT studies, if a heart region is detected with a certain count density in the myocardium at maximum expansion (end-diastole) and this region does not show much increased count density at minimum expansion (end-systole), then the myocardium in the location of the defect may be ischemic or artifactual. If the count density remains constant over the time segments then the defect may represent an infarct or dead tissue. It would be advantageous to utilize the above principles in conjunction with wall movement data in a nuclear camera imaging system to provide quantitative information regarding the myocardium which can be used for diagnosis. The present invention offers such capability by providing specialized quantitative displays of the gated SPECT image data.

Prior art systems of gated SPECT nuclear camera systems have focused primarily on qualitative studies over quantitative studies. To this extent, images generated at end-diastole and end-systole have been presented to the diagnosing physician without any meaningful quantitative analysis of the structures or movements of structures of the heart. This leaves determination and diagnosis of possible diseased areas of the heart (i.e. infarct or ischemic areas) to approximate and non quantitatively based judgments on the part of the physician. It would be advantageous to provide a gated SPECT nuclear camera imaging system that offered quantitative analysis and measurement display of the heart region or regions under review. This quantitative data could then more effectively aid a physician in diagnosing areas of CAD and accurately reproduce such findings. The present invention offers such advantageous quantitative information analysis and display capability.

Other prior art systems determined ejection fractions as an alternate avenue for CAD diagnosis and employ gated SPECT camera systems qualitatively to determine the ejection fraction. The ejection fraction is the percent of total blood in the heart cavity that is actually ejected from the heart during contraction and expansion. Gated SPECT techniques are utilized to image the heart during contraction (systole) and during expansion (diastole) to determine the heart volumes at these periods which can be used in diagnosing heart disease to determine the ejection fraction. The ejection fraction is determined as a ratio between the difference of the volume of the heart at diastole and systole over the volume of the heart at diastole. A low ejection fraction may indicate an infarct or ischemic area.

The above prior art methods of determining the ejection fraction are limited because the determination method of the systolic and diastolic volumes is not accurate and the determination more often than not is the result of approximation and qualitative judgment based on qualitative information presented to the physician. Since the volume determinations are not quantitative, the ejection ratios determined are not quantitative and not readily reproduced lending various contradictory diagnosis for a given condition. Aside from the qualitative nature of the image data, physical limitations in the camera resolutions and partial volume effects severely degrade the accuracy and reproducibility of the determination of these two volumes. It would be advantageous to provide quantitative method for determining cardiac disease using gated SPECT techniques over the above prior art design. The present invention provides such capability.

Additionally, prior art nuclear camera systems collect data from the camera detector using two data parsing passes. The first parsing pass examines each byte or word of data that is detected by the camera detector and is used to construct a temporary histogram for a particular heart beat, this is called a beat histogram. After the first parsing processing is complete, a second processes sums the beat histogram data with the overall or total sum histogram that represents histogram data for all imaged beats for a given projection angle and for a given gated segment. If the newly collected beat histogram represents data from a heartbeat that is to be rejected, then the beat histogram data will be erased and therefore ignored. This prior art process requires a great deal of time and processing power because, essentially, the input data from the detector must be completely parsed twice before it is incorporated into the summation histogram. Further, if a particular heartbeat is to be ignored, it is wasteful of processing power and inefficient to construct the beat histogram. Therefore, what is needed is a method of determining bad beats without inefficient construction of the beat histogram. Further, what is needed is a way to implement the data acquisition processing of the nuclear camera system that can eliminate the double parsing required if data from a bad heartbeat is detected and avoid constructing a beat histogram that is never used. The present invention provides such capability. Further, the present invention also offers the capability, upon detection of a bad current heartbeat, of skipping the data representative of a just previously imaged heart beat.

Accordingly, it is an object of the present invention to provide a nuclear medicine imaging system for aiding in the diagnosis of cardiac disease using gated SPECT techniques. It is an object of the present invention to provide a nuclear medicine imaging system for aiding in the diagnosis of cardiac disease without requiring both a stress imaging session and a rest imaging session in conjunction. Further, it is an object of the present invention to provide a gated SPECT imaging system wherein wall motion and wall perfusion can be quantitatively computed and rendered with respect to various images of the heart at various gated segments of the cardiac cycle. It is also an object of the present invention to provide a nuclear imaging camera system capable of effectively and efficiently detecting false positives for infarct and ischemic areas of the heart. It is yet another object of the present invention to provide a gated SPECT system for providing a functional image that simultaneously displays both wall movement and wall thickening information. It is also an object of the present invention to provide an effective display system allowing efficient location, display and comparison of image frames of the multitude of image frames that are made available from the spatial slices and temporal segments of reconstructed volumes resultant from a gated SPECT study. It is an object of the present invention to provide an efficient data acquisition procedure of a camera system that has the ability to skip bad beat data events without constructing a beat histogram. These and various other objects not specifically mentioned above will become evident upon further review of the discussions of the present invention to follow.

SUMMARY OF THE INVENTION

The present invention includes embodiments covering an apparatus and method for acquisition, processing and display of image data from a nuclear camera imaging system. The preferred embodiment of the present invention utilizes image data originating from a gated SPECT (Single Photon Emission Computerized Tomography) nuclear camera system. The preferred embodiment of the present invention includes specialized display screens and display formats optimized to display quantitative information regarding two parameters of cardiac physiology: perfusion and function within the same display. This specially optimized screen allows efficient detection of an infarct area as well as an ischemic area within the cardiac tissue under review. This element of the preferred embodiment of the present invention provides a physician, or determining medical technician, a method and means for analyzing the acquired image data from the nuclear camera system in the diagnosis of coronary artery disease (CAD) by creating functional images representing quantitatively computed values for both perfusion and function.

Embodiments of the present invention also include a system for programming, saving and recalling a number of default parameters and protocol that control the data acquisition and processing phases of the imaging procedure. Using such predefined default parameters for processing, the imaging system of the present invention can be effectively and efficiently utilized without time consuming parameter adjustments that might otherwise be required for entry. Further embodiments of the present invention include a system and display format for efficient and comprehensive display and comparison of images representing slices of reconstructed volumes that are reconstructed from images acquired by the camera system. This display format allows a number of different images to be easily displayed, referenced, compared, and recalled within a high resolution color computer display screen using user interface mechanisms.

More specifically, embodiments of the present invention include an apparatus for presenting quantitative image information used for diagnosing heart disease, the quantitative image information based on data obtained using gated SPECT techniques, the apparatus comprising: means for displaying a first image of a myocardial structure during diastolic phase of a cardiac cycle; means for displaying a second image of the myocardial structure during systolic phase of a cardiac cycle; means for selecting a region of interest of the first image and also for selecting a region of interest of the second image; means for computing perfusion ratios and wall movement factors for individual sections of the myocardial structure defined by the regions of interest; and means for displaying a functional ring representative of the myocardial structure, the functional ring comprising representations of both the perfusion ratios and the wall movement factors of the individual sections of the myocardial structure.

Embodiments of the present invention include the above wherein the region of interest of the first image and the region of interest of the second image are each divided into a plurality of individual sections and wherein a section pair comprises sections of each region of interest that correspond to a same portion of the myocardial structure and wherein the means for displaying a functional ring representative of the myocardial structure comprises: means for displaying a plurality of arc sections comprising the functional display ring, wherein each arc section corresponding to an individual section pair; means for coloring each arc section depending on a perfusion ratio for the each arc section; and means for varying radial width of the each arc section depending on a wall movement factor for the each arc section.

Further embodiments of the present invention include a computer implemented method for displaying information on a display screen used in diagnosing heart disease, the information obtained using gated SPECT imaging techniques and tomographic reconstruction procedures, the method comprising the computer implemented steps of: receiving a plurality of computed ratios representing myocardial perfusion for a selected region of myocardium; receiving a plurality of computed wall movement factors representing myocardial wall movement for the selected region of myocardium; rendering a functional ring on the display screen comprising a plurality of arc sections, the plurality of arc sections presenting representations of both the computed perfusion ratios and the computed wall movement factors.

Embodiments of the present invention include the above and further wherein the step of rendering a functional ring comprises the steps of: displaying each of the plurality of arc sections with an individual color representation based on an individual perfusion ratio of the plurality of myocardial perfusion ratios; and displaying each of the plurality of arc sections with an individual arc section width based on an individual wall movement factor of the plurality of computed wall movement factors.

Additional embodiments of the present invention include in a nuclear camera system having an acquisition processor, a memory unit, and at least one detector unit for detecting image events, a computer implemented semi-list acquisition method for parsing the image events to create, the method comprising the computer implemented steps of: receiving individual data event words for an entire R—R interval to form a current data event word set; storing the data event words in list form for an entire R—R interval in a buffer of the memory unit; and indicating, within unique locations with the current data event set, a start address for a subsequent data event word set and a count number representative of the duration of the R—R interval of the current data event word set, monitoring the unique locations of the start address and the counter number until one of the locations contains a non zero value; and binning the data event words for the entire R—R interval directly into a summation histogram.

BRIEF DESCRIPTION OF THE DRAWINGS

FIG. 3 illustrates the parameter selection screen of the data acquisition system 20 of the present invention.

FIG. 5 is illustrates the reconstruction parameter screen of the present invention.

FIG. 12 is an illustration of the images display screen of the display screen processing of the present invention displaying separate series of image frames for short axis, vertical long axis and horizontal long axis datasets.

DETAILED DESCRIPTION OF THE INVENTION

Figure 1:
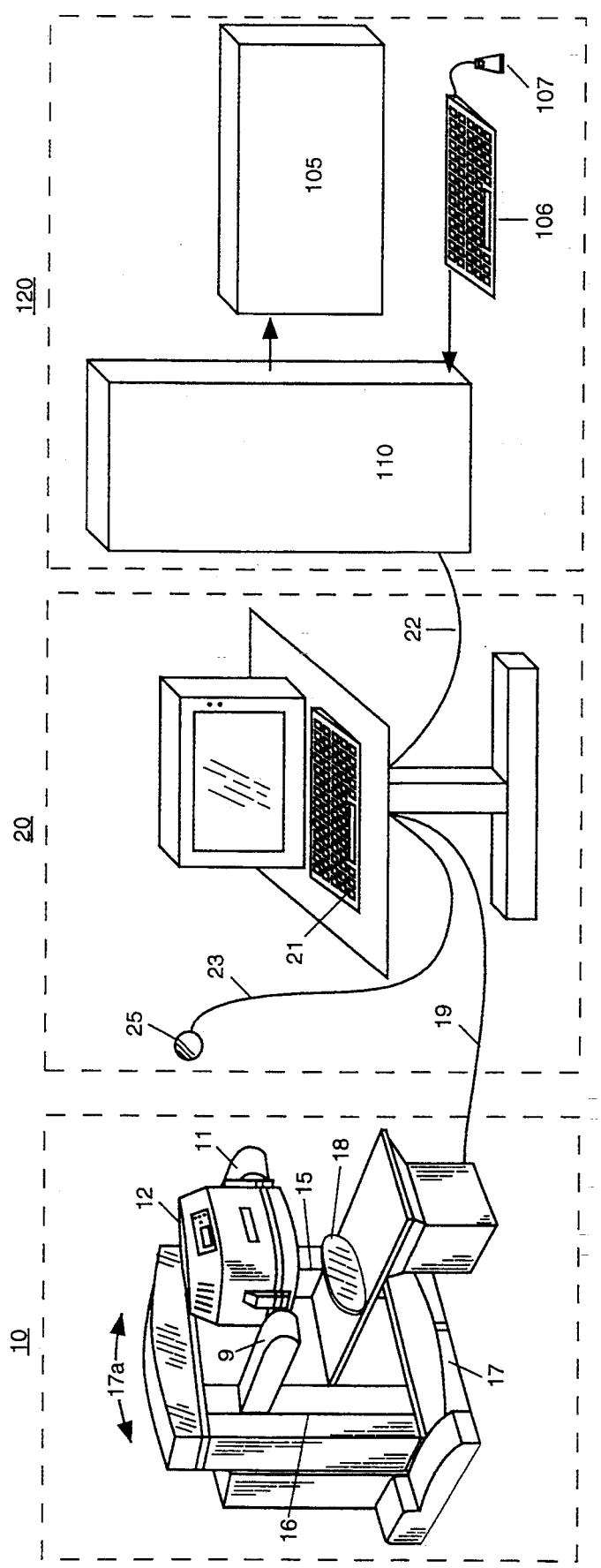
FIG. 1 illustrates three main systems of the present invention, the nuclear camera 10, the data acquisition computer 20, and the image data processing (reconstruction) and display system 120.

In the following detailed description of the present invention numerous specific details are set forth in order to provide a thorough understanding of the present invention. However, it will be obvious to one skilled in the art that the present invention may be practiced without these specific details. In other instances well known methods, components, processes, and systems have not been described in detail as not to unnecessarily obscure aspects of the present invention. Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. Unless specifically stated otherwise as apparent from the following discussions, it is appreciated that throughout the present invention, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Introduction

The following detailed discussion is segmented into five major sections following this introduction. Section I covers the overall components of the individual systems of the present invention including FIGS. 1–2, section II covers the image acquisition system and procedures including FIGS. 3–4, section III covers the processing procedures including FIGS. 5–8 and section IV covers the image display procedures including FIGS. 9–16. The data acquisition system of section II is primarily composed of camera system and computer and gathers raw gSPECT image data. A computer processing system of section III then takes the raw gSPECT image data and reconstructs the data into three individual datasets each composed of a series of image frames representative of reconstructed volumes of the raw gSPECT image data. Section IV covers an image display system that allows visualization of these image frames and also allows quantitative and qualitative analysis of the image data including a segmented functional display illustrating perfusion ratios and wall movement for a selected section of myocardium. The image display system of section IV is used as a tool for physicians in diagnosing cardiac disease. Section V covers aspects of the present invention that are implemented within camera system 10 of the present invention to improve throughput and processing efficiency of the image data received from the detector 12 and passed to the data acquisition computer 20 by implementing a semi-list mode acquisition procedure. The following introduction describes major aspects of the present invention.

A basic premise of the present invention is to utilize the image display processing (section IV) to provide meaningful quantitative measurement and display of two valuable pieces of information that are collected and available using gated SPECT imaging: wall motion and wall perfusion of the myocardium to enable accurate diagnosis of CAD. Gated SPECT camera systems collect images from a patent, in a single imaging session, that contain information of the heart (1) at rest for wall motion and (2) at stress for blood perfusion. For instance, gated SPECT camera systems image the heart during an interval where the patient is still which is defined as a rest condition. Even if the heart was exercised a few minutes prior to imaging, the heart enters and remains in the rest condition by the time the imaging process or session begins. The gated SPECT system collects images of the heart at different time periods (segments) of the cardiac cycle as the heart is in motion and this information is used by the present invention in part to compute and display wall motion information. Therefore, wall motion information represents the heart during the rest condition. However, the radionuclide used for imaging is introduced into the blood during a stress condition and distributes in the heart at stress. Throughout the gated SPECT imaging session, the radionuclide will remain in this stress distribution until metabolized from the heart much later. Therefore, although the heart enters the rest condition during imaging (as discussed above) the radionuclide distribution remains in the same distribution as introduced in the stress condition.

The present invention advantageously utilizes the above rest/stress image data to display, quantitatively on a single functional display ring, images of the heart at stress (perfusion) and images of the heart at rest (wall motion) for diagnosis using only one imaging session. To this extent, a displayed structure of the myocardium on a display screen is segmented into regional areas by a computer and the counts in the regional areas can be measured at end-diastole (ED) and end-systole (ES) segments of the cardiac cycle. The total counts within these regional areas (sections) remain approximately the same at ED and ES, however, the average maximum pixel count density increases at ES for a healthy heart as compared to the similar regional area for ED. This is because the myocardium is at contraction during end-systole and more of the radionuclide is concentrated per sectional area during end-systole as compared to end-diastole when the heart is expanded and filling with blood.

One aspect of the present invention creates specialized functional display rings on a color computer display screen to quantitatively represent perfusion and function in conjunction with respect to each corresponding sectional area for ED and ES image segments. According to a method of the present invention, regions of interest are selected with respect to two images, an end-diastole image and its associated end-systole image which are both displayed on the computer screen at the same time. The user applies a separate circular region of interest (ROI) which is divided into 8 (or 16) pie shaped subregions, or sections on each image of the ES/ED pair. The center and diameter of the region of interest (and thus the area of any particular section) are user adjustable with respect to associated images of the myocardium at end-diastole and end-systole. The aspects of the functional image of the present invention that relate to perfusion are based on dividing the maximum pixel value (i.e., the count value of the pixel having the maximum count) at ED by the maximum pixel value at end-diastole. If the segmented myocardium is normal then the ratio should be greater then 1.0 as discussed above (i.e., more dense at end-systole). With respect to wall movement, the maximum pixel values at ED and ES are used to compute a center of mass for each section by dividing the total number of pixels in the section by the total counts in the section for all pixels. A radial distance is then computed from the center of mass of the section to the center of the region of interest for ED and ES. A displacement factor is computed by the present invention which represents the change in radial distances between the ED section and the associated ES section. The computed width of the functional display section may be negative or positive depending on displacement in the corresponding ROI. The above must be done by the present invention for each section of the corresponding ROIs for ED and ES.

Specifically, with regard to the display format, the present invention provides a separate functional display arc section for each section pair (ES/ED) and displays the ratio for each section pair by color coding the arc section and spatially locates the arc within the ring in the functional display ring according to the spatial location for the particular section pair. The width of each arc is determined by the wall movement value for each section pair. The different colors currently utilized by the present invention for perfusion color coding are black, purple, blue, green, yellow, orange, red, and white to represent the range from just less than 1.0 and just greater than 2.0 in 0.1 increments. However, any color combination or ratio range capable of imparting ratio information will suffice within the scope and spirit of the present invention including different shades of the same color for different ratio values. The color coded arcs are arranged and applied to form a ring representing the myocardium for a given and selected ROI of a given tomographic slice, usually of the short axis dataset which illustrates a circular cross section of the ventricle. Display information is added to the ring to indicate wall motion information (function) between ED and ES segments. This displacement factor is applied to adjust the width of each color coded arc based on the displacement factor for a given ES/ED section pair. The result is a functional ring color coded to represent wall thickening and varying arc widths to represent wall motion for associated section pairs of a given pair of ED and ES ROIs; all within a single display. This process is applied on a frame by frame basis to a set of frames displayed on the computer screen. The systems and procedures of the present invention will now be described in more depth.

SECTION I

Overall Component System of the Present Invention

FIG. 1 illustrates the major components of the nuclear camera image acquisition, processing and display system of the present invention. The present invention includes either a single head (detector) camera or a dual head camera 10 (as shown in FIG. 1 a single head camera is present). The preferred embodiment of the present invention utilizes a Cirrus TM Nuclear Imaging Camera system available from ADAC Laboratories of Milpitas, Calif. The Cirrus TM Camera system is a SPECT camera ideal for cardiac studies and implements gated SPECT imaging techniques. Embodiments of the present invention utilizing dual head camera designs are implemented with the Dual Head Genesys TM Nuclear Imaging system and the Genesys Vertex TM Camera system also available from ADAC Laboratories of Milpitas, Calif. The Genesys TM camera system also supports gated SPECT acquisition. Two arms 11 and 9 mounted on vertical tracks 16 and 15 form a gantry structure that can move the detector head 12 in various projection angles to accomplish the required 180 and 360 degree movements of the detector 12 used in gated SPECT studies. Pivot structure 17 allows the camera detector 12 and gantry structure to pivot clockwise or counterclockwise. The camera system 10 of the present invention includes a detector head 12 comprising a number of well known radiation detection components of the Anger camera type including a photomultiplier array, a collimator, a scintillating crystal and a digital pixel output. The camera system 10, in a well known fashion, images the patient to provide digital image data which is binned according to particular discrete angles of rotation in which the detector 12 traverses about the patient and binned according to particular segments within the cardiac R—R interval (defined below). For each angle of rotation, several segments may be collected of the cardiac cycle. Particular (x,y) coordinate positions within the imaging detector of the camera system are called pixels and the number of scintillations detected by each pixel location is represented by a count value for that pixel. The resulting digital image data from the camera system 10 is binned according to the particular discrete angle of rotation in which the detector was situated when the image was acquired. Also binned is the gated segment within the R—R interval in which the data was acquired in gated SPECT studies. Particular coordinate positions within the imaging detector of the camera system are called pixels. Each pixel contains a count value representing the number of radiation emissions detected at that location of the detector 12. The pixel matrix of (x, y) locations is referred to herein as a histogram of scintillations at these coordinate locations. It is understood that a histogram represents a raw image. For example, a typical detector 12 may have resolution of (64×64) pixels or (128×128) pixels available for imaging for modes of the invention and is capable of imaging at approximately (1000×1000) resolution maximum. Within each pixel location reported by the camera system 10, is a scintillation count number for that pixel.

The camera system 10 is coupled to a data acquisition computer system 20, which in the present invention is implemented using a general purpose computer system having high speed communications ports for input and output coupled to a two way data transmission line 19 which couples the camera system 10 to the computer system 20. The computer system 20 communicates data acquisition parameters (also called data acquisition protocols) selected by a user to the camera system 10 to initiate a particular type of gated SPECT study within the camera system 10. The imaging data from the camera system 10 is then transferred over line 19 to the communications device of the system 20 and such raw gated SPECT image data is then forwarded to a post acquisition processing computer system 120. The data acquisition system 20 also comprises a keyboard entry device 21 for user interface to allow selection and modification of predefined data acquisition parameters which control the imaging processes of the camera system 10. Also coupled to the data acquisition system 20 is a standard color display monitor 20 for display of parameter information and relevant information regarding the particular gated SPECT study underway (such as imaging status communicated from the camera system 10 during an imaging session).

A cardiac electrode and signal amplification unit 25 is also coupled to the data acquisition computer system 20. This unit 25 is specially adapted to couple with a patient's chest near the heart to receive the heartbeat electrical signal. This electrode unit 25 is composed of well known heartbeat detection and amplification techniques and components and any of several well known devices can be utilized within the scope of the present invention. In order to perform gated SPECT analysis on the heart, the heartbeat pulse or electrical wave must be studied for each patient, as each heart is different. The heartbeat wave is examined to determine the points within the cycle where the well known R wave is encountered. The time interval between successive R waves is measured by the present invention to determine the R—R interval. These points and timing intervals between these points will be used to gate the imaging process of the camera system 10 during the cardiac cycle and particularly at the end-diastole and end-systole interval segments. The preferred embodiment of the present invention automatically, under control the system 20, collects five sample heartbeat waves once the detector 25 is located on the subject patient in order to determine the average R—R period. This information is fed to the computer system 20 and then sent to the camera system 10, however such information could also be detected and determined directly by the computer system 10 once queued to do so by the acquisition computer system 20 under user control. For a particular projection angle, the system 10 then directs the acquired imaging counts to the first segment bin, and upon each successive time interval the image data is directed to a new gated bin. When the R wave is detected once more the first bin receives the image data again and the process continues through each other segment and associated bin until a new projection angle is encountered. The electrode 25 also is used by the camera system 10 in order to detect the start of a cardiac cycle and gate the camera imaging system appropriately depending on the number of selected segments of the R—R interval for collection.

As discussed above, the data acquisition phase of the present invention imaging system is composed of camera system 10 and computer system 20. Referring still to FIG. 1, the image data is sent from the camera system 10 over line 19 to acquisition system 20 and then over line 22 to the image processing system 120. This system 120 is responsible to displaying and quantifying certain data acquired by system 10 and system 20. Specifically, according to the present invention, this system 120 will process and uniquely display quantitative information regarding blood flow within the myocardium (perfusion) and wall motion of the myocardium (function) as a result of the gated SPECT data acquired.

Post Data Acquisition Processor System 120

The Post Data Acquisition Processor System 120 acquires the raw gated SPECT image data generated from the camera system 10 and using user configurable procedures, reconstructs (performs tomography or back projects) the data to provide a reconstructed volume and from the volume generates specialized images of the myocardium for diagnosis, including generating and displaying the functional images as described above. The generated images or frames of the myocardium represent different slices of the reconstructed volume heart at variable thickness in a short axis dimension, a vertical dimension and a horizontal dimension (all three are user configurable) for a number of gated time segments. Therefore, complete three dimensional information can be displayed by display 105 in a two dimensional manner in a variety of formats and orientations by the present invention including a display providing quantitative information regarding both wall thickening (perfusion) and wall motion (function) of the myocardium under study.

Figure 2:
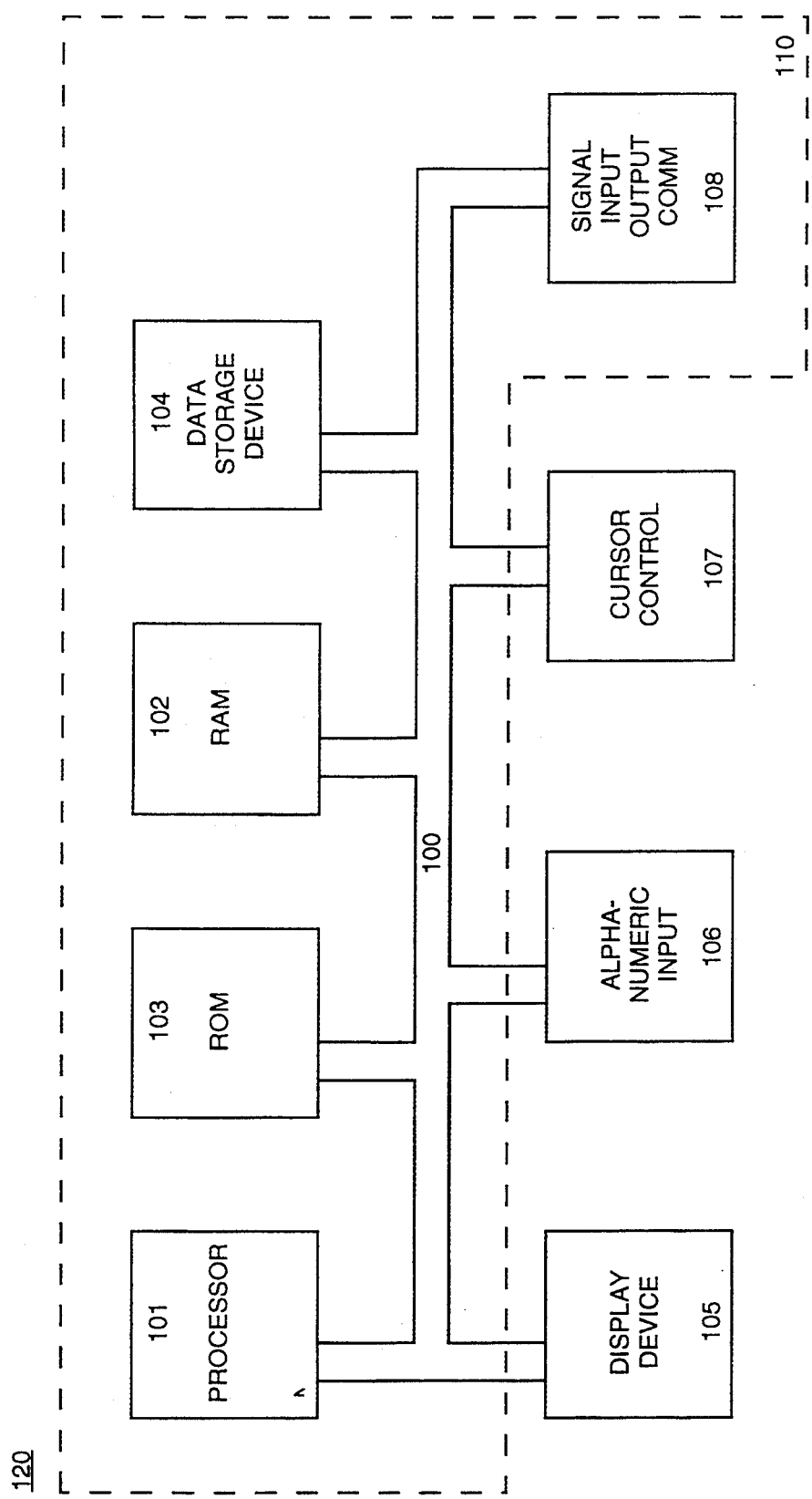
FIG. 2 illustrates a block diagram of elements of the post data acquisition processing (reconstruction) and display system 120 of the present invention.

The computer system 120, illustrated in FIG. 2, is a SPARC system available from Sun Microsystems of California as modified with a Pegasys hardware backplane available from ADAC Laboratories, however any number of similar computer systems having the requite processing power and display capabilities will suffice within the scope of the present invention. Generally, the computer system 120 comprises a bus 100 for communicating information, a central processor 101 coupled with the bus for processing information (such as image data and acquired counts) and command instructions, a random access memory 102 coupled with the bus 100 for storing information and instructions for the central processor 101, a read only memory 103 coupled with the bus 100 for storing static information and command instructions for the processor 101, a data storage device 104 such as a magnetic disk or optical and disk drive coupled with the bus 100 for storing information (such as image data both raw gated SPECT and reconstructed data sets.) and command instructions, and a display device 105 coupled to the bus 100 for displaying information to the computer user. There is also an alphanumeric input device 106 including alphanumeric and function keys coupled to the bus 100 for communicating information and command selections to the central processor 101, a cursor control device 107 coupled to the bus for communicating user input information and command selections to the central processor 101 based on hand movement, and an input and output device 108 coupled to the bus 100 for communicating information to and from the computer system 120. The signal generation device 108 includes, as an input device, a high speed communication port configured to receive image data acquired by the nuclear camera system 10 and fed over line 22.

The display device 105 utilized with the computer system and the present invention may be a liquid crystal device, cathode ray tube, or other display device suitable for creating graphic images and alphanumeric characters recognizable to the user. The display unit 105 of the preferred embodiment of the present invention is a high resolution color monitor. The cursor control device 107 allows the computer user to dynamically signal the two dimensional movement of a visible symbol or cursor 5 (pointer) on a display screen of the display device 105. Many implementations of the cursor control device are known in the art including a trackball, mouse, joystick or special keys on the alphanumeric input device 105 capable of signaling movement of a given direction or manner of displacement. It is to be appreciated that the cursor means 107 also may be directed and/or activated via input from the keyboard using special keys and key sequence commands. In the discussions regarding cursor movement and/or activation within the preferred embodiment, it is to be assumed that the input cursor directing device may consist any of those described above and specifically is not limited to the mouse cursor device. It is appreciated that the computer chassis 110 may include the following components of the present invention: the processor 101, the ROM 103, the RAM 102, the data storage device 104, and the signal input and output communication device 108 and optionally a hard copy printing device.

SECTION II

Data Acquisition Procedures of the Present Invention

The data acquisition system 20 (FIG. 1) allows a user via keyboard control to select and/or create a predefined set of parameters (or protocol) for direction of a gated SPECT imaging session by the camera system 10. FIG. 3 illustrates a parameter interface screen and configurable parameters of the present invention for data acquisition that are selected and displayed on screen by the user via keyboard 21. The following are descriptions of the parameters configurable by the present invention data acquisition system 20. It is appreciated that once set, the following parameters can be saved and referenced in a computer file for subsequent recall. This parameter or protocol file can be then recalled and utilized for a particular gated SPECT study thus eliminating the need to enter again the parameters for similar or identical gated SPECT studies. The parameter file name as shown in FIG. 3 is "GATED SPECT" and is indicated at 300. It is appreciated that the computer system 20, once instructed by the user, will relay the parameters set by the user to the camera system 10 in order to initialize and begin a particular gated SPECT study. The initiation is done by selection of menu 357.

Refer to FIG. 3. The present invention data acquisition system 20 allows the user to select the total orbit of the camera detector 12 for the gated SPECT study or for a regular SPECT study at 180 degrees or full circle 360 degrees. If 360 degrees total orbit are selected, the maximum number of projection positions available are 128 or 2.81 degrees per projection and the minimum number of projection positions is 32 representing 11.25 degrees per projection. Selection for number if projection angles during the total orbit (i.e., number of ECT frames to gather during the total orbit is entered via 303 and is either 64, or 128. The maximum pixel matrix size for the detector 12 imaging surface is 128×128 pixels and entry is by selection 305. The starting projection angle of the detector 12 is selected as any angle within 360 degrees at selection 307. The direction of rotation for the detector 12, either clockwise or counter clockwise may be selected by a parameter of the present invention at selection 309. The patient orientation may also be selected by the computer 20 as: feet in face up, feet in face down, head in face up, or head in face down at selection 311. The patient orientation may also be specified by a selection for supine or prone at 311. It is appreciated that the present invention allows selection of the total time per ECT projection by allowing the user to set the total time per projection angle or the number of beats per projection angle at 343.

The duration of time spent at each rotation angle is held constant by the present invention by time normalization of the good beats. According to the normalization procedure, the total time of good beats imaged at each rotation angle is held constant and the imaging time for each of the gated segments is held constant. According to this normalization procedure, count numbers, based on count number and averages, are added to deficient imaging bins in order to increase the count number for normalization purposes on a proportionate basis. The present invention allows for parameter set up for the particular orbit utilized by the camera system, i.e., if selected circular then the user must optimize the collimator to patient distance; which is selected at input 313. Selection is also provided to allow the patient to collimator distance to be automatically computed and controlled. The computer system 20 also allows for flood correction parameter configuration which allows the user to select the flood correction matrix for correcting nonuniformities associated with the scintillation detectors 12 at input 315. The correction will be applied on the post data acquisition system 120 as the image data for each projection angle is stored within system 120.

Refer to FIG. 3. The present invention allows for selection of either continuous imaging or step and shoot data acquisition via an input called acquisition method at 317. Both methods are well known in the art. The present invention allows for selection of either continuous imaging or step and shoot data acquisition via an input called acquisition method at 317. Under continuous acquisition, the camera system 10 will acquire image data during the translation phase from one projection angle to the next to increase acquisition of image data and improve image quality. The data will be acquired in frame mode, but a frame of data (a projection) will include acquired data at the determined angle plus the acquired data during the movement of the detector to the next location. In order for each projection to contain the stone amount of acquisition time, the last frame acquired must include data from the static location and the data during the translation period to the next static location. If during the translation an R—R interval is detected that is outside an allowable range (see below), this beat will be rejected by the present invention but the acquisition time will not be extended. The translation will continue to the next angle for imaging. The time normalization process of the present invention will compensate for the difference in total time acquired at the end of the imaging session. During step and shoot SPECT acquisition, the camera system 10 does not acquire image data during the translation phase from projection angle to projection angle. It is appreciated that if the time to translation to a new projection angle occurs during an acquisition of an R—R interval, the acquisition for that interval is allowed to complete before the translation action is taken by the camera system 10.

The following discussion and parameter configurations are relevant to gated SPECT studies. The acquisition computer 20 allows the user to configure the maximum number of gated segments per R—R interval as either 8 or 16 at input 331. Therefore, if the mean R—R interval was originally computed as 800 milliseconds and 16 segments were selected, then each gated segment would represent 50 milliseconds of the R—R interval.

The present invention also allows the user to select the triggering factor to terminate a particular projection, either the total time per projection, or a set number of detected R—R intervals. Image data from several R—R intervals is taken per projection angle. This is selected at 343. The user may also select R—R interval variance by entering a maximum percent window variance (100%) at 333 and a minimum percent window variance (0%) at 335. The user may also selection a number of good R—R intervals to exclude after a variance outside the above window is detected at input 341. The user may select a fixed R—R interval in the event an automatic R—R interval is not desired at input 337. The user may also allow the R—R interval to be recomputed during the study based on the average of all beats from the previous projection. Session information is also displayed such as the isotope ID may be entered at 351 as well as the patient ID at 353 and the particular view ID at input 355. Imaging of the camera system 10 is initiated by an input selection 357.

As shown above, the present invention allows user configuration of parameters that relate to the R—R interval of the patient heartbeat which is the time interval between successive R waves of the heartbeat wave. Each frame of the gathered gated SPECT data will be a gated dataset representing a segment of the R—R interval of the heartbeat. In the automatic mode (selection 339=0), the time per segment of this gated dataset is established by the data acquisition computer 20 or by the camera system 10 based on the number of dynamic segments selected by the user (8 or 16) by input 331 and the patient's R—R interval as determined or as input via 337. The data acquisition computer 20 or the camera system 10 (via the electrode 25 of FIG. 1) monitors five of the patient's R—R intervals to establish the total cardiac cycle time. This acquisition computer will establish the time per segment to acquire the dynamic dataset based on the number of segments selected by the user (i.e., 8 or 16 between an R—R interval). The segments will represent 100% of the cardiac cycle.

The computer system 20 of the present invention also allows the configuration of acceptable R—R interval variations which are used to establish determination of acceptable and unacceptable heartbeats for imaging purposes. The user may select a timing window around the patient's R—R interval to accept a percent of variance allowed for each R—R interval acquired. This window (see inputs 333 and 335) will encompass a variance from 0 to 100 percent. Also, as a result of a particular variance outside the allowed scope, the camera system 10 is programmed to skip a certain amount of succeeding beats. The user may determine the number of R—R intervals to reject after a variance that is outside the allowable window, see input 341. This number of rejected R—R intervals is programmable. Using a fixed R—R interval parameter selection, the R—R interval will be divided by the originally established time per gated segment, in other words, each segment have a time period of the R—R interval divided by either 8 or 16 depending on the user selection.

For a given projection angle when variable R—R intervals (selected by input 339) are selected, the mean R—R interval used in the previous projection angle acquisition will be used as the R—R interval for the next projection angle acquisition. This means that the R—R millisecond value and the value for each binned gated segment, established at the start of the study, can vary throughout the study. The number of gated segments (i.e., 8 or 16) will stay the same and the data will be binned in the same memory location and the R—R percent variance will remain the same. It is appreciated that the above allows the user to continue the acquisition even if the patent's R—R interval changes during the study.

During a gated SPECT session of the present invention, the camera system 10 periodically communicates with the acquisition computer system 20 to relay certain status information that is displayed on the display screen of computer system 20 (shown in FIG. 3 in status window 365). For instance, the current session time is transferred and displayed by computer system 20 as well as the current projection and the maximum number of frames selected in the gated SPECT study. Also sent to the computer system 20 are the current number of counts per second detected by the detector 12 and the heartbeats detected by the camera system 10. Also reported to the system 20 is the current value of the average R—R interval determined by the camera system 10 and the number of gated frames selected for the study. Also relayed is the status of the maximum number of gated frames selected by the user. This status is periodically transferred to the system 20 and displayed on the computer screen throughout the gated SPECT study for monitoring by the user.

Once the above discussed parameters are selected by the user they may be stored within computer system 20 for later recall and use. It is appreciated that once input, the data acquisition computer will initialize a gated SPECT study on the camera system 10. It is further appreciated that the camera system 10 will supply imaging data to the post acquisition computer system 120. The image data transferred from the data acquisition systems to the post acquisition processor 120 is in the following format viewed in a matrix form but stored as a single object. Down the vertical axis is each gated time interval (segment) of the cardiac cycle (there can be up to 16 of these segments). Across the horizontal are the number of projection angles or frames that can be taken over the total orbit selected (there can be up to 128 of these). Therefore, in a standard gated SPECT session there can be up to 128×16 or 2048 different image frames of raw gSPECT data. Also, each separate image frame may be composed of 128×128 pixels maximum, each pixel representing the number of counts received at that pixel location. Therefore, the maximum data size for the raw data of a gated SPECT session is 2048×128×128 or 33.6 Megabytes of image information. As a single object, the post acquisition computer may display the data in either of two formats: (1) cine (animate) the data in gated fashion per projection angle or (2) cine all projection images for a gated segment.

According to the overall sequences of data acquisition, processing and display of the present invention, a patient is first exercised to stress the cardiac tissues (using a treadmill or bicycle for instance). A radio-pharmaceutical is introduced into the myocardium while it is stressed and follows the blood flow to concentrate in areas of the stressed myocardium. During the imaging session, this radionuclide will remain in these areas, even after the heart enters a rest condition (as is well known). At some point the electrode 25 (a standard 3 or 4 lead ECG placement is positioned over the chest near the heart at a position to best detect and amplify the electrical signal generated by the beating of the heart and the computer system 20 computes an average R—R interval. The patient is positioned in the camera system 10 and a selected data acquisition parameter file is selected entered or modified by user control over the data acquisition computer 20. Next, a gated SPECT imaging session is started on the camera system 10 and operates according to the selected operating parameters supplied by the data acquisition computer system 20. It is appreciated that once initialized, except for some status reporting from the camera system 10 to the data acquisition computer system 20, the camera system 10 is independent and performs the required projection angle motion of the detector 12, gating, and imaging without interface with the computer system 20. All raw gated SPECT image data is sent to the post data acquisition processing system 120 via lines 19, 22 and the communications interface (intermediary) in the system 20.

The image processing and display procedures of the present invention are implemented on the post acquisition computer system and will be further explained below in section III. The post acquisition processing computer 120 performs three major processing steps: (1) processing or reconstruction procedures; (2) image display procedures; and (3) quantitative analysis procedures (a division of the image display procedures) which utilize the functional display rings of the present invention. Each of the three above processing tasks of the preferred embodiment of the present invention include user interface capability (via keyboard 106, cursor control 107 and display unit 105) and will be further explained in discussions to follow.

Figure 4A:
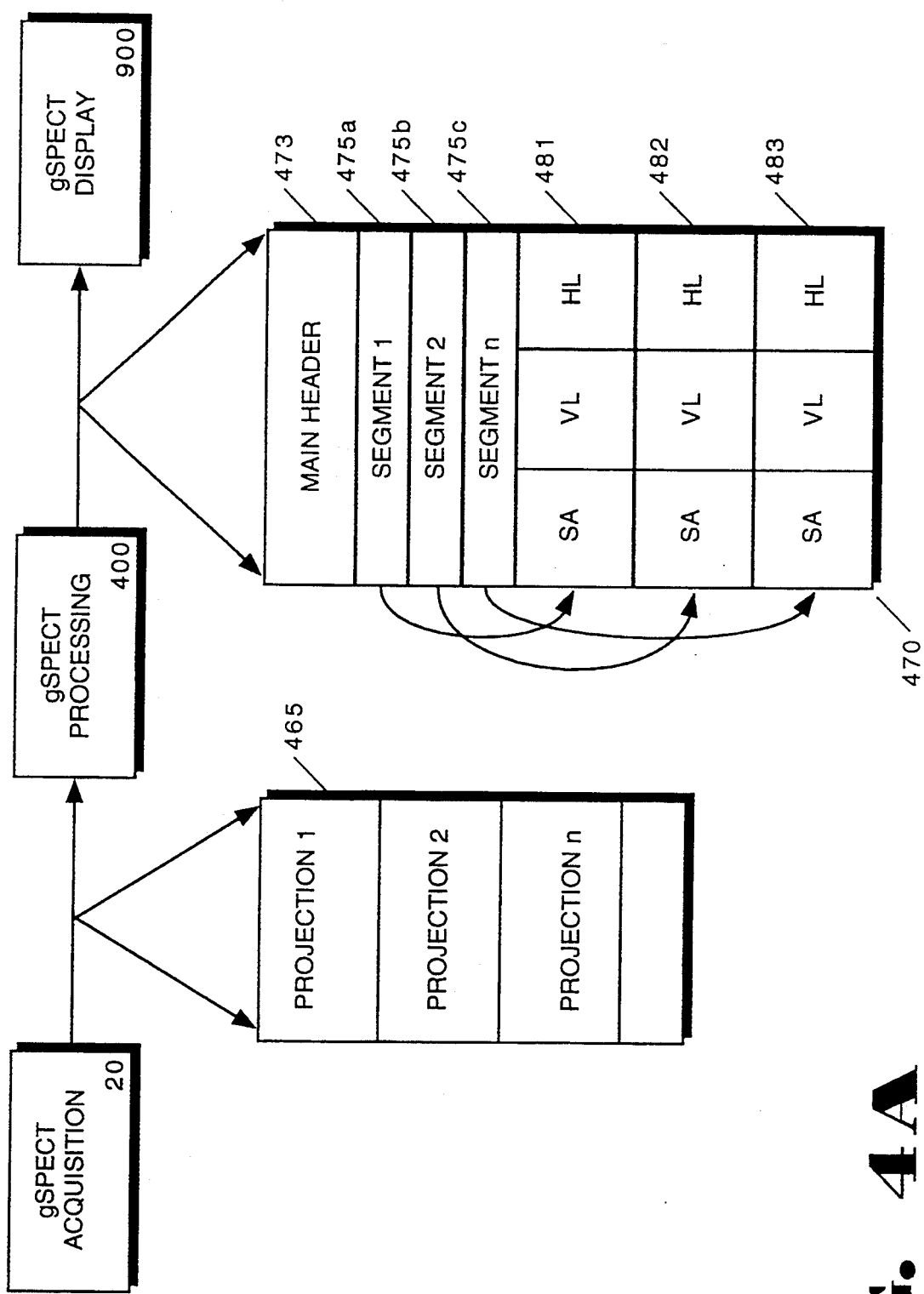
FIG. 4A illustrates the major processes of the invention and data structures.

FIG. 4A illustrates the overall flow of the gSPECT acquisition 20, the gSPECT processing 400, and the gSPECT display 900 blocks including the data structures 465,470 that are passed to each process. The gSPECT acquisition 20 system delivers to the reconstruction processing 400 a raw gSPECT data structure 465 which is composed of raw gSPECT data for each projection angle of the session, as illustrated by FIG. 4A. Each of the individual projection angle datasets is also composed individually of segment datasets for each segment of the cardiac cycle selected for imaging. It is appreciated that the data structure 465 could also be organized first by selected segment and then individually by each projection angle, either fashion is within the present invention. The gSPECT reconstruction processing 400 generates, from the raw gSPECT data structure 465, reconstructed volume image frames within a data structure 470 and passes them to block 900. Structure 470 is composed of a main header field indicating the environment of the session, such as patient ID, date, hospital, camera name and type, isotope used, calibration factors, data sizes, etc. The next sections of the structure 470 are the segment pointers. Pointers 475a indicate the locations of the three datasets (short axis, SA, vertical long axis, VL, and horizontal long axis, HL) for the first selected segment. Pointers 475b and 475c indicate the starting locations for the datasets corresponding to the second and n cardiac interval segments, respectively. Each of these datasets is composed of oblique image frames of a reconstructed volume. Data structure 470 is saved into memory 102 of the reconstruction and display computer system 120. The display processes 900 make use of the data structure 470. Generally, at least the ES and ED segments are found within 470. The data structure 470 also contains a dataset series for the transaxial dataset. Since the transaxial dataset is not pertinent for display purposes it is not illustrated in detail.

SECTION III

Processing Procedures and Related Screen Displays on Display 105

Figure 4B:
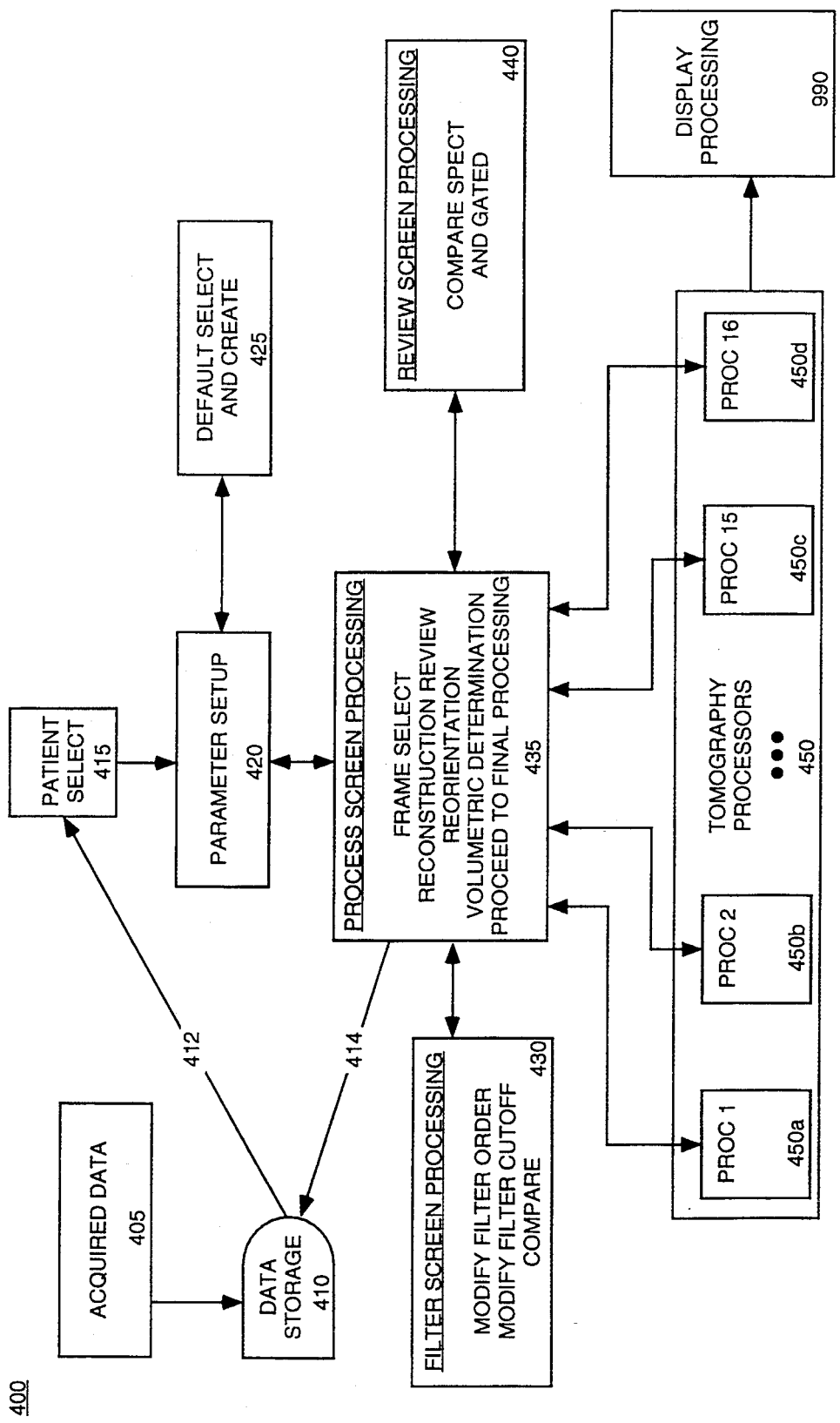
FIG. 4B is a flow diagram illustrating data acquisition procedure and the major processing blocks of the image processing 400 aspects of the computer system 120 of the present invention.

With reference to FIG. 4B, the overall procedures of the processing aspects 400 of the present invention are represented by a functional flow chart. The acquired data from step 405 represents the procedures of the data acquisition systems of the present invention including the camera system 10, and the data acquisition computer system 20. Imaging data originally sent from the camera system 10 is input to the computer system 120 by processing block 405 and stored in a data storage area 104 (of FIG. 2) at step 410. The raw gated SPECT data or raw "gSPECT" image data is reported as pixel sets for each projection angle and gated segment interval; pixel data being in Cartesian coordinates and representing counts detected at that particular location. The data storage step 410 also stores the image data in a particular file that can be recalled and placed into the computer memory 102 for display and processing using predefined patient identification (as discussed above). Once the image data has been received and stored into the computer system 120 for an entire session, at step 415, the computer system 120 allows the user to input a particular patient file for use. The data representative of the selected patient identification is then transferred from the data store to the processing procedures via 412.

At step 420, the user may modify or add particular parameters that control the reconstruction processing (i.e., tomography processing) of the present invention. Once the parameters are defined at step 425 they may be saved to create a new parameter file or a previously defined set of parameters may be selected for use. Once the reconstruction parameters are set up, the user may enter a processing block 435 that generates a process screen. The process screen of the present invention allows selection of particular frames (referenced by pixel locations) of the raw gated SPECT data. This procedure also allows reconstruction review options and reorientation capability to properly align the heart for accepted image display orientations. There are volumetric determinations allowed at step 435 and at this step the present invention allows selection to the final processing steps 450 where the raw gSPECT data or SPECT data is reconstructed using tomography for display using the data storage device 104 as well as memory 102 for image data storage. It is appreciated that once the raw gSPECT data is reconstructed, it may be saved back to the disk storage 104 via step 410 as a result of flow 414 from the process screen 435.

At block 450 the actual tomography (back projection method) processing of the present invention is accomplished in which the raw gSPECT data collected at discrete projection angles is transformed computationally to create volumetric information of the myocardium that can be displayed by a variety of methods at a number of different "slice" positions through the cardiac tissue. The computer processor 101 may perform these computations in a set of parallel processes. As shown in FIG. 4B there are 16 separate processes that operate in parallel (only four are shown for clarity 450a to 450d). It is appreciated that according to the present invention, these separate processes 450a-450d are machine independent and may be executed in parallel on multiple machines. According to the preferred embodiment of the present invention these process tasks 450a-450d are performed by the computer system 120. Each of the 16 processes may operate on a different segment of the raw gated SPECT image data. It is appreciated that after the tomography processing step 450 is complete the present invention instructs the computer system 120 to the display process 900.

From the processing screen procedures 435, the present invention allows modification of particular filters that are utilized in the processes of block 450. These filters may be updated and selected at filter processing block 430 which generates a filter screen. Processing is directed from block 435 to block 430 by selection of a filter selection field. Processing is returned to the main processing block 430 by activation of a proceed selection field 710 (see FIG. 7). The present invention may also direct the computer system 120 from the main processing screen to processing procedures 440 that generate a review screen (via selection of a review selection field) where SPECT data and gated SPECT data may be displayed and gated. Processing may the return to block 435 by activation of a cancel selection field 840 (not shown in FIG. 4B) from the review screen. It is appreciated that normal SPECT data may be created from the gated SPECT data received at step 405. This is accomplished by summing all the gated segment data for a particular discrete projection angle and then performing the reconstruction processes on this summed data. It is appreciated that the present invention allows such functionality at step 440 where both normal SPECT data and the gated SPECT data image frames may be displayed together for comparison. This is advantageous due to the familiarity and established diagnostic value of the normal SPECT imaging data. Also at processing block 440, the present invention allows review of selected raw dam pixels of the frames of the gated SPECT study and allows selection of which image data (presented as pixel ranges or volume limits) to process through block 450.

Therefore, them are four major process procedures and associated screens of the processing tasks of the present invention. They are: the parameter screen, the processing screen, the filter screen, and the review screen. These screens and related processing tasks of the computer system 120 will be discussed further below.

Parameter Screen and Processing 420

The parameter screen 420 of the present invention is described further with reference to FIG. 5. The parameter screen is the entry point for the processing procedures of the present invention. All values of the fields shown in FIG. 5 may be stored as default values for predefined processing sequences. The screen selection item (icon) 561 allows the process flow to enter the processing of block 425 to define and save default selections. The entry of selection 563 transfers processing to block 435, the process screen. From the parameter screen a default screen may be selected. The default screen is important because the entered parameters that were selected by the user may be stored for later use in a processing default and recalled automatically. In the default screen (not shown), the user can create and name a new processing default set. Also selectable is a function that will list the previously predefined processing default sets. Once created, defined default sets may be stored to and recalled from disk 104. The user may highlight a predefined default set and the stored parameters will fill the options on the screen of FIG. 5. All fields may be edited by the user and range checking occurs for each field.

The user may select the icon 535 and enter the patient name, a patient identification and the date of the particular study under review; these selections may be done in a pop up screen input (not shown). Under the processing defaults, the user may select either qualitative or quantitative method at selection 510 using a cycle entry. A cycle entry is a selection list that cycles through the options of the list each time the field is selected by positioning the cursor 5 with the mouse 107 and activating a button located on the mouse 107.

Selection 510 cycles through: quantitative; qualitative; and both. In quantitative mode, the computer system 120 will perform image summation and the output dataset (series of image frames for a selected viewing orientation) will be independently stored in 104. Image summation sums the 8 or 16 gated segments for each angle of projection (i.e., it creates a regular SPECT study). A set of reconstructed images based on the save objects (540) selections from these summed image sets will then be created using the filtration, azimuth and elevation parameters that can be defined by the user (see below). The same values designated by the user on the default screen will be applied to the dataset at the time of any data save function. In qualitative mode the computer system 120 will generate a dataset based on the user defined parameters of FIG. 5 but will not create the summed image dataset (i.e., a gated SPECT analysis is done). In the quantitative/qualitative ("both") mode, both types of summed and not summed datasets are used based on the user defined parameters.

FIG. 5 also illustrates parameter selections of the present invention that relate to filter configurations used in the reconstruction processes 450. At this screen, the displayed filter parameters are the default values presented by the computer system 120. The filter configuration is applied to the gated SPECT data to enhance the data according to the selected parameters. The axis of rotation may be altered via 526. The frequency cutoff value can be entered via input 527 and the order of the filter can be input via 528. The ranges for the cutoff and order are controlled by the type of filter selected. The user can override these values by going to the filter parameters screen and selecting new values. The last values selected are used by the reconstruction process 450. The filter selected for use is entered via a cycle field 520 which cycles through the selections: Butterworth, Guassian, Hamming, Hanning, Wiener, Parzan and Ramp. All of these well known filters are available for use by the computer system 120 and each of the above effect the X-axis (frequency) filtering. As shown, the Butterworth filter is selected. The Y-axis filter (amplitude) also may be altered via cycle field 525 which cycles through smoothing or analytic. When selected as analytic the Y-axis filter will adopt the parameters set for the X-axis filter. If smoothing is selected the Y-axis filter performs a well known smoothing function.

The user interface of FIG. 5 allows the user to input tomographical reconstruction limits at 529 which represents the pixel range used for reconstruction. This screen allows the user to estimate the reconstruction range in order to insure enough disk space is available in 104 for the total reconstruction. The user can set the volume reconstruction limits at 529 for a start and end value. These parameters are also adjustable in the processing screen (discussed below). It is appreciated that once these limits are set in the processing screen, they are used to define the volume for all frame reconstruction. The user interface of FIG. 5 also allows the user to input reconstruction parameters. The reconstruction (tomography processing) of the present invention will produce a three dimensional rendition of the imaged data and will slice that image in order to display dataset frames of three views, the short axis view (reoriented transverse), the horizontal view (coronal) and the vertical long axis view (sagittal). The pixel size of each slice of the reconstructed data is determined by the slice thickness (measured in pixels) entered at 512 via a cycle region. The cardiac orientation is input via 514. It is appreciated that the well known American College of Cardiology or "ACC" orientation may be selected according to the present invention.

The transaxial reconstruction of process 450 will be accomplished by reconstructing from the heart apex to the base, but viewed by the user from feet to head. This means that the first frame number will start at the heart apex and the last frame is toward the base and that the patient's right side is the viewer's left and vice-versa. Input 516 is the decay correction parameter and this allows the user to turn on or off decay correction for processing. Decay correction is applied to both the gSPECT data and the summed image created in quantitative processing. The computer system 120 will obtain the required decay coefficient from a decay data table and apply the correction to the created image data. The save parameters 511 allow the user to determine which files to save to disk 104. If gSPECT files are selected then all of the files required to display the images within the gSPECT display procedures are saved. If the individual files item is selected then files such as transverse, oblique, short axis, horizontal and vertical long axis are saved as the individual files as displayed on the screen. The individual files are saved as fields that can be displayed within other display applications such as myocardial displays. If the parameter for both is selected then gSPECT data files and individual image files are saved as the two above methods increasing storage requirements.

The save objects parameters 540 illustrated in FIG. 5 indicate the objects to be saved as those having a corresponding box checked. The save objects parameters affect two functions of the present invention. First, on the process screen, the user will not be required to define the oblique images or save limit lines for the oblique volume definition if the user has specified only the transaxial image to save. If the user specifies only the short axis image to save then only the limits lines will appear on the horizontal axis image. If the user specifies that all of the images will be saved, then the limits will all appear and have the same functionality as will be discussed to follow. If the raw transverse item is the only selected image then an error message may appear if qualitative mode is selected since gSPECT display procedures require short axis images. The second function of the save objects 540 is to designate a particular extension associated with each file (extensions used are: _Tr, _Sa, _Ha, and _Va for transaxial, short axis, horizontal, and vertical respectively).

Referring still to FIG. 5, if the reoriented transverse (short axis) item is the only selected option then the transverse and oblique images will require axis definition but the vertical long axis image will not appear in the bottom frame 635. Also, the short axis image in the first frame of the bottom row would not allow limit definitions (by vertical and horizontal volume limits lines) since the horizontal and vertical long axis dataset images created from this image are not selected for storage. The horizontal long axis image does not require creation limits. If the Coronal (horizontal long axis) is the only option selected an error message may appear if qualitative mode is selected because the gSPECT display procedures require short axis images. If the Sagittal (vertical long axis) is the only selected option, the transaxial and oblique images display and require axis definitions. The short axis image 694 and the vertical long axis image 696 display in their appropriate viewports with the short axis image requiring creation definition.

The parameters 530 of FIG. 5 relating to the segments to process allow the user to select any variation of the 8 or 16 gated segments of the R—R interval for the reconstruction process. In many cases for gated SPECT, the user will want only to process two segments, the end-diastole and the end-systole gated segments. Parameters 530 allow the user to select only those segments that are necessary for their particular method of processing and interpretation. Note that although the user can select a subset of the projection data, during the review the user will be able to display any projection angle image in cine (animated) motion. It is appreciated that the present invention requires at least one segment box to be selected to process a gated SPECT study. The user selects the proceed region 563 which transfers the user from block 420 to the procedures of the computer system 120 related to the main processing screen 435 when the parameters of the parameter screen are configured.

Processing Screen and Procedures 435

Figure 6:
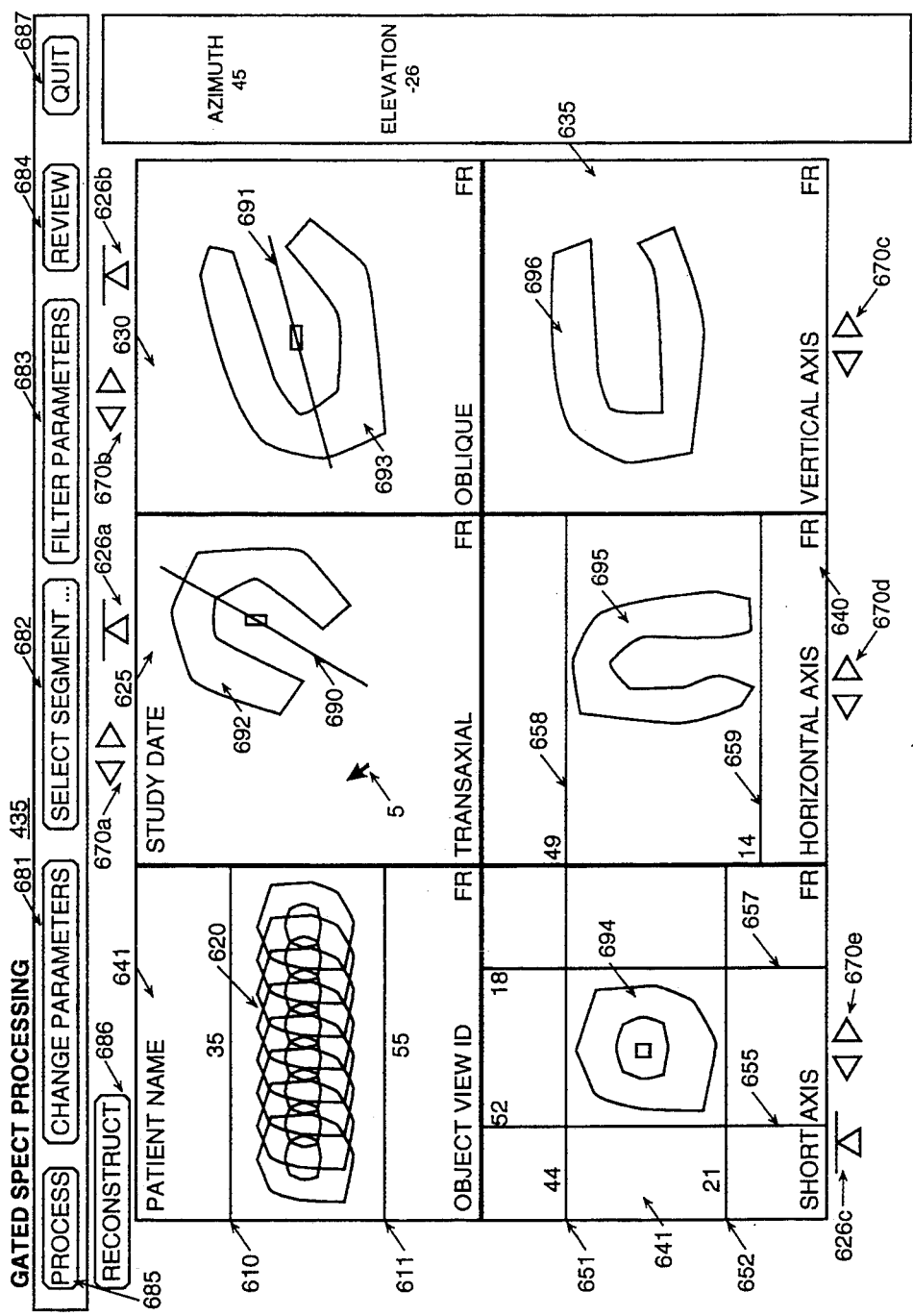
FIG. 6 is an illustration of the main processing screen of the processing (reconstruction) section of the present invention.

The procedures 435 of the computer system 120 related to the processing screen of the present invention are described in relation to the processing screen as shown in FIG. 6. The processing screen procedures allow the user to reconstruct the transverse and oblique images based on upon the parameters selected in the parameters screen. When the screen initially appears a selected image 620 from a particular projection angle of the raw gSPECT data is presented in window 641. The lowest numbered segment selected by the parameters 530 of FIG. 5 is displayed initially. However, by selecting the select segment cycle field 682 alternative segments may be introduced into the window at the same projection angle. Also found are two horizontal lines 610 and 611 that traverse across the window 641. These lines are used to select the region of the raw gSPECT data for reconstruction and are called the transaxial limits. The cursor 5 and mouse 107 may be used to select one horizontal limit line at a time and adjust the line vertically. As the line adjusts up and down, the pixel number represented by the line position is displayed next to the line. In FIG. 6, pixel 35 is selected by line 610 and pixel 55 is selected by line 611. These two limit lines and associated pixel ranges are used in part to select the raw data limits (i.e., those frames within the horizontal lines) to be utilized for the reconstruction procedure 450 by selecting a center volume or slice of data that falls between the adjustable limit lines 610 and 611. Once a suitable data range to the user has been selected by the user, the reconstruct selection field 686 is activated and the full volume of the image data for a particular segment will be quickly reconstructed using the selected parameters by the reconstruction process 450 and a single transaxial image frame displays in 625.

The image processing output from a single slice of the full volume will be utilized to determine the azimuth and elevation parameters for oblique reconstruction. In effect, activation of 686 causes only a preliminary reconstruction output of a small portion of the image data that will be used to determine elevation and azimuth values.

Once these display orientation parameters have been set, as well as other filter parameters, the final reconstruction processing of all the image data selected within three sets of volume limit lines 658, 659 and 651,652 and 655,657 will be performed and displayed in the display processing. It is appreciated that the reconstruct selection field 686 only performs the reconstruction processing for the full volume of the segment selected of image data for each projection angle and the results of this preliminary transaxial reconstruction are used basically to select the azimuth and elevation parameters. Once selected, the total selected image data is reconstructed by activation of the process key 685.

When the preliminary reconstruction completes, a transaxial display image 692 will appear in window 625 of this reconstructed slice. Once the full volume for one segment is reconstructed, the user can advance the transaxial slices (frames) forward and backward using the arrow icon 670a. This action will cause the computer system 120 to display a new transaxial image each time the arrow icon 670a is selected. When satisfied with the displayed transaxial image 692, the user places the cursor 5 in the transaxial viewport 625 and may adjust the alignment of the line 690 (i.e., the line is dragged) from apex to base of the image 692 to provide proper orientation. This movement of the line 690 defines the azimuth degree offset of the heart and will generate a vertical axis image 693 in the viewport 630 to the fight when defined. The user can define the azimuth parameter as many times as required and the computer system 120 will generate an oblique image 693 in viewport 630 for each adjustment. The azimuth angle selected will be displayed in numeric form within the processing screen of the present invention, here 45 degrees.

Referring still to FIG. 6, when satisfied with the selected azimuth image, the user places the cursor in the vertical axis viewport 630 and using the cursor, modifies the alignment of line 691 so that it extends (i.e., the line is dragged) from apex to base of the heart to define the proper heart elevation for the reconstruction process. Upon defining both azimuth and elevation angles, three images are then calculated by the computer system 120 of the present invention and displayed in the short axis display 641, the horizontal axis display 640, and the vertical axis display 635. The user can redefine the elevation as many times as required. If the user redefined the azimuth, then the elevation must also be redefined and new short, horizontal and vertical axis images are computed. A marker appears marking the center of the slice volume of the transaxial image 626a, the vertical axis image for elevation determination 626b, and the short axis image 626c. The elevation selected will be displayed in numeric form within the processing screen, here −26 degrees. The user can advance any of the images by frame advance arrows 670a, 670b, 670e associated with the particular image viewport 625, 630 and 641, respectively.

There are three pairs of limit lines that are used to select the final reconstruction volume for storage by selecting particular pixel ranges of the raw gSPECT data for use by the reconstruction procedure 450 of the present invention to generate the reconstruction images. The short axis viewport 641 allows selection of both the horizontal and vertical long axis pixel limits. The horizontal long axis viewport 640 allows selection of the short axis pixel limits. The cursor 5 may be positioned on any of the limit lines to adjust the pixel location. The purpose of pair 651,652 and pair 655 and 657 is to allow the user to define the reconstructed volume to save for the saving of both of the vertical and horizontal long axis image sets. Lines 651 and 652 are used to set the limits for the horizontal long axis range. The pixel number selected by a particular limit line is also displayed in numeric form, for example according to the positions of limit line pair 651 and 652 the pixel range from 21 to 44 has been selected for the horizontal long axis slice dimension. The purpose of pair 658 and 659 is to define the short axis image sets. According to the positions of limit line pair 655 and 657 the pixel range from 52 to 18 has been selected for the vertical long axis slice dimension. Within the horizontal viewport 640, according to the positions of adjustable limit line pair 658 and 659 the pixel range from 14 to 49 has been selected for the short axis slice dimension. The above pixel ranges (volume limits) will be utilized to define the final volume for storage by block 450.

It is appreciated that the limit lines are color coded as well as the viewport perimeters for viewports 641,640 and 635 for ease of identification within the present invention. To this extent, limit lines 651 and 652 as well as viewport 640 perimeter are green, limit lines 655 and 657 as well as viewport 635 perimeter are blue, and limit lines 658 and 659 as well as viewport 641 perimeter are red. Throughout the present invention, with reference to screen orientation, the color red is used to indicate data representing the short axis view and dataset, green represents data for the horizontal long axis view and dataset and blue is used to represent data of the vertical long axis view and dataset. Once the final process selection 685 is activated, the computer system 120 begins processing of the image data based on the input parameters using process block 450. The application will process all of the raw gSPECT data within the limit lines 610 and 611 and will only reconstruct the volume identified by limit lines 651,652 and 655,657 and 658,659. Each selected segment of the cardiac cycle will also be processed.

The user can select the change parameters selection field 681 to advance to the parameters screen. This allows the user to change any of the initial parameters set. The user can only select this option before the process selection field 685 is activated for final reconstruction processing. The user can also activate the selected segments selection field 682 which causes the computer system 120 to display a list of the available gated segments for selection. The list is determined based on the checked boxes 5.30 of the parameter display. This selection field is only available for selection before the process selection field 685 is selected. The user may also select the filter parameters selection field 683. This selection causes the computer system 120 of the present invention to advance to the filter screen (discussed below) where the user can modify the filter parameters selected and used for reconstruction. Updating these parameters will affect the parameter screen and the filter screen. The filter parameters selection 683 is only available before the selection of the processing selection field 685. Also, the user may select the review selection field 684 which will advance the computer system 120 to the review screen (discussed below). The review screen also allows observation of the selected segments (of the parameter screen) both in projection cine and gated cine mode. It is appreciated that via the processing screen, the user can select any of the five update arrows 670a–670e and step the image frames in the corresponding viewports 625, 630, 696, 640, and 641, respectively, by slice increments by either increasing or decreasing order.

Total Reconstruction Processing

It is appreciated that once the azimuth, elevation, filter parameters, selected gated segments volume limits, and transaxial limits are defined, the final reconstruction process by the computer system 120 may be initiated by the user based on the three pairs of volume limit lines plus the transaxial limit lines 610 and 611. This occurs by the user selecting process selection 685. The entire processing time is based on the volume of image data selected by the volume limit lines, as well as the parameters set by the data acquisition computer 20 and the volume of raw gSPECT data selected by limit lines 610 and 611. However, a maximum processing time is approximately one and one half minutes to two minutes. Only the selected segments will be reconstructed and saved. During the processing procedure, the quit selection field 687 may be activated by the user to terminate the present processing task of the present invention. It is appreciated that there are a number of well known processing procedures for back projection reconstruction, or tomography as it may be known, based on a given set of gated SPECT input and selected reconstruction value. The present invention may operate equally well with a number of such well known reconstruction processes and they may be advantageously used within the present invention as applied via the computer system 120.

The reconstructed volumes are saved to disk 104 by the computer system 120 and those saved are a function of which image datasets are selected for storage by the parameters screen. If the transaxial image is the only image marked to save, then the option to generate the oblique images is not available within the computer system 120. If any of the oblique images are marked to save then all of the oblique images are computed. If the short axis image is marked to save then the only limit lines that appear in the processing screen are the limit lines displayed on the horizontal axis image in viewport 640. If the horizontal or vertical axis are marked to save then only limit line that appear are the limit lines on the short axis image in viewport 641.

As a result of the total reconstruction process 450, the present invention will generate four datasets each representing a series of slices of the reconstructed volume, a transaxial series dataset, a short axis series dataset, and vertical and horizontal long axis series datasets. The number of image frames in each series depends on the pixel ranges selected for that series by the limit lines selected within the main processing screen and the pixel length of each slice. The display processes of the present invention provide various methods and mechanisms to display and quantify the data within the image frames of these three series or datasets.

Filter Screen and Procedures 430

Figure 7:
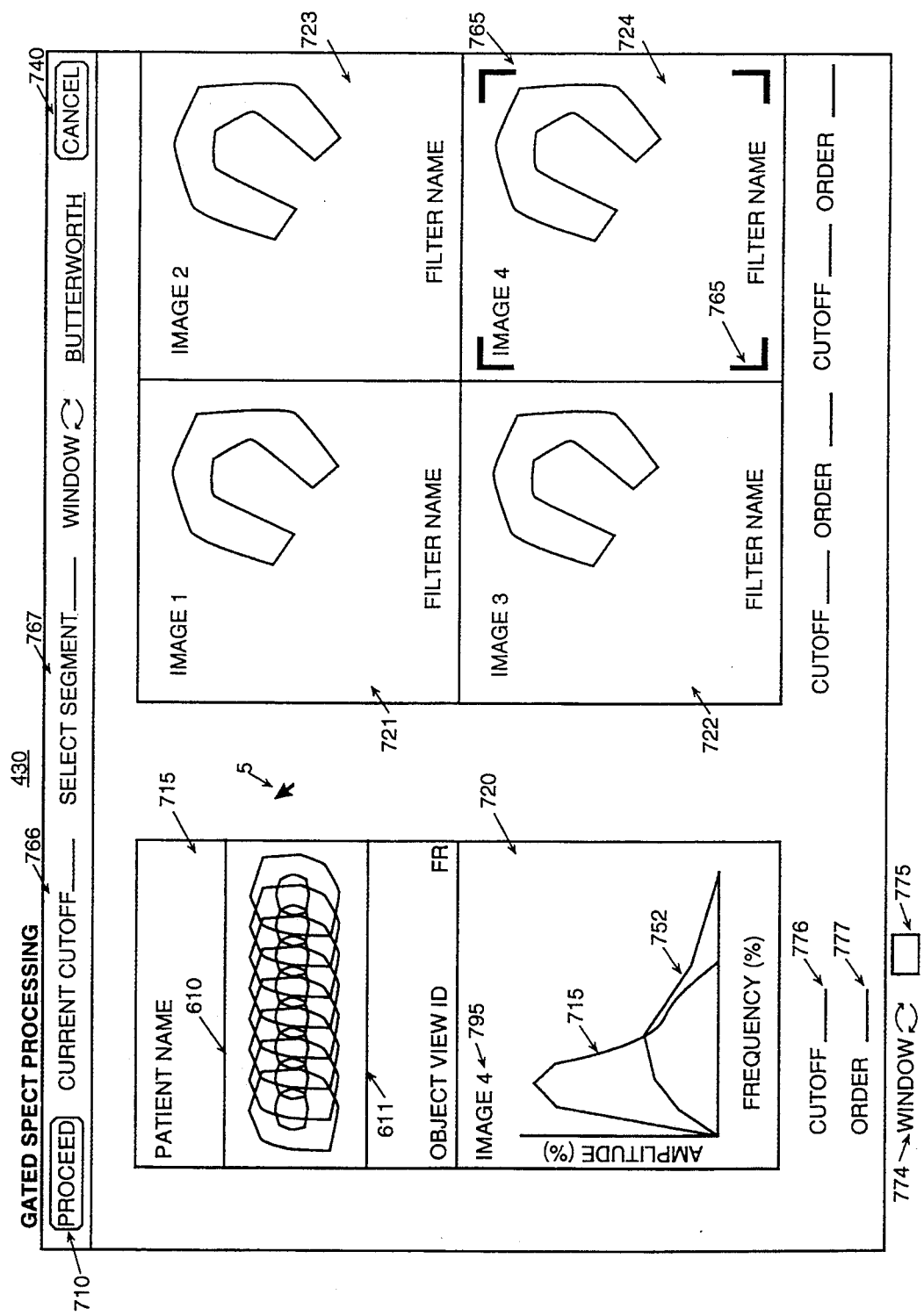
FIG. 7 illustrates the filter screen of the filter processing of the present invention allowing filter parameter modification and storage.

The user will advance to the filter screen of the present invention by selection of the filter parameters selection 683 from the processing screen. The filter screen and related processing tasks of the computer system 120 allow the user to select the type of image reconstruction filter as well as the filter parameters for each selected filter type in detail. The purpose of the filter screen is to allow the user to visually inspect the reconstructed images based upon any user defined filter combination or filter set. The filter screen is shown in FIG. 7. By displaying results of various filter parameters, the present invention allows the user an opportunity to observe and select the filter set that provides the best image for the reconstruction data.

Refer to FIG. 7. Specifically, the proceed selection 710 may be selected by the user via cursor 5 to accept the filter and/or parameters selected by the user which are currently displayed in viewport 720 and also to advance the user to the processing screen 435 of the present invention. Any changes recorded by computer system 120 will become the default parameters for processing and will be reflected in the text field located on the filter screen and the cycle fields located on the parameters screen. The cancel selection field 740 when activated by the user will reject all changes to the filter parameters and returns the user to the processing screen. The current cutoff text field 766 informs the user of the current filter cutoff value selected. It is updated by the computer system 120 every time the cutoff value of the filter curve graph is changed via keyboard control and input 776. The current filter order text field 767 is a text field informing the user of the current order value selected by the user via keyboard control and input 777. It is updated according to user interaction. The type of filter selected for use is entered via cycle field 774 and is called the window cycle field. When selected by the user, via the cursor, a pull down window 775 may also be displayed illustrating all of the well known filter types that are available for the present invention (i.e., Butterworth, Guassian, Hamming, Hanning, Ramp, and Parzan). The user may use the cursor 5 and the mouse to select (i.e., highlight) a particular filter type for use in reconstruction processing 450.

Displayed in the filter screen of the present invention in viewport 715 is a raw gSPECT projection of the current gated segment of the ECT image. The same horizontal reconstruction limit lines 610, 611 are present as discussed in the processing screen. These limit lines determine the volume of interest for the filter selection and determine a midpoint slice for analysis. These limit lines may be adjusted (dragged) by the cursor 5 to define a new midpoint (the default limit lines are those as defined by the processing screen). There are also four viewports 721,722, 723 and 724 each containing the same image (but based on an independent filter set) defined from the midpoint slice of the limit lines outlined on the raw data image of viewport 715. The filter name text field associated with each viewport indicates the filter type and parameters for that specific image in the associated viewport. All four viewports can have a different set of filter parameters.

Each viewport image of the above may be independently configured with separate filter parameters. The filter parameters are adjusted for each of the four viewports by first using the cursor 5 to select a particular viewport by activating the viewport region on the display screen 105. The selected viewport will then be highlighted by a set of four blue corner tabs 765 which surround the selected viewport and the filter parameters for that viewpoint will be displayed in viewport 720. In FIG. 7 the currently selected viewport is viewport 724 and is shown selected by tabs 765. The filter set for this selected viewport is therefore generated in viewport 720 by computer system 120. Information regarding the selected filter parameters for each viewport is also displayed near the associated viewport for display including the filter type associated with each image. For instance, viewport 721 has associated information regarding: (1) the cutoff value; (2) the order; and (3) the filter name of the filter used. The same is true for viewports 723, 722, and 724.

The computer system 120 will reconstruct one slice (the center slice) of the raw gated SPECT data for all projection angles using the current filter parameters for each of the four viewports and display an image for each. Each time the viewport is selected and the filter parameters are modified for the selected viewport, the computer system 120 will reconstruct the new image. Only the selected viewport will change in this case. The center slice location may be modified by movement of the limit lines 610 and 611. Once a new center line is selected, the display for all viewports will update to reflect the new slice reconstruction. It is appreciated that only one viewport is active at any given time according to the present invention and only the active viewport changes according to modifications in the filter parameters.

Beneath the raw data viewport 715 is the filter function graph viewport 720. This graph is the same graph utilized within the SPECT reconstruction program indicating the amplitude (y-axis) and the frequency (x-axis). The graph will correspond to whichever of the four viewports is currently selected by the user (i.e., highlighted with the blue corner tabs 765); adjacent to the viewpoint 720 for the filter is an indication 795 of which viewport image is associated with the currently displayed falter information, This indicator may also be displayed beneath the filter viewport 720. The viewport indicator 795 will change as new viewports are selected by the user. The filter graph viewport 720 contains two keyboard control inputs 776 and 777 which allow for user modification of the cutoff value and the order, respectively. When a new value for any of these two are input, the appropriate filter graphs 751 and 752 will update in time. Filter graph 751 represents the selected window and graph 752 represents the filter function. Further, under keyboard or cursor control, the type of filter can be selected via cycle field 774 and/or window 775. Upon selection of a new filter type (or a new cutoff value or a new order value), the filter graph in viewport 720 will update as well as the currently selected viewport image, in this case the image in viewport 724.

It is appreciated that when the proceed 710 selection is activated by the user the filter parameters set corresponding to the currently selected viewport (i.e., the viewport highlighted by the blue tabs 765) will be selected as the filter parameters used for the final reconstruction processing 450. In other words, the filter screen of the present invention gives the user another avenue to input the filter parameters of the parameter screen. It is appreciated that the filter screen is advantageous because of the ability to illustrate multiple viewport images corresponding to different filter parameters for comparison and selection purposes. It is also appreciated that selection of either cancel 740 or proceed 710 will instruct the computer system 120 to return to the processing screen. Selection of cancel 740 returns to the processing screen without entry of the modified filter parameters.

Review Screen and Procedures 440

Figure 8:
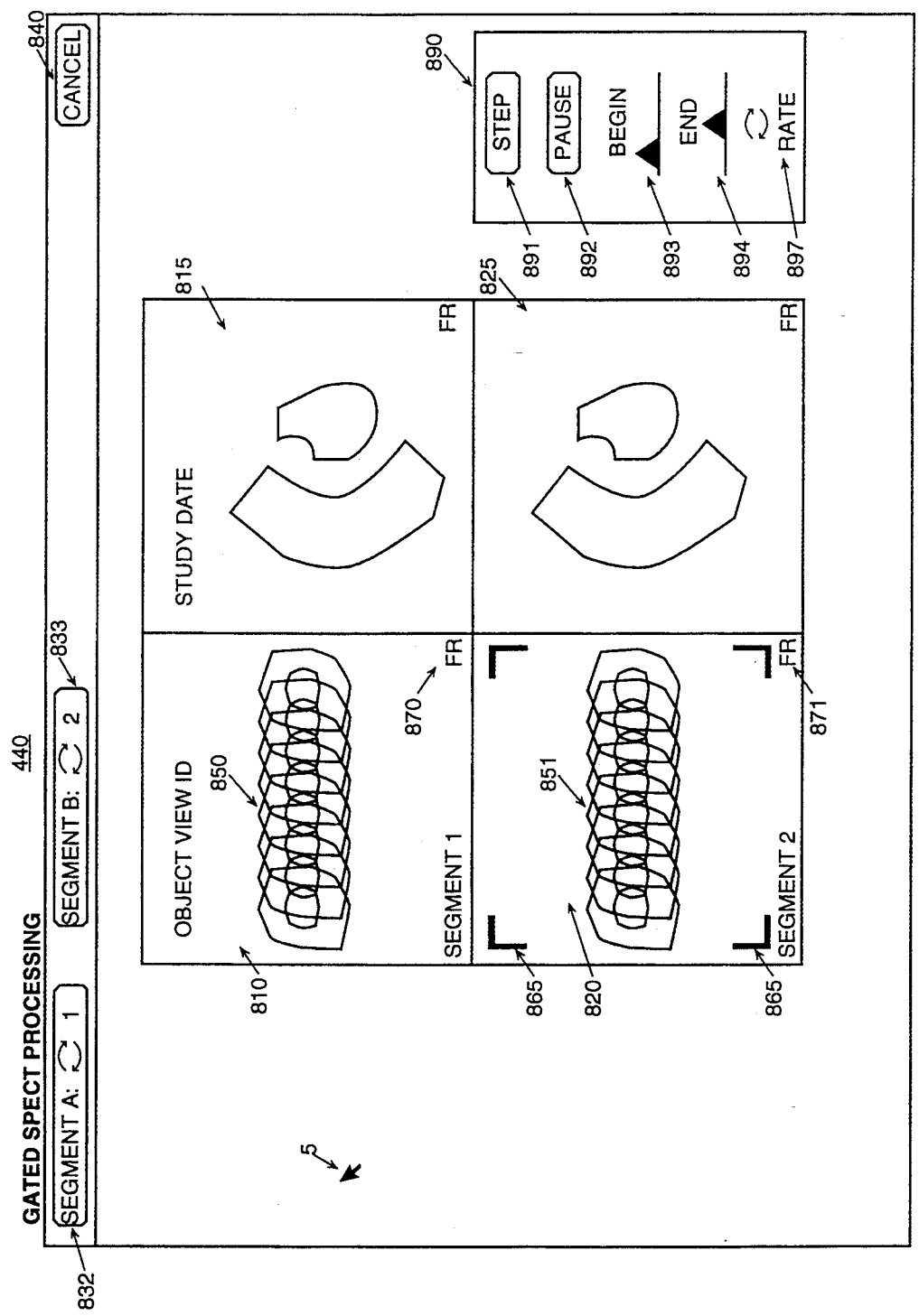
FIG. 8 is an illustration of the review screen of the present invention allowing display of cine SPECT and cine gated images of the raw gated SPECT data.

The user will advance to the review screen and related procedures 440 of the present invention upon selection of the view selection field 684 of the processing screen. FIG. 8 illustrates the review screen. The purpose of the review screen is to allow the user a quick and efficient method to review the raw gSPECT data and provides multisegmental visualization of the raw gSPECT dam. Within the review screen, the user can cine a gated segment of SPECT data or cine a SPECT azimuth's gated data. The review screen is designed with four view ports, the two on the left 810, 820 display the respective raw SPECT images while the right viewports 815, 825 display the respective raw gated images. Therefore, the user can view the segments selected in either projection cine or gated cine. Typically the segments selected will be end-diasrole and end-systole, however any two segments selected for reconstruction may be displayed.

Referring to FIG. 8, viewport 810 displays the raw gSPECT image data for a selected gated segment. Typically this segment would be the end-diastole segment. By selecting a viewport with the cursor 5, a set of blue comers 865 will highlight the selected viewport. Here the selected port is 820. According to the present invention, the viewports 810 and 820 display the raw gSPECT information for the selected segments respectively. The user may select, via cursor 5 or keyboard 106 control, to animate (cine) the image in any of the two viewports 810 or 820 through the projection angles that were collected by the imaging camera system 10. This is called cine of the raw SPECT data for a given segment; as the image cines, the image data (gSPECT) for current projection angle is displayed on the screen 870 and 871. It is appreciated that present invention allows the rate of cine motion to be increased or decreased according to user control. The images 850 and 851 are a representation of this cine motion through the angles of projection that the detector 12 rotated through when collecting the image data for the selected segments 1 and 2 respectively. These selected segments refer to the segments that were originally selected for imaging at the parameters screen. According to the display of FIG. 8, the viewport 810 cines (by angle) the end-diastole phase of the cardiac cycle while viewport 820 cines (by angle) the end-systole phase of the cardiac cycle, both in synchronization according to the given projection angle.

It is appreciated that when selected viewports 815 and 825 of the present invention display an image at a particular projection angle that corresponds to viewports 810 and 820 respectively for a particular selected segment. These viewports 815 and 825 are the gated viewports and will cine according to the gated segments of the R—R interval for one particular projection angle. When these viewports 815, 825 cine, the entire cardiac cycle may be viewed by animation according to a particular projection angle that may be determined by viewports 810 and 820. The projection viewports 810 and 820 will cine the respective image for the 1–128 projection angle frames (depending on the number of selected frames in data acquisition). The gated viewports 815 and 825 cine the respective image for the 1–16 gated segment frames (depending on the number selected in data acquisition).

More specifically, in order to control the cine function of the images, a cine function selection region from an image control selection field must be activated by the user; this is accomplished by activating a cine icon using cursor 5. When all of the viewports are selected and cine is turned on by the user, the gated images of viewports 815 and 825 will begin to cine immediately through the segments of the R—R interval for a given projection angle. When the cine function (i.e., by angle of projection) is initiated for the viewports of the raw SPECT data at 810 and 820, the gated images within viewports 815 and 825 will "freeze" and the SPECT images in viewports 810 and 820 will begin to cine through projection angles for a particular segment. When the SPECT images of the present invention in viewports 810 and 820 are paused by action of the cursor, the gated images in viewports 815 and 825 will again begin to cine (i.e., by segments of the cardiac cycle) but will be displayed according to the angle of projection displayed by the corresponding frozen frame of the SPECT images of viewports 810 and 820. It is appreciated that the present invention controls the projection angle for the images of the viewports 815 and 825 according to the projection angle represented within viewports 810 and 820 once paused. It is appreciated that according to the present invention, the gated images of viewports 815, 825 cannot be controlled for pause, start, or step via the images in the viewports 810 and 820.

Duplication of the SPECT images (i.e., viewports 810 and 820) and duplication of the gated images (i.e., viewports 815 and 825) is implemented by the present invention in order to present end-diastole (ED) segment and end-systole (ES) segment, top and bottom respectively. It is appreciated that selector and cycle field 832 allows the user to select a different segment for the top views (viewports 810 and 815) while selector and cycle field 833 allows the user to select a different segment for the bottom two views (viewports 820 and 825). For instance, cycle field 832 can be selected by cursor 5 and a list of the selected segments from the parameter screen will be presented, i.e., a different segment from the list will be displayed each time the cycle field is selected. A selector button on the mouse 107 can then be used to select that particular segment displayed for the corresponding viewports (for top or for bottom).

It is appreciated that for clarity both the projection cine (i.e., viewports 810 and 820) and the gated cine (i.e., viewports 815 and 825) cannot cine at the same time. But the two projection images within viewports 810 and 820 or the two gated images in viewports 815 and 825 or one projection (i.e., viewport 810) and the other gated (i.e., viewport 825) can cine at the same time according to the present invention. Within the review screen, the present invention provides a cancel selection field 840 and when activated will return the user to the processing screen. There are no parameter changes allowed within the review screen.

The present invention allows a pop up window 890 which is displayed by selection of an icon by user control with cursor 5. This window allows fine adjustment of the image display features of the present invention as described above with reference to the selected segment evidenced by the selection comer tabs 865. A step field 891 when activated each time will step, frame at a time, the cine motions of the display images. The pause 892 field will cause the images in viewports 810 and 820 to pause and will therefore allow cine motion of the gated viewports 815 and 825 according to the paused projection angle. The selections for beginning 893 and end 894 define a sub-range of the projection angles that can be used for the projection cine. There is also a rate cycle field 897 that is used to control the rate of the cine motion of the viewports. There is also a direction field (not shown) that controls the direction through which the frames are displayed for projection cine (i.e., from end to last or from last to end).

Generally, it is appreciated that the user can advance to any of the screens (i.e., parameter screen, processing screen, filter screen, review screen) to change any of the parameters during the processing sequence of the present invention as long as the process selection field 685 has not been selected for final processing. This includes the reconstruction selection field 686 as well.

SECTION IV

Display Procedures and Related Screen Displays On Display 105

Figure 9A:
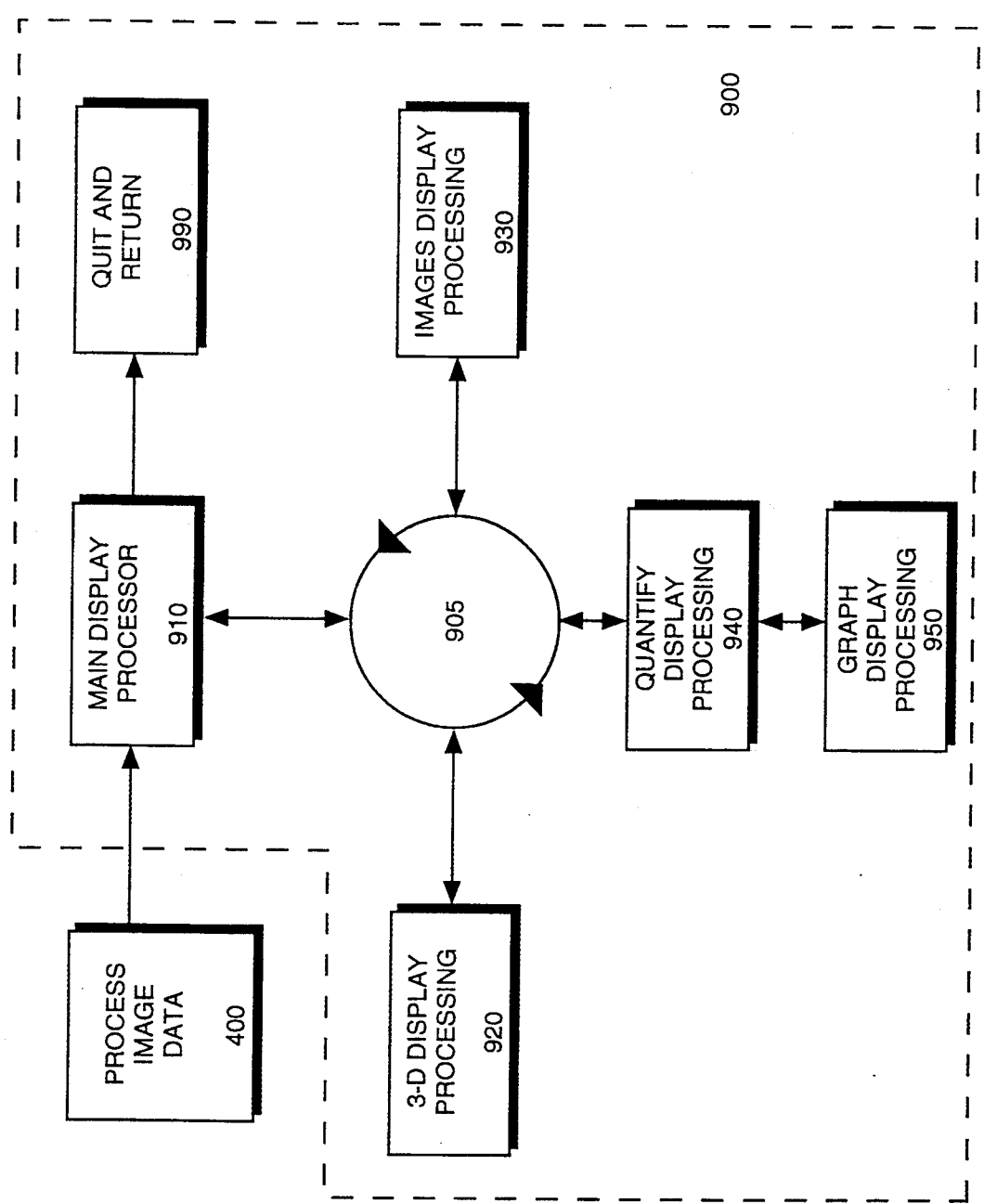
FIG. 9A illustrates the major processing blocks of the display processing 900 of the present invention.

Once the image data is acquired and processed, as discussed above, the reconstructed images are displayed according a variety of different display processes that are compiled within the display process 900 of the present invention. FIG. 9A illustrates main aspects of the display processes executed by the post acquisition computer system 120 of the present invention. Once final reconstruction has been selected and accomplished via block 450 (not shown in FIG. 9A), procedures of the process data block 400 send the reconstructed image data to a main display process block 910 which contains the main display screen. The reconstructed data is saved to disk 104 in multiple series of dataset frames, one for each of the three display orientations and further the above is saved for each selected segment of the R—R interval. The entire file may be saved as a single object in storage device 104. This information is made accessible to the display processes 900. From the main display screen processing 910, a three dimensional (3-D) processing block 920 displaying 3-D screen information can be entered via user activation of a 3-D selection field. Also, the present invention allows the user to enter an images display process block 930 that contains an image screen of multiple data set frames. Third, the present invention allows the user can activate a quantify selection region to enter the quantify display screen processing 940 of the preferred embodiment of the present invention. From the quantify display screen processing, a subset processing block 950 can be entered which performs particular graph display processing of the information presented in by block 940. A subset processing 1510 of block 940 is performed to compute and display the quantitative functional display rings of the preferred embodiment of the present invention. The user exits the display processing routines 900 of the present invention by activating a quit selection region 1028 which is available from the main display screen and upon activation the quit and return processing 990 are entered. From any processing of the 3-D screen 920, the images screen 930, the main screen 910 or the quantity screen 940, any of the other three screens may be entered. This aspect of the present invention is shown by the flow director 905. Flow 905 couples entry of processing blocks 910, 920, 930, and 940. Block 950 is entered only from block 940.

It is appreciated that the functional images of the preferred embodiment of the present invention that display both information regarding wall motion and wall thickening are generated and displayed within the processing blocks 940 and 950, and more specifically within processing block 1510 (FIG. 15) of block 940.

Figure 9B:
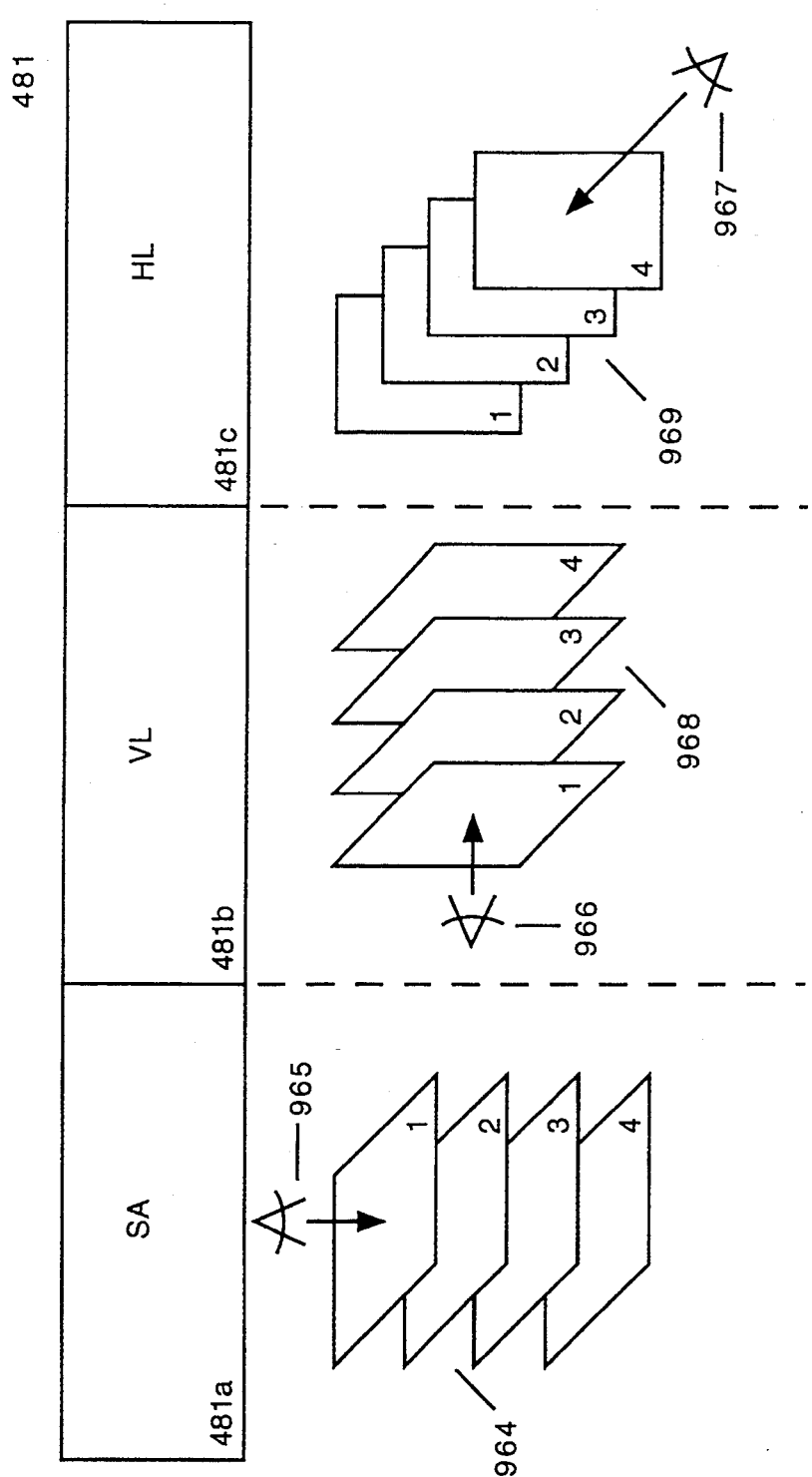
FIG. 9B is an illustration of the three datasets (an associated orientations) created by the reconstruction processing of the present invention.

FIG. 9B represents the data structure utilized by the display proceeding blocks of the present invention. FIG. 9B illustrates three datasets 481 for a given segment of reconstructed data. The short axis dataset 481a, the vertical long axis 481b and the horizontal long axis 481c are illustrated within the structure 481. Each dataset is composed of oblique (orthogonal) image frames of the reconstructed volume for a given segment and FIG. 9B illustrates the viewing orientations for each of the three datasets. The short axis image frames 964 (here four frames are shown) are viewed from the viewing direction indicated by 965 and represent a top view of the oblique slices of the volume as shown. The vertical long axis frames 968 (four are shown) are viewed from 966 and represent a side view of the oblique slices of the volume as shown. Lastly, the horizontal long axis frames 969 (four are shown) are viewed from 967 and represent a frontal view of the oblique slices of the volume as shown. During triangulation, as discussed below, vertical and horizontal cross hairs may be positioned within a frame (say frame 2) of the short axis dataset to selected a particular frame (say frame 1 ) of the vertical long axis dataset and a particular frame (say frame 3) of the horizontal long axis dataset. It is appreciated that the number of slices selected for each dataset and the volume of the reconstructed volume represented by the slices are determined based on the three pairs of volume limit lines discussed above.

Main Display Screen Processing 910

The user automatically enters the main display screen processing 910 upon completion of the final reconstruction processing 450 of the image data (i.e., the task entered after the process 685 selection region is activated). It is appreciated that after final reconstruction processing, only the image data within the selected volume represented within the limit lines (1) for the short axis 658, 659, (2) for the horizontal long axis 651, 652 and (3) for the vertical long axis 655, 657, will be supplied and saved for display. Depending on the slice thickness, as defined in the parameters screen, this selected volume will be used to create different series of frame images. For instance, assuming the slice thickness was one pixel, the number of frames for the short axis view series should be 36 because the short axis limit lines traverse pixels 14 to 49 as shown in the processing screen. The number of frames for the horizontal long axis view series is 24 because the horizontal long axis limit lines traverse pixels 21 to 44. The number of frames for the vertical long axis view series is 35 because the vertical long axis limit lines traverse pixels 18 to 52, as illustrated by the processing screen of FIG. 6.

Figure 10:
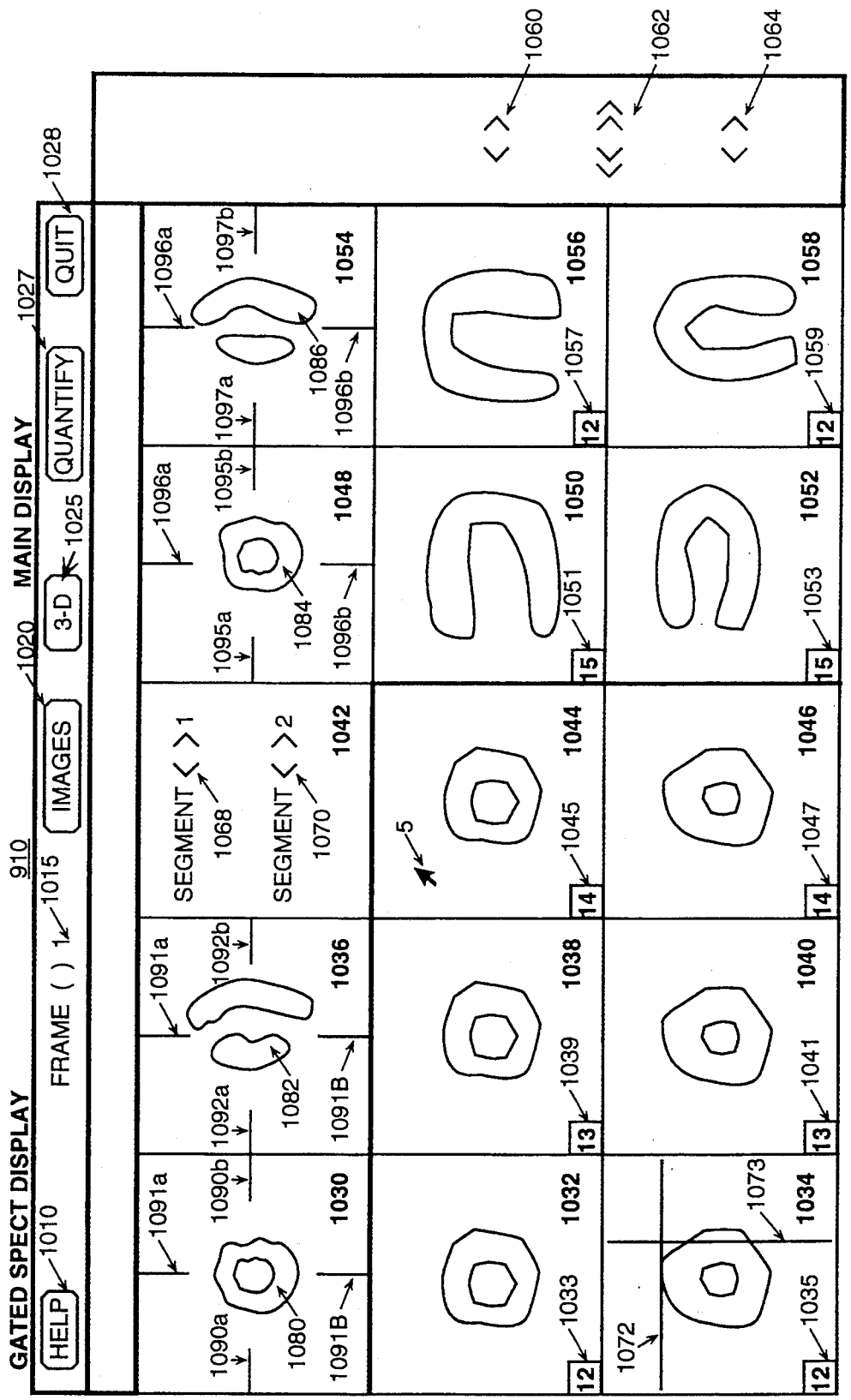
FIG. 10 illustrates the main display screen and related series of short axis images and series of vertical and horizontal long axis images of the present invention.

The main display processing screen is illustrated in FIG. 10. Image information is displayed for two selected segments, segment 1 and segment 2. Typically the selected segments are end-diastole and end-systole. However, any two segments from the parameter screen may be selected for display. Segments are selected by using the segment cycle fields 1068 and 1070. One display segment is selected using the 1068 cycle field by placing the cursor 5 over the cycle field and activating the mouse 107, each time the mouse is activated a new segment within the cycle list is selected and displayed. The other of the two display segments is selected using the 1070 cycle field by placing the cursor 5 over the cycle field and activating the mouse 107; each time the mouse is activated a new segment of the cycle list is selected and displayed.

Refer to FIG. 10. The main display screen contains 14 viewports. Each viewport contains 256×256 pixel resolution within the display screen 105. The top row of viewports 1030, 1036, 1048, and 1054 contain the reference images of both the segments selected and typically represent the end-diastole (viewports 1030, 1036) and end-systole (viewports 1048, 1054) images. These reference images are selected by the present invention as short axis and vertical long axis images of center or mid slices of the reconstructed data. For the end-diastole segment, the upper left viewport 1030 represents the short axis image 1080 of the myocardium and the other left viewport 1036 represents the vertical long axis image 1082. For the end-systole segment, the upper right viewport 1048 represents the short axis image 1084 of the myocardium and the other left viewport 1054 represents the vertical long axis image 1086. The upper viewports are separated by box 1042 that contains the segment select cycle fields for segment selection.

Each of the upper row viewports contains pairs of locator bars that are user adjustable and can be moved up or down or fight or left, as the case may be, by the cursor 5. Each bar of a pair will move together, and any bar of a pair may be activated to adjust both bars. These locator bars are used to select the particular image frames of a dataset to display in the remaining 10 (lower) display viewports. It is appreciated that the locator bars are color coded such that bars 1091a, 1091b and 1096a and 1096b are blue, bars 1090a, 1090b and 1095a, 1095b are green and bars 1092a, 1092b and 1097a, 1097b are red. Specifically, viewport 1030 contains two bar pairs 1090a, 1090b and 1091a, 1091b and the reference short axis image 1080. The first pair 1090a, 1090b of the present invention indicates the position (with reference to the image 1080) of the frame number of the horizontal long axis view dataset to display in viewport 1056 with reference to the first segment (ED). As either bar 1090a or 1090b is moved up or down on the display, the image frame within viewport 1056 increases or decreases in frame number from a minimum of 1 to a maximum of the frames in the horizontal axis dataset (here 24); in this example, the frame indicator 1057 illustrates that frame 12 has been selected for display by the bars. The pair 1091a, 1091b of the present invention indicates the position (with reference to the image 1080) of the frame number of the vertical long axis view dataset to display in viewport 1050 with reference to the first segment (ED). As either bar 1091a or 1091b is moved right or left on the display, the image frame within viewport 1050 increases or decreases in frame number from a minimum of 1 to a maximum of the frames of the vertical log axis dataset (here 35); in this example the frame indicator 1051 illustrates that frame number 15 has been selected for display by the bars.

The short axis viewports (1032, 1038, 1044 and 1035, 1040, 1046) illustrate a series of views for each segment. With reference to viewport 1036, a horizontal long axis image 1082 is shown and within this viewport bars 1092a, 1092b of the present invention indicate the position (with reference to the image 1082) of the frame of the short axis view dataset to display in viewport 1032 with reference to the first segment (ED). As either bar 1092a or 1092b is moved up or down on the display, the image frame within viewport 1032 increases or decreases in frame number from a minimum of 1 to a maximum of the frames in the short axis dataset (here 36); in this example, the frame indicator 1033 illustrates that frame number 12 has been selected for display by the bars. It is appreciated that viewport 1038 will then display the next short axis frame number, here frame number 13 at 1039 and the next viewport 1044 will display the next short axis frame number, here frame number 14 at 1045 for this segment (ED). The series of viewports displayed here for the short axis presentation comprise viewports 1032, 1038, and 1044 for the ED segment (i.e., the first selected segment).

It is appreciated that the above description applies equally to the display processing of the present invention for the other segment (i.e., the ES segment), except different viewports are involved. For instance, viewport 1048 illustrates the short axis reference image 1084 for the end-systole (ES) segment and contains locator bars 1095a, 1095b and 1096a, 1096b. Locator bars 1095a, 1095b control the horizontal long axis frame image number (here frame 12) that is displayed in viewport 1058, these bars may be adjusted to alter the frame number in the viewport. Locator bars 1096a, 1096b control the vertical long axis frame image number (here frame 15) that is displayed in viewport 1052, these bars may be adjusted to alter the frame in the viewport. Viewport 1054 illustrates horizontal long axis reference image frame 1086 and contains locator bars 1097a and 1097b. Locator bars 1097a, 1097b control the short axis frame image number (here frame 12) that is displayed in viewport 1034, these bars may be adjusted to alter the frame in the viewport. Viewport 1040 displays the next short axis frame number, here 13 and viewport 1046 displays the next short axis frame number, here 14. It is appreciated that the reference images (i.e., 1080 and 1082 for ED and 1084 and 1086 for ES) for each segment are a composite of the short axis and a composite of the horizontal long axis. Series viewports 1032, 1038 and 1044 represent the ED segment short axis image frames while the viewports directly beneath them 1034, 1040 and 1046 represent the corresponding ES segments data frames. The user may compare the data frame images effectively using such display. The same is true for the vertical and horizontal short axis data frames for ED and ES segments (i.e., viewports 1056, 1058 and 1050, 1052, respectively).

For each segment, after the user selects the location of bars 1092a and 1092b (for the end-diastole segment), the present invention instructs the computer system 120 to compute the short axis image set and displays the first three frames referenced from the locator bars in viewports 1033, 1038 and 1044 respectively. The same is true for the end-systole segment with regard to viewports 1034, 1040 and 1046. After the user selects the location of bars 1090a and 1090b the present invention computes the horizontal long axis series and displays the first frame referenced by the locator bars in the viewport 1056. The same is true for the end-systole segment regarding viewport 1058. After the user selects the proper location of bars 1091a and 1091b the present invention computes the vertical long axis series and displays the first frame referenced by the locator bars in the viewport 1050. The same is true for the end-systole segment regarding viewport 1052.

Referring still to FIG. 10, the present invention provides the ability to frame advance any of the image frames through the respective dataset within the bottom 10 viewports. For instance, using arrow indicators 1060 and selecting viewport 1032 with the cursor 5, the user may advance or decrement the displayed short axis ED frame through the ED short axis dataset by one each time the mouse 107 is activated. Each time the short axis image at viewport 1032 is updated, the viewports 1038 and 1044 update accordingly in series fashion. The same is true for viewports 1034, 1040 and 1046 for the short axis ES images using arrow field 1064 and selecting viewport 1034. The vertical long axis ED image frame at viewport 1050 may be selected using the cursor and the arrow fields may be activated to increase or decrement the frame count through the ED vertical long axis dataset. The same is true for the ES vertical long axis image viewport 1052 using arrow 1064 and selecting viewport 1052. The horizontal long axis ED image frame 1057 at viewport 1056 may be selected using the cursor and the arrow fields may be activated to increase or decrement the frame count through the ED horizontal long axis dataset. The same is true for the ES horizontal long axis image frame 1059 of viewport 1058 using arrow field 1064 and selecting viewport 1058.

It is appreciated that the number of frame number increments or number of decrements that are applied to a selected frame may be varied by the frame cycle field 1015. The user may select any number, from 1 to the maximum frames in the study, and the frame number will increment or decrement by this number each time the arrow fields 1060 or 1064 are activated. It is further appreciated that a set of double arrow fields 1062 can be used according to the present invention to alter the frame numbers of selected ED and ES images in unison and may be adjusted by the frame update number of field 1015. The above display functionality of the present invention gives the user great flexibility to select particular structures and slices of the image datasets reconstructed image volume for the two segments and to compare, independently, several reconstruction views, such as short axis, vertical long axis and horizontal long axis for end-diastole and end-systole.

The present invention also offers the ability to cine any of the horizontal and vertical long axis viewport images within viewports 1050, 1052, 1056, 1058 by selecting the particular viewport and selecting a cine selection region with the cursor 5. The selected ED or ES viewport will then display each of the gated segments of the cardiac cycle to create an animated image using the particular viewport orientation. The three series short axis ES images and three series short axis ED images may also be displayed in cine motion, however only viewports 1032 and 1034 of the series support cine motion capability. Either viewport 1032 or 1034 may be selected by the cursor 5 and the cine motion selection region is activated. More than one viewport may be selected for cine motion at the same time. For instance, using the above functionality, viewport 1050 and 1056 can be selected and put into cine motion so that a physician could observe both the vertical and horizontal short axis slices of the myocardium during the total cardiac cycle. It is appreciated that any of the 14 display viewports of FIG. 10 may be enlarged by a percentage less than 100% to display an expanded image of the displayed frame of the dataset within the selected viewport.

The frames displayed by the computer system 120 in the main display screen of the present invention may be independently selected according to the locator bars in the procedure discussed above. Given this freedom, there is no particular rule or reason that an object of interest will be displayed in each display frame of the given three views for ED and ES at the same time. Also, since the user is given the freedom to define the reconstructed structure that will correspond to particular frame number ranges within the datasets of the three orientations, there is absolutely no guarantee that frames of the same number for the short axis dataset, or the vertical log axis dataset and the horizontal log axis dataset will contain the same structure. Therefore a frame alignment process is required. The present invention allows a selected structure in one of the three dataset views to be displayed in frames of all three views by adjusting the frame number in the other view datasets until the structure is aligned in all three views for ED and for ES. This frame alignment process of the present invention utilizes triangulation processing. In order to align the particular frames of the three datasets to a selected structure, the present invention enables the user to activate the mouse 107 on a given structure of a given viewport, say viewport 1034 of the ES short axis dataset to display two crosshairs, a horizontal 1072 and a vertical 1073 cross line. The user may adjust the position of either line by movement of the mouse. In viewport 1034, the position of the line 1072 will dictate the frame number to display within viewport 1058 of the ES horizontal long axis data. The position of line 1073 dictates the frame number of viewport 1052 to display for the ES vertical long axis dataset. (Refer to FIG. 9B). Adjustment of the cross lines causes the computer system 120 to immediately compute the frame numbers of the other two view datasets (horizontal and vertical long axis) based on the line positions. When displayed, frame 1052 represents the vertical oblique slice of line 1073 and frame 1058 represents the horizontal oblique view of line 1072. Also, adjustment of crosshairs within viewport 1052 will similarly update frame numbers within viewports 1034 and 1058. Adjustment of crosshairs in viewport 1058 will update the frame number of viewports 1034 and 1052. The same is true for the ED viewports 1032, 1050, and 1056. The user could next select viewports 1034, 1052 and 1058 for cine motion and then observe the motion of the selected object throughout the cardiac cycle over all three orientations (short axis, vertical and horizontal long axis).

It is appreciated that from the processing 910 of the present invention that displays the main display screen, the present invention allows the user to enter an image screen processing 930 by activation of selection 1020, a 3-D screen processing block 920 by activation of selection 1025 and a quantify screen processing block 940 by activation of selection 1027. The display screen tasks are exited via activation of selection 1028, which enters the processing block 990 of FIG. 9A.

Three Dimensional Screen Processing 920

Figure 11:
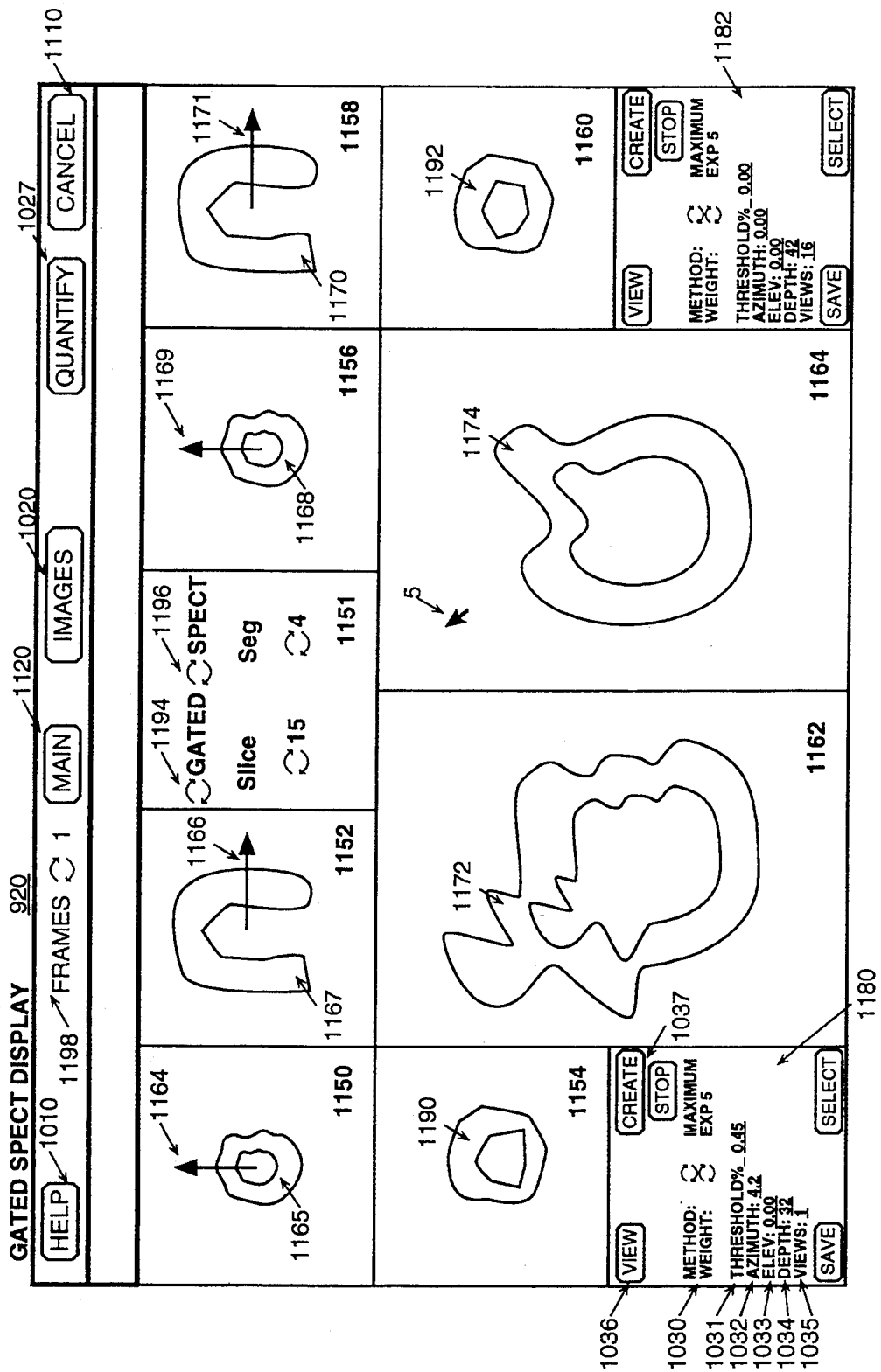
FIG. 11 illustrates the 3-D image screen of the display screen processing of the present invention.

The present invention allows the user to enter the three dimensional screen processing 920 from a variety of entry points, such as from the main display screen, the quantify screen and the image screen processing blocks. FIG. 11 illustrates the features of the 3D screen processing block 920 of the present invention as displayed on the 3D screen of the computer display 105. The 3D screen allows the user to create independently 3D images for two different segments of the gSPECT study (ED, ES). The user can select any of the segments that have been reconstructed with use of the segment cycle fields in viewport 1151. There are two cycle fields 1194 and 1196 for selection for the two segments for display. Field 1194 selects the first segment and field 1196 selects the second segment.

With reference to FIG. 11, the 3D screen is displayed with eight object viewports with the middle two largest viewports 1162, 1164 displaying empty on initial presentation; the 3D viewports 1162, 1164 are 512×512 in pixel display size. These will contain the 3D reconstructed images for the two selected segments. The top four viewports are separated into two groups by a field entry display viewport 1151. The two viewports to the left 1150, 1152 contain a short axis and a horizontal long axis reference image respectively for the first segment. These represent reference images of the segment (ED) that the user may change via a cycle field 1194 within display 1151. The two viewports to the fight 1156, 1158 of the cycle fields represent reference images of the second segment (ES) that can also be changed via the cycle field 1196 within 1151.

Referring to FIG. 11, the four above viewports (1150, 1152, 1156, 1158) of the present invention contain images with interactive cursor arrows that allow the user to change the viewing angle of the associated 3D calculated image. These are the reference images and are the same reference images displayed in the main display screen for the selected segments. The present invention provides an interactive arrow bar 1165 fixed in the center that can be adjusted through 360 degrees (or +/−180 degrees) to represent variable azimuth values from the center of image 1164 within short axis viewport 1150. The present invention utilizes this method to input the current azimuth for display of 3D computed image 1172 of associated viewport 1162 for the ED image. The present invention allows modification of the elevation of image 1172 by adjustment of an interactive arrow 1167 having a fixed center and may be adjusted through 360 degrees (or +/−180 degrees) within horizontal long axis viewport 1152. The reference images within 1150 and 1152 are composite images of the short axis and of the horizontal long axis image sets for the ED segment.

Other parameters effecting the display of the image 1172 may be entered via window 1180 (the ES 3-D image 1174 has a corresponding window 1182), including the method 1030 of 3D computation, either surface rendering or volumetric rendering may be selected. Either process is well known. Also, a threshold value 1031 may be determined indicate the pixel intensity (count number) threshold for display. The indicated azimuth 1032 for image 1172 is 4.2 degrees and the elevation 1033 is zero. These values may be manually entered here via keyboard 106. Other selection regions allow the view parameters to be saved and selected. The view selection field 1036 allows the user to view the 3D image 1172 prior to reconstruction in order to evaluate the selected parameters. The create selection region 1037 causes the computer system 120 to create the 3D image utilizing the desired parameters. The images may be saved by a save option. Other previously saved images may be recalled using the select field. The depth 1034 value may be altered which defines the perspective from the user's eye to the screen of display 1162. The view selector 1035 allows the user to select the number of views to display the 3D image when the image 1172 is placed in cine motion. Options are from 1 to 64. In effect, the present invention allows processing to rotate the displayed 3D image such that all surfaces may be displayed.

Each selected segment also is provided a series image which is visible in short axis viewport 1154 for ED and viewport 1160 for ES of FIG. 11. There are two series viewports 1154 and 1160, one for each selected segment. This series image is a short axis composite and is set automatically at the entry of the 3D screen processing 920. This image may be gated in SPECT or gated cine depending on the selections from cycle entries 1194. If the cycle entry is set to GATE1) then the user may select a particular slice to display, here the slice is 15. According to this selection, viewport 1154 will cine motion all of the segments of the cardiac cycle visible from projection angle 15 and the image 1190 will beat. The cycle entry 1194 may be togged to SPECT wherein a second selection is available for selecting a particular segment for display. When a segment value is entered, the image in 1154 will cine in SPECT mode for that particular segment for all projection angles. In effect, the viewport 1154 will display in cine motion all of the projection angles of the SPECT study for the given segment selected. The present invention allows the user to frame advance and cine the series image set through all slices or all gated frames via viewport 1154 for one segment or viewport 1160 for the other segment. Cycle field 1196 controls the cine parameters for viewport 1160, cycle field 1194 controls viewport 1154.

The user is able to set parameters for a particular 3D reconstruction for a given segment and independently reconstruct the two selected segments. To this extent, the view selection 1036 causes the computer system 120 to generate a single image reconstructed with selected parameters and viewing perspective. The user may control all aspects of image manipulation and reconstruction for a given 3D image for a given segment without affecting the other 3D image. The create selection 1037 creates a full 3D reconstruction image in viewport 1162 based on the user defined parameters. The 3D reconstruction will be reconstructed so that the viewing angle will cine and at the same time cine in gated fashion. Each 3D image may cine in SPECT or cine gated (i.e., beat) according to the present invention. It is appreciated that the series images of viewports 1154 and 1160 may cine in SPECT or cine gated in synchronization with their respective 3D image of 1162 and 1164. It is appreciated that the series images within viewports 1154 and 1160 may be expanded for more database observation.

It is appreciated that viewports 1050, 1052, 1054 and 1162 (the ED segments) may be defined and observed independently from the other set of viewports 1056, 1058, 1060 and 1164 (the ES segments). To this extent, all of the discussions above regarding the configuration and displays available for the ED segments are equally available for the ES segments. Specifically, viewport 1156 and viewport 1158 allow azimuth and elevation definition for the 3D image 1174 of viewport 1164. The parameter window 1182 controls the display of the 3D image 1174. Further, the cycle fields 1196 control the cine motion of viewport 1160 for either SPECT cine or gated cine.

From the 3D processing block 920, the present invention allows the user to activate a main selector 1120 to return to the processing routines 910 or activate a quantify selector 1027 to enter the quantify processing routines 940 or activate an image selector 1020 to enter the images screen processing 930. The cancel selection 1110 cancels the current function and returns to the previous display screen processing that was entered via cycle flow 905.

Image Display Processing 930

Figure 12:
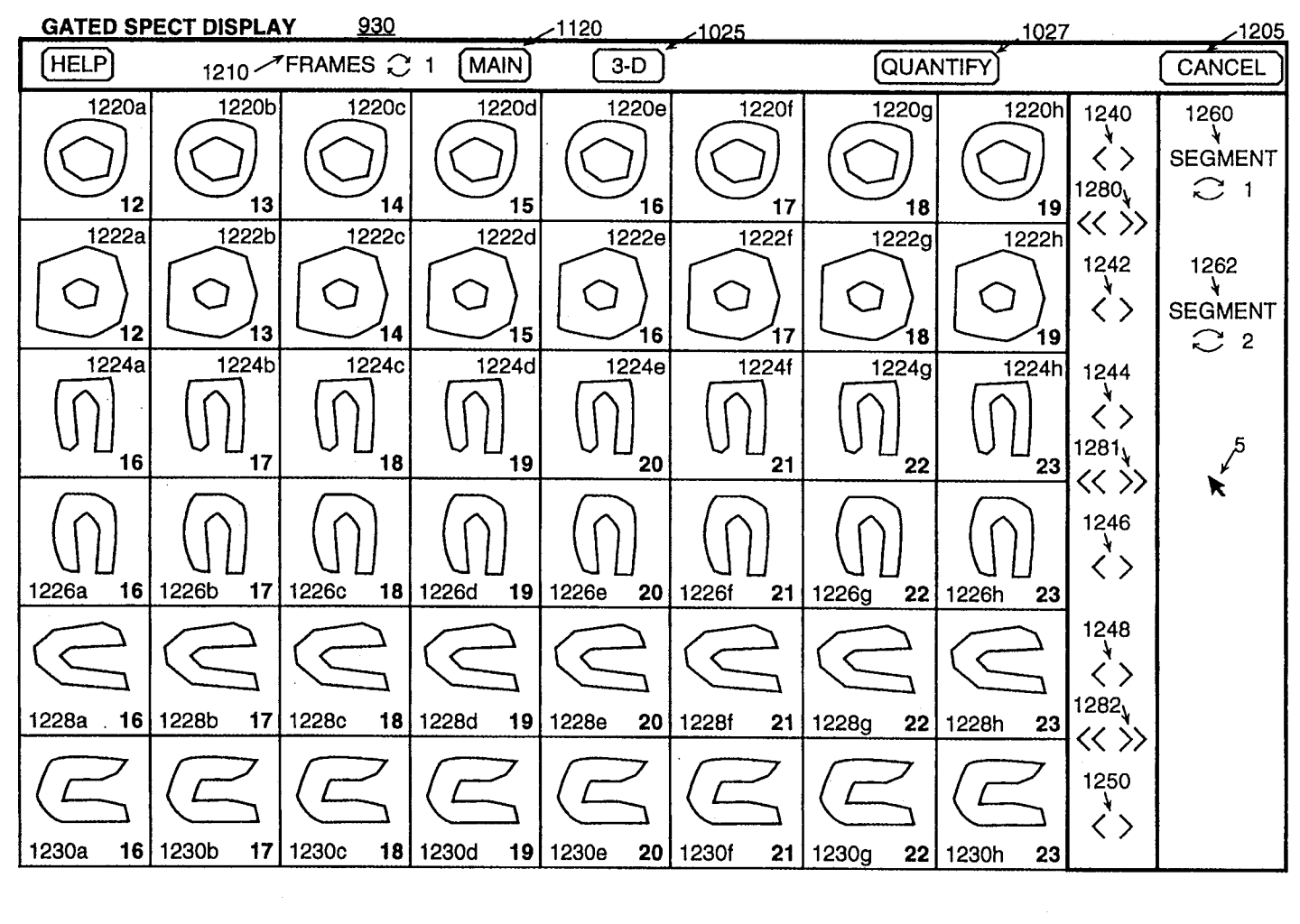

The processing required for the image display screen of the present invention is discussed below. The processing block 930 of the image display screen is designed to display series of frames of the short axis, vertical long axis and horizontal long axis datasets from the two user selected segments. The image display screen is illustrated in FIG. 12. This screen is designed to display a number of different series of image frames to the user for each of the three datasets: short axis, vertical and horizontal long axis, and for two selected segments (typically these are end-diastole and end-systole segments of the cardiac cycle). The image screen of FIG. 12 consists of 48 viewports in total. The viewports are configured in 8 horizontal and 6 vertical frames. Each of the viewport series that correspond to a particular image dataset are color coded in perimeter. The short axis viewports (1220a–1220h and 1222a–1222h) have red boundaries, the vertical long axis viewports (1224a–h and 1226a–h) have blue boundaries and the horizontal long axis viewports (1228a–h and 1230a–h) have green boundaries. The viewports contain frames of the processed SPECT image datasets representing the first segment short axis, the second segment short axis, the first segment vertical long axis, and the second segment vertical long axis, the first segment horizontal long axis, the second segment horizontal long axis datasets.

The two user selected segments are selected via cycle fields 1260 and 1262 for the first and second displayed segments, respectively. According to the images display of the present invention, the first row images (series 1220a through 1220h) are the short axis images from the first selected segment CED), the second row images (series 1222a through 1222h) are the short axis images from the second selected segment (ES), the third row images (series 1224a through 1224h) are the vertical axis images from the first selected segment (ED), the fourth row images (series 1226a through 1226h) are the vertical axis images from the second selected segment (ES), and the fifth and six row images (series 1228a–1228h and 1230a–1230h, respectively) are the horizontal long axis images of the first (ED) and second (ES) selected segments, respectively. Each of the above series of frames display the associated frame number of images in sequence. For instance, series 1220a–1220b displays the frames 12 through 19 of the short axis dataset for the end-diastole time segment.

The present invention allows the user to advance or decrement any of the above frame series presentations by six arrow fields. Arrow field 1240 will advance or decrement the frame count at viewports 1220a through 1220h by using the mouse 107 and the cursor 5 to activate a particular arrow. For instance, when the advance arrow (could be right or left selection) is selected the frame numbers of series 1220a to 1220b change from frame range 12 to 19 to range 13 to 20; likewise when user decremented the series changes to frame range 11 to 18. The same is true for the other five arrow selections. Arrow field 1242 controls the frame range for series 1222a-1222h, field 1244 controls series 1224a-1224, field 1246 controls series 1226a–1226h, field 1248 controls series 1228a–1228h, and field 1250 controls the frame range for series 1230a–1230h.

The frames selection 1210 allows the user to increment or decrement the series frames, as discussed above, by any number of frames input into this field up to the maximum frame number for the dataset. Therefore, if the frame cycle field 1210 is programmed as two, then the arrow fields above will increment or decrement their respective frame series by two frame numbers per selection, etc. It is appreciated that use of special double arrow fields 1280, 1281, 1282 may be used to advance the frames of two frame series in unison that are representative of datasets for both segments of the same orientation. For instance, arrow selection 1281 advances or decrements the frames of series 1224a–1224h and series 1226a–1226h in unison since these correspond to both ED and ES segments of the vertical long axis dataset orientation. By selection of a special mouse button on 1240 a pop-up menu may be displayed (not shown in FIG. 12) illustrating each frame within the short axis ED dataset and the user may scroll down the list and pick a particular frame to display at viewport 1220a. The same is true for the other datasets of FIG. 12.

It is appreciated that the images in the first vertical column of viewports (i.e., 1220a, 1222a, 1224a, 1226a, 1228a, and 1230a) perform a gated cine controlled via a cine selector. When selected, the images will cine in gated fashion to display the entire cardiac function. The images can also be zoomed within the present invention if the frames are selected with corner tabs. However, the cine images will not maintain their zoom or brightness if the images are manipulated in any fashion. The present invention allows any of the images within the displayed viewport to be enlarged by selection of the viewport and activation of an enlargement region via the cursor 5 and mouse 107. Also the images in the first vertical column viewports support triangulation. Any of the three ED viewports may be selected with crosshairs to selects frame of the other two ED viewports using the triangulation techniques as discussed above. The same is true for the three ES viewports of the first vertical column.

It is appreciated that the user may frame align the frames of various different datasets of FIG. 12 using triangulation within the present invention. This frame alignment is accomplished analogously to the triangulation process described with respect to the main display screen processing 910. The images display screen provides the user with a method and display format for observing a vast amount of data frames of the three dataset orientations of the reconstructed volume. Using such a display several structures of the heart can simultaneously be displayed at all three orientations at eight slice positions per orientation and for two segments. Each orientation may also be cine gated. These data display formats offer powerful tools for CAD diagnosis and image comparison.

Within the processing of the present invention related to the image display screen, the user may activate the main selection field 1120 to return to the main screen processing 910, or activate the quantify selection 1027 to enter the quantify screen processing 940, or select the 3D selection field 1025 to enter the 3D processing 920. The user may also select the cancel field 1205 to exit the images screen processing 930 and return the previously entered display screen processing block.

Quantify Screen Processing 940

Figure 13:
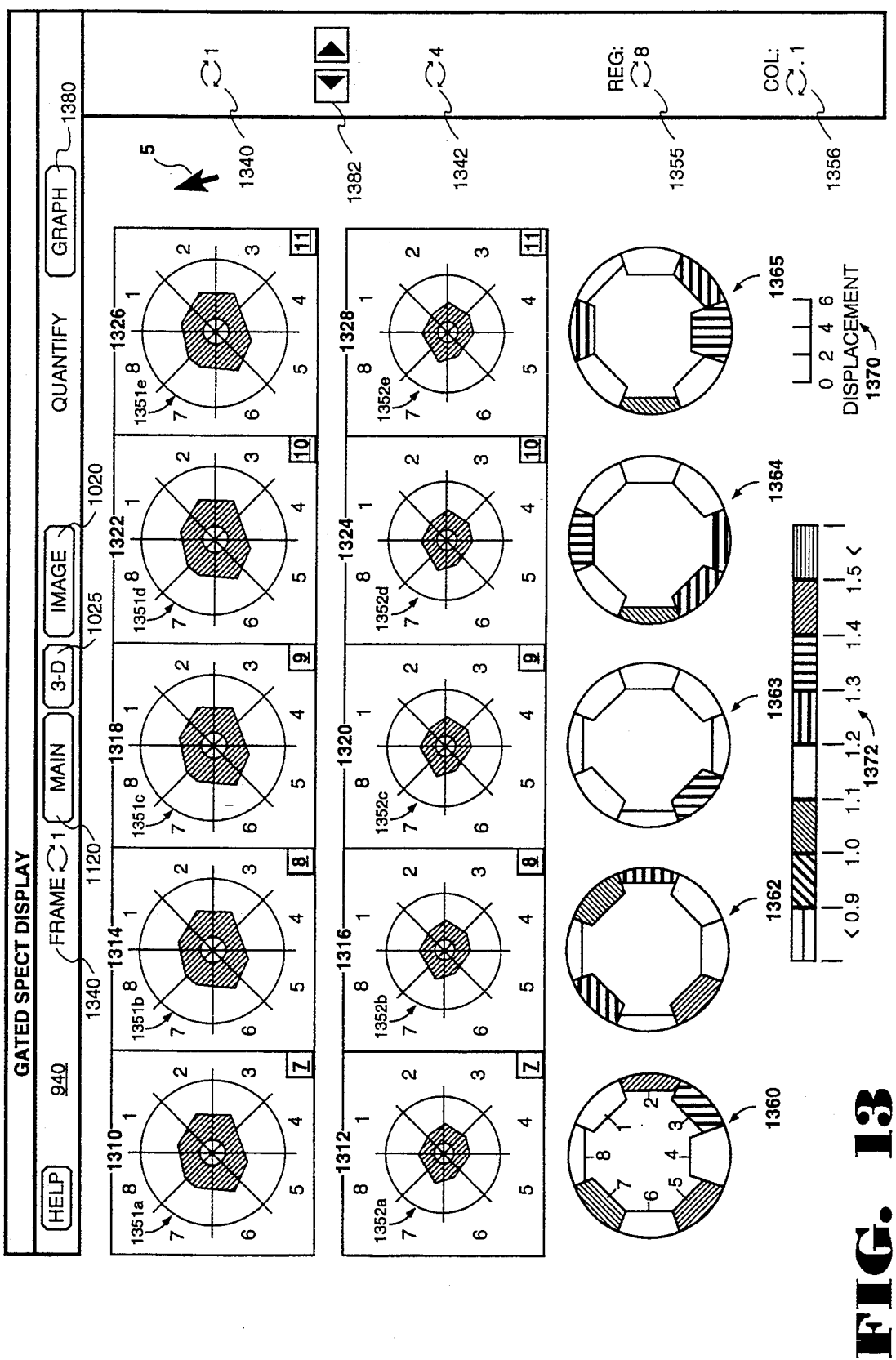
FIG. 13 illustrates the quantification ("quantify") screen and illustrates selected regions of interest (R01) and associated functional display rings of the preferred embodiment of the present invention.

The quantify screen processing 940 of the present invention may be entered from the main display screen, the image display screen and the 3D display screen. FIG. 13 illustrates a representation of the quantify display screen generated by the computer system 120 on display screen 105 as a result of the quantify processing 940. The purpose of the quantify (or quantification) screen is to provide the user with a quantitative method and display used for evaluating myocardial perfusion (wall thickening) and function (wall motion). Functional display rings are illustrated on the bottom row of FIG. 13 and these functional displays correspond to associated pairs of end-diastole and end-systole images which are displayed above the functional display rings. The functional displays are ring shaped and the ring is divided into eight particular sections which are arc sections, however the number of particular arc sections may be increased or decreased within the scope of the present invention. Each arc section is given a different color and is displayed with a different radial width depending on calculated perfusion ratios and displacement factors associated with sections of the related end-diastole and end-systole regions of interest.

The following definitions are given with respect to items of the quantify screen. The circular displays (one is shown as 1351a) that are segmented into individual pie shaped sections are called regions of interest or ROI. A particular pie shaped section is called a section of the ROI. Each viewport of the top row are frames of the end-diastole segment of the cardiac cycle (ED), and viewports of the bottom row are frames of the end-systole (ES) segment of the cardiac cycle. Each of the top row ED viewports, such as 1310, has a corresponding bottom row viewport, such as ES 1312, directly beneath. The top and bottom viewports are corresponding pairs (ES/ED) because they display the same myocardial structure (i.e., same slice frame and same short axis view) only at different segments of the cardiac cycle. Therefore, the corresponding ROIs for these related viewport images, such as 1351a and 1352a, are an ROI pair. Sections within ROI pairs are also paired, such as section 1 of 1351a and section 1 of 1352a arc section pairs because they identify the same myocardial section only at different segments of the cardiac cycle. It is appreciated, given the above, a particular functional ring presents information regarding the change of a given myocardium structure at a given slice of the reconstructed volume between the ED and ES segments.

It is noted that computations of the present invention to determine wall perfusion and wall motion (as discussed below) are performed on individual section pairs for each viewport pair. Each viewport pair (ROI pair) will render a separate functional display. Each section pair will provide information for a separate arc section of a particular functional display ring. Eight section pairs comprise all sections of a viewport pair and therefore provide all the information necessary to compute all eight arc sections of a functional display ring. It is appreciated that the ROIs, and therefore the functional displays, may be individually partitioned into any number of individual sections and that 8, or alternatively 16, sections are selected options based only on design choice. Any number of sections is therefore within the scope of the present invention.

A study of the functional displays quickly provides quantitative information regarding the amount of perfusion and wall motion for a given selected myocardial structure between the ES and ED segments. It is appreciated that ischemic areas of the myocardium will appear as areas with fair wall motion, but with little perfusion (i.e., low ratio value). This is the case because, according to the data as presented by the present invention, the wall motion image data taken during the imaging session represents a rest condition. However, the perfusion data represents a stress condition because the radionuclide is introduced and distributed while the heart is exercised and, as is well known, does not redistribute during the rest condition. Therefore, the present invention allows an efficient method of comparing rest versus stress condition data in a single functional display without the need of performing two imaging sessions, i.e., one at rest and one at stress based on the functional displays.

FIG. 13 illustrates display of a series of five images of sequential frames (1310, 1314, 1318, 1322 and 1326) from the short axis dataset for the end-diastole dataset. In the displayed instance, frame numbers 7 to 11 are displayed. It is appreciated that all of the short axis images displayed contain brightness data representative of the concentration of radionuclide within the displayed myocardium. To this extent the end-systole images (such as 1312) are somewhat brighter over the end-diastole (such as 1310) images for a normal heart. Also displayed according to the present invention beneath the above images are a series of five images (1312, 1316, 1320, 1324, and 1328) of sequential frames of the short axis dataset for the end-systole segment. In the displayed instance, frame numbers 7 to 11 are displayed. It is appreciated that images 1310 and 1312 illustrate the same myocardial structure, however image 1310 illustrates the end-diastole phase while image 1312 illustrates the end-systole phase. The same is true for the other ES/ED pairs of images (such as pair 1314, 1316 and 1318,1320, etc.). The successive images represent different short axis slices of the myocardium at end-diastole and end-systole.

It is appreciated that the following discussion centers around utilizing the ED and ES segments for analysis. However, any two reconstructed segments may be selected by a user according to the present invention. Segment selection cycle region 1340 can be used to select the segment for the upper image series display screens. Segment selection cycle region 1342 can be used to select the segment for the lower image series display screens.

Associated with each ES/ED image pair of the present invention is a separate functional display 1360, 1362, 1363, 1364, and 1365 which are displayed directly beneath the associated pairs. It is appreciated that functional display ring 1360 represents an analysis of the image data from the ES/ED pair 1310 and 1312. In order to generate a functional display, the user must first define a separate region of interest for each image of an ES/ED image pair. With reference to the viewport 1310, the user will position the cursor 5 into the center of the ventricle and active mouse 107 (i.e., the mouse 107 contains activation keys) to deposit and set the center of region of interest 1351a which will be displayed as a small dot at this stage. The computer system 120 then allows the user to move the cursor 5 to the outer edge of the ventricular wall and activate the mouse again to establish the maximum radius of the center of interest 1351a which will be displayed as a sectioned and colored circle 1351a.

The region of interest 1351a will be divided into eight equally sized pie shaped sections which are displayed in outline form and numbered 1 to 8 as shown in FIG. 13 (it is appreciated that the user can adjust the exact number of sections that divide the region of interest by activation of the region 1355 cycle field). The section numbers start at 1 and advance clockwise as shown. The user must define the region of interest in the first (leftmost) viewport for each of the two rows (i.e., for the ED and for the ES row). After the user has selected the center point and maximum radius for a region of interest, the computer system 120 computes and displays the ROI around the displayed ventricle of the image in viewport 1310 using the center and maximum radius information. The computer system 120 of the present invention then divides the circle into eight pie shaped sections of equal area. It is appreciated that activation of the mouse 107 by the user can redefine the center point and maximum radius of the region of interest (ROI) if the current ROI is not satisfactory. This action will clear the current ROI and allow the user to begin again to establish a new ROI. The present invention is also provides a mode wherein the region of interest is initially displayed and sized within a given viewport (such as viewport 1310 or 1312) and the user is allowed to displace or resize the ROI as needed. In this mode, upon display of the short axis image frame into viewport 1310, a predefined ROI is displayed and positioned in the vertical and horizontal center of viewport 1310 with a diameter of ⅔ of the length of the viewport 1310. The user may then change the position or diameter of the ROI.

The ROI requires resizing depending on the size of the short axis images displayed in viewports 1310 and 1312. The size of each ROI should be such that it outlines the edge of the myocardium displayed. Once the ROI 1351a is entered and satisfactory for the end-diastole image in the viewport 1310, the user will position the cursor 5 to the center of the ventricle in the end-systole image of viewport 1312. The present invention allows the user to define or redefine the ROI 1352a for viewport 1312 in the same fashion as described above. After the user defines the maximum radius for the second region of interest 1352a, the functional display ring 1360 can be generated and displayed. It is appreciated that the ROIs for the ED and for the ES segments will not necessarily be of the same size. The ES region of interest 1352a should be of a smaller area as compared to the ED region of interest 1351 a because the ES segment represents myocardial contraction.

Once the ROIs for the ES/ED images are selected and defined by the user, the computer system 120 computes and displays an ROI for each of the other ED images as shown 1351b to 1351e for the other four ED viewports. The computer system 120 then computes and displays the ROIs for the ES images 1352a to 1352e. It is appreciated that the user may evoke the redefine functions at any time to alter the defined regions of interest for the display images. Upon definition of the ROIs within the quantify processing the computer system 120 performs the following computations to render the functional displays 1360, 1362, 1363, 1364, and 1365 of the preferred embodiment of the present invention.

Each functional display represents perfusion and wall motion quantitative information for a particular short axis ES/ED image pair. Each section of the ROIs for the ES/ED pair have a single corresponding arc section that is combined with other arc sections to form the ring display. For a given arc section comparing ED to ES images, myocardial wall thickening information is represented by an arc color or shade while information regarding myocardial wall movement is represented by the arc section thickness or width. Since there are eight paired sections of each ROI pair, there will be eight corresponding arc sections of a particular functional display and the arcs are aligned in a circular fashion to create a ring structure. The ring structure is spatially analogous to the ROI ring format.

For example, arc section 1 of functional display 1360 represents quantitative data for the first sections of ROI 1351a and ROI 1352a. Arc section 2 of the functional display 1360 represents quantitative data for the second sections of ROI 135 la and ROI 1352a, arc 3 for the third sections, are 4 for the fourth sections and so on until are 8 of the display 1360 represents the eighth sections of the ROIs 1351a and ROI 1352a. It is appreciated that the other four functional displays, 1362–1365, are similarly created using section information from the individual ED regions of interest 1351b–1351e and section information from the individual ES regions of the interest 1352b–1352e. The color display of the functional display region 1360, as adopted by the present invention, is as follows, section1 is red, section2 yellow, section3 blue section4 red, section5 yellow, section6, section7 yellow and section8 red. The below discussions describe in more specificity the manner in which the present invention renders the functional display rings.

Although the present invention allows selection of between 8 and 16 sections per region of interest, the present invention adopts 8 sections as a default and recommended number. This is because 8 sections per region of interest is a division that yields the best statistical average for the computation of the perfusion ratio and wall movement values are that based on section pairs.

Computation of Myocardium Perfusion Ratio

For each ES/ED image or frame pair, the computer system 120 fetches the ROIs for each short axis image and the image data for the ED and the ES image. For each of the eight sections within each ROI the computer system will compare paired sections of each ROI to determine the wall thickening ratio or "perfusion ratio" for that selected section pair. For instance, the computer system 120 will analyze all of the pixels: within section1 of the ROI 1351a and will select only those pixels having a maximum count, i.e., a count value above 90% of the maximum intensity count for the pixels of Section 1 of ROI 1351a; these are the maximum intensity pixels of Section 1 ROI 1351a. The computer system 120 then determines the average of the intensities of the maximum intensity pixels; this value is called the averaged maximum pixels, and is referred to as "Ved" for the end-diastole image. The computer processor then will analyze all of the pixels within section 1 of the ROI 1352a and will select only those pixels having a count above 90% of the maximum intensity count of the pixels for Section 1 of ROI 1352a; these are called the maximum intensity pixels for Section 1 of ROI 1352a. The computer processor then will determine the average of the intensities of the maximum intensity pixels for the ES segment; this value is called the averaged maximum pixels, and is referred to as "Ves" for the end-systole image.

Therefore, the averaged maximum values are each determined by averaging all of the pixels that are above the threshold (T) of 90% of the entire intensity range of each section1 for each ROI. Specifically, Ves and Ved are determined by averaging all of the pixel intensities that exceed a value T for each respective section. The value T is computed by the present invention according to the below function:

$$T = Min + 0.9(Max - Min).$$

Where Min is the minimum intensity value of the pixels within the given section of an ROI and maximum is the maximum intensity value of the pixels within the given section of an ROI.

Once the above value is computed, the computer system 120 determines the perfusion ratio for the first section pair of the ROIs (1351a, 1352a) according to the below function:

$$\text{Ratio (section1)} = Ves/Ved.$$

The computed ratio should be larger than one for a normal heart because the contraction phase of the cardiac cycle (ES) concentrates the radionuclide and thus creates more numbers of intense pixels per unit area over the end-diastole phase. Once the perfusion ratio is determined for the particular section pair, the computer system 120 will use this ratio (typically in the range of 0.9 to 1.6) as an index into a color table that contains a different color for each 0.1 increment of ratio value. For instance, the color table utilized by the preferred embodiment of the present invention is illustrated in FIG. 13 as strip 1372. Table I below illustrates the color look-up table adopted by the preferred embodiment of the present invention.

This color scheme is adopted by the present invention because these colors provide excellent color contrast definition within the functional display rings for adjacent arc sections. A user visualizing a display ring will have no trouble associating a color of Table I with the appropriate index ratio range. This color selection is advantageous because it virtually eliminates the uncertainty of interpreting subtle changes of gray scale or other color scales currently in use. However, it is appreciated that selection of specific colors is merely a design choice and that other color schemes and color tables having high contrast definition. Also, some variable shades of the same color (or black and white shading) that provide suitable contrast adjacencies are within the scope an spirit of the present invention. In the case of color shading, the present invention employs a color shading look-up table that may be indexed by the perfusion ratio and that provides a shading value for a given color or for degrees of black and white shading.

TABLE I

| Ratio Range | Color |
|---|---|
| <0.9 | Black |
| 0.9–1.0 | Purple |
| 1.0–1.1 | Green |
| 1.1–1.2 | Red |
| 1.2–1.3 | Orange |
| 1.3–1.4 | Blue |
| 1.4–1.5 | Yellow |
| >1.5 | White |

Once the particular color is selected based on the color index as shown above and the determined ratio, the present invention instructs the computer system 120 to shade in the arc corresponding to the first section of the functional display 1360 (in FIG. 13 this is labeled as "1"). The width of the particular arc measured inward toward the circle center (or outward, if negative) from the normal circumference of the functional display 1360, is determined based on the wall motion computations as described below. The color table 1372 illustrated on the quantity display screen illustrates to the user the selected color format of use. Selection 1356 allows these colors and ratio ranges to be user defined. In some modes of operation the selections for 1355 and 1356 are not user adjustable.

It is appreciated that the above computations are performed for each of the 8 sections of the regions of interests 1351a and 1352a and therefore 8 separate arc section colors and widths are determined by the computer system 120 for each ES/ED image pair within the functional display 1360. The above process is also repeated for the remainder of the four ES/ED pairs in the analogous fashion using the ROIs of each ES/IED pair so that all five functional displays will have computed cardiac perfusion data. Once the wall motion data is determined by the present invention for each arc section, the functional displays may be rendered for observation.

Computation of Myocardium Wall Motion

The functional displays of the present invention impart information regarding wall motion of the myocardium between the end-diastole and the end-systole by varying the arc thickness of each section arc of the functional display ring. The present invention computes wall movement by determining a displacement factor (D) that is based on the displacement of the location of the center of mass (Mx, My) of the ED image and the center of mass location for the ES image for a given section pair of the ROIs. The computer system 120 performs the below computations to determine the x and y screen locations of the center of mass for a given section pair for both ED and ES image frames:

$$Mx = \frac{\text{Sum of } (Px * Pv) \text{ of all pixels } P}{\text{Total Pixel Values}}$$

Where Px and Pv are the x location and pixel count value, respectively, of pixel P.

$$My = \frac{\text{Sum of } (Py * Pv) \text{ of all pixels } P}{\text{Total Pixel Values}}$$

Where Py and Pv are the y location and pixel count value, respectively, of pixel P. According to the above equations, for a given ROI section, the total intensity (count) values for each pixel within the section are summed to yield the Total Pixel Values. The computer system 120 of the present invention then determines the sum of the function (Px*Pv) for all pixels within the given section and the sum of the function (Py*Pv) for all pixels within the given section and determines the Mx and My values according to the above division equations. The entire process is done for the ED frame section and also for the ES frame section to determine two pairs of values: $Mx_{(ed)}$, $My_{(ed)}$ and $Mx_{(es)}$, $My_{(es)}$. The coordinates for the center of mass for the ED selected section is $Mx_{(ed)}$, $My_{(ed)}$ while the coordinates for the center of mass for the ES selected section is $Mx_{(es)}$, $My_{(es)}$.

The radial distance R of each of the center of mass (Mx, My) computations to the center of the circle (Cx, Cy) of the associated ROI ring is calculated from:

$$R = \text{square root}(X*X + Y*Y)$$

Where
X=(Mx−Cx) and
Y=(My−Cy).

It is appreciated that the above computations are performed for both center of mass locations, one for ED and one for ES. Therefore, there are two circle center points as defined by coordinates (Cx, CY), one for the ED ROI and one for the ES ROI. It is appreciated that the computer processor generates two radial values from the above processing, $R_{ed}$ and $R_{es}$ where $R_{ed}$ represents the radial distance from the center of ROI 1351a to the center of mass of section 1 of 1351a and $R_{es}$ represents the radial distance from the center of ROI 1352a to the center of mass of section 1 of 1352a. It is appreciated that the radial distances R of all the sections of a given region of interest are further processed by the computer system 120 in that the computer system 120 replaces the lowest radial distance of the sections of a particular ROI by the average of the two radial values of the neighboring sections. This is an enhancement processing feature of the present invention.

The computer system 120 of the present invention then computes the displacement factor, D, for the first arc section of functional display ring 1360 according to the below equation:

$$D = R_{ed} - R_{es}.$$

The above displacement factor, D, will dictate the amount of thickness a particular ring arc will have from the circle circumference of the functional display ring. For instance, if the value of D is positive, the given arc will have a thickness of D toward the center point of the functional display ring. If the value of D is negative, then the given arc will have a thickness D extending away from the center point of the functional display ring. In either case, the color the arc area will be dictated by the particular perfusion ratio computed above for the associated section pair. It is appreciated that the computer system 120 performs the above wall motion computations for each corresponding section pair of the ES ROI 1352a and the ED ROI 1351a to generate all the arc widths for a particular functional display ring 1360. It is appreciated that the present invention displays a legend 1370 indicating the scale of the displayed wall motion displacement factor. The range is from 0 to 6 in the scale of FIG. 13.

Figure 14:
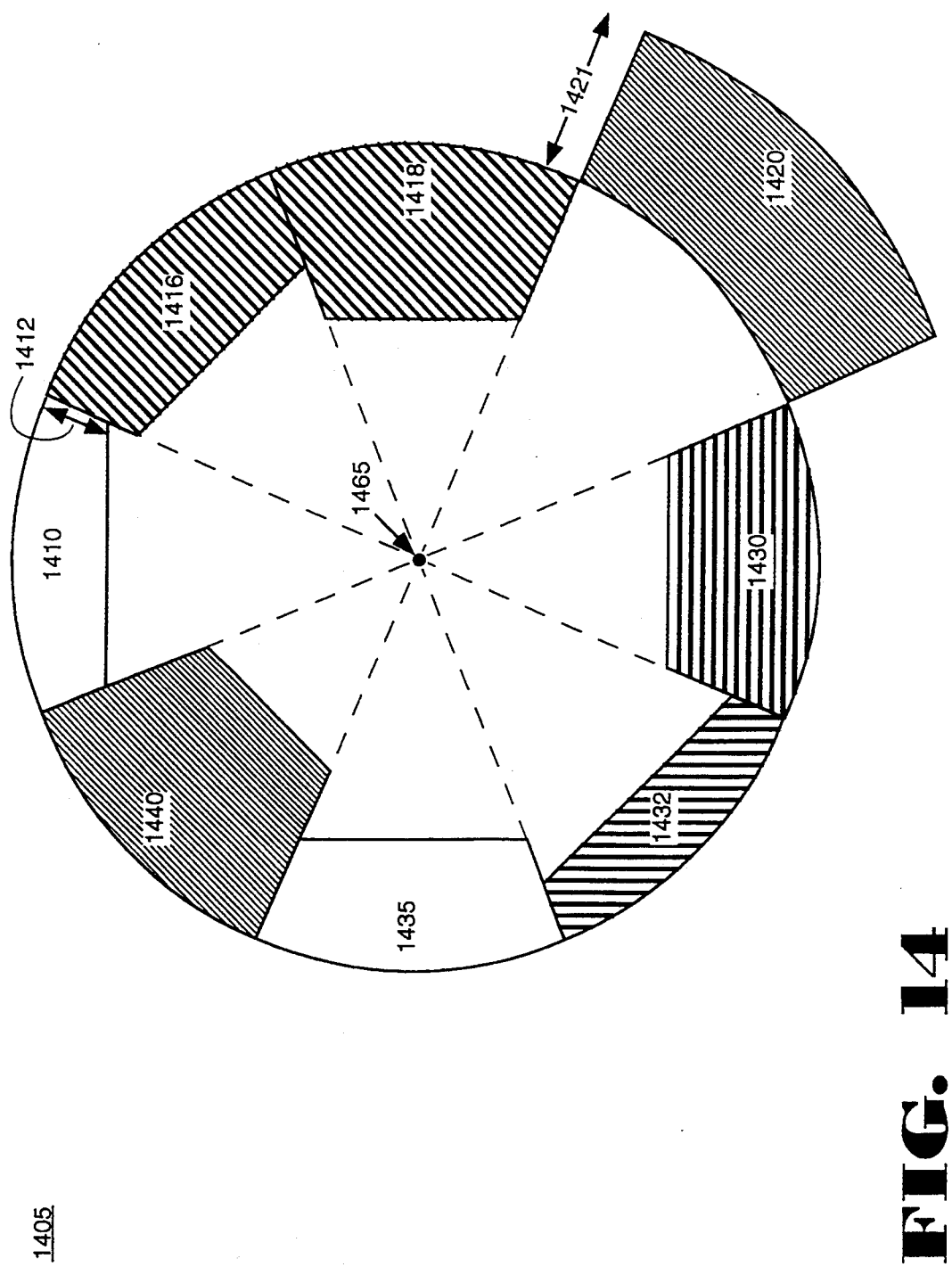
FIG. 14 is a detailed illustration of the section arcs that comprise a single functional display ring of the preferred embodiment of the present invention to illustrate wall motion thickness dimension and perfusion ratio color coding.

FIG. 14 illustrates in more detail a sample functional display ring 1405. It is appreciated that the dashed radial lines are not displayed as a part of the functional display ting, however, they are useful in identifying arc sections that are representative of specific section pairs of the regions of interest for the ED and ES images. The functional display ring consists of eight arc sections 1410, 1416, 1418, 1420, 1430, 1432, 1435 and 1440. Arc section 1410 is the first arc section and the other seven are numbered in clockwise fashion around the ring 1405. According to the present invention, the width value, indicated as distance 1412, for the section 1410 (which corresponds to the first section) is a positive value and indicates the amount of width of the are inward toward the ring center 1465. It is appreciated that the color of the are 1410 will depend on the perfusion ratio computed for the first section from the ROI data of each ED and ES image. In this example the color is red.

A positive wall motion value will thus have the thickness of the arc extended toward the center of the ring. A positive wall motion value indicates that at the end-systole phase the myocardium wall moved inward (i.e., contracted toward the center of the ventricle); this would be a normal response. A negative wall motion value will have the thickness of an arc extended away from the center 1465 of the ring. This indicates that the myocardium wall moved away from the ventricle center during end-systole. This would indicate an abnormality in most cases. FIG. 14 illustrates a negative wall movement value in arc 1420. Arc 1420 is the fourth section of the ring display 1405 and corresponds to the fourth sections of the ES/ED regions of interest. The movement value indicated by 1421 is a negative number and thus the arc: 1420 extends away from the ring center 1465. It is appreciated that the color of arc 1420 is dependent on the wall perfusion ratio computed by the relevant sections of the ES/ED region of interest. In this example arc section 1420 is green.

For purposes of illustration the following colors correspond to the eight arc sections of functional display ring 1405. Arc section 1410 is red, section 1416 is purple as well as arc section 1418, arc section 1420 is green, section 1430 is orange, section 1432 is blue, section 1435 is red and section 1440 is yellow. Integration of the wall motion are thickness and wall perfusion color coding scheme produces the functional display ring 1405 for a given ES/ED image pair. It is further appreciated that a separate functional ring is rendered for each of the five ES/ED image pairs. Each of the eight arcs of the ring 1405 may be composed of a separate color and may be of a separate width, some negative and some positive. Each pie shaped section represents a different ES/ED section pair.

The functional ring display format of the present invention, as shown in FIG. 14, is advantageous for diagnosing cardiac disease and detecting ischemic areas of the myocardium that would otherwise be falsely identified as an infarct. Suppose arc section 1416 was color coded purple and was of short width, as shown. This would indicate that the given section (section two) of the region of interest that surrounds the relevant short axis image has at least two characteristics. First, the myocardial perfusion is very low (having a low ratio) meaning the tissue did not uptake much blood when the radionuclide was introduced (i.e., under the stress condition). Second, the myocardial wall motion is very low (low width) meaning the tissue is not moving much while heart was imaged (i.e., at the rest phase during the imaging session of the present invention). This would indicate that the area of study may contain an infarct area because under both stress image computations (perfusion ration ) and rest image computations (wall movement factor) the myocardium illustrates an abnormality.

Further, using the functional display ring of the present invention, an ischemic area of the heart may also be detected which might otherwise be falsely diagnosed as an infarct. These areas are characterized as regions having poor myocardial perfusion (of the stress condition) but fair or normal wall movement (detected at the rest condition). For instance, assume region 1418 was colored coded purple which corresponds to very low perfusion ratio. However, region 1418 has good movement because the width parameter is large, meaning the myocardial tissue is moving during systole and diastole segments of the cardiac cycle. Such an area is characteristic of ischemia, where the stress condition (perfusion) illustrates the defect but the rest condition (wall motion) may or may not illustrate the problem because the myocardium functions normally at rest.

The present invention is able to detect the above condition without the necessity of taking two separate imaging sessions (i.e., one at rest and one at stress) which is a requirement of non-gated SPECT studies. Because the present invention functional display ring allows comparison of information representative of both a rest condition (imaging—wall movement) and a stress condition (radionuclide introduction time—perfusion) at the same time, the present invention offers a system for accurately and efficiently detecting false positives (i.e., false detection of infarct areas). That is, the region 1418 is not an infarct because the region moves during imaging, i.e., it has fair wall motion. The gated SPECT imaging technique of the present invention allows sampling of various segments of the cardiac cycle and can thus deliver information pertinent to the myocardium movement that non-gated SPECT studies do not provide. While other systems may predict this region as infarct because of the low perfusion ratio, the present invention functional ring display illustrates the wall motion from the gated SPECT imaging data and accurately represents that the region is better characterized as ischemic.

Functional ring displays of the present invention also provide a single quantitative display for detecting areas of radiation attenuation that may be falsely identified as infarct areas. Radiation attenuation is common in certain areas of the heart for men as a result of the diaphragm. Attenuation is also common for female patients as a result of tissues from the breast. Again, the functional displays will reveal the true nature of these areas, because while perfusion ratios may be low as a result of attenuation, wall movement may still be detected and displayed within the functional display ring.

Referring back to FIG. 13, the quantify display screen also contains useful cycle fields and other special indicators. The present invention allows any of the series of frames in the upper (ED) or lower (ES) rows to be advanced or decremented using frame advance arrows 1340 and 1342. If the advance or decrement arrow 1382 is activated, each of the short axis image frames of the ED series (i.e., 1310, 1314, 1318, 1322, 1226) and each of the ES series (1312, 1316, 1320, 1324, 1328) will increment by one or decrement by one as the case may be. It is appreciated that due to the nature of the quantitative comparison, frames of both ED and ES advance or decrement in unison. It is appreciated that the frame cycle field 1340 will control how many frames are advanced or decremented by the present invention. The region cycle field 1355 indicates the number of sections each region of interest will be divided into. The present invention allows either eight sections (as discussed above) or 16 sections for smaller sections. It is appreciated that if 16 sections are selected the corresponding functional display rings will each have 16 arc sections per ring, each section representative of ES/ED section pair. The color region 1356 indicates the particular selection of colors for the perfusion ratio color table 1372. Using cycle field 1356 different color tables and shading tables may be programmed and selected by the present invention.

Apart from the advantageous display of the functional rings of the quantify screen of the present invention, the user may cine the gated images in the first viewport of each of the series for the two displayed segments (ED and ES). This will display the entire cardiac cycle.

It is appreciated that from the quantity screen processing 940 selection of the main selection field 1120 returns processing to the main display screen. Selection of the 3D 1025 or image 1020 selection fields returns the processing to the 3D display processing or image screen processing respectively. Selection of the graph selection field 1380 transfers the user to the graph screen processing 950 (described further below). It is appreciated that the quantify screen also displays information as to the patient name, patient ID and study date.

Figure 15:
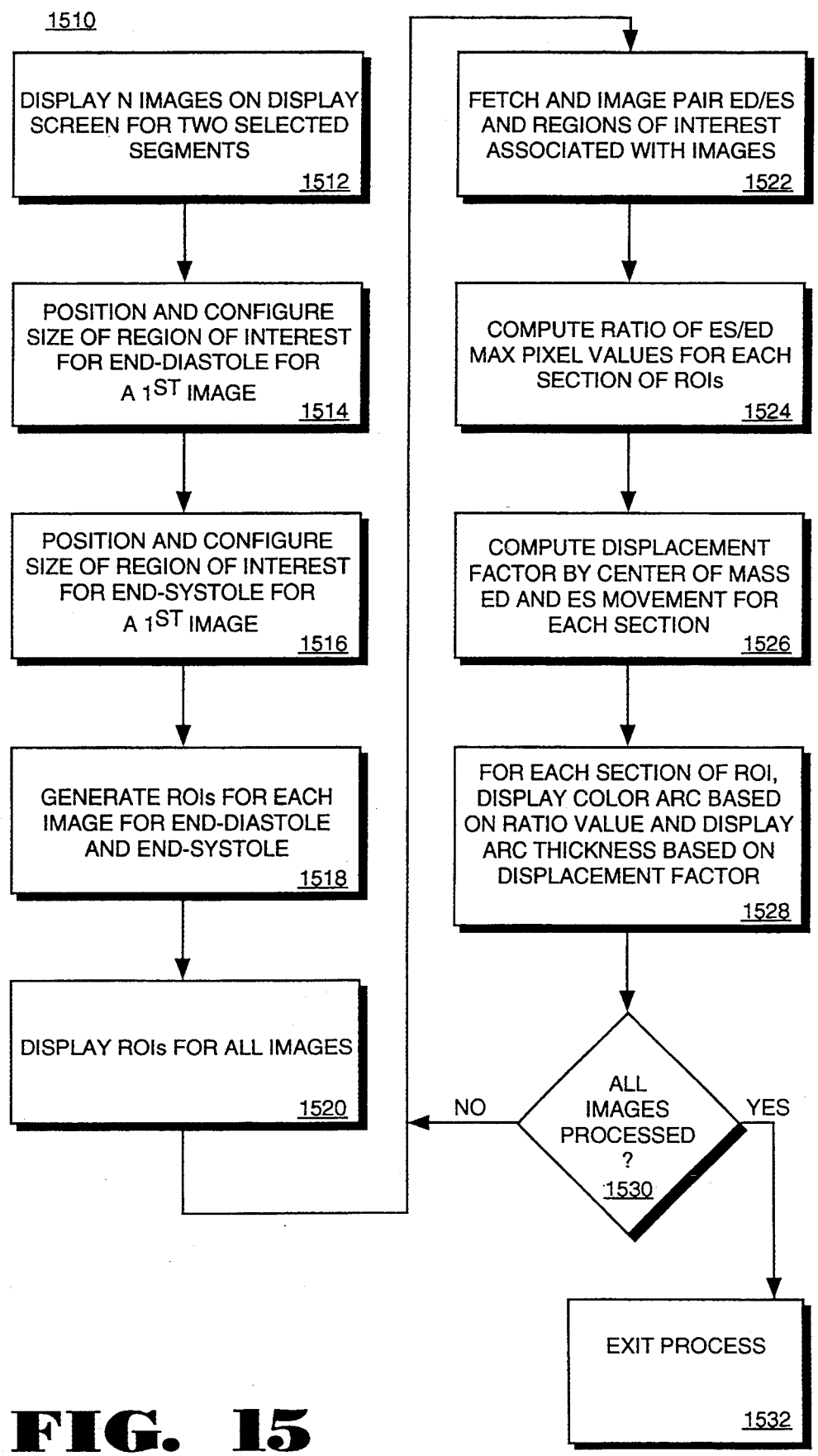
FIG. 15 is an illustration of the flow processes 1510 of the present invention used for rendering the various functional display rings of the quantify screen processing 940 of the preferred embodiment of the present invention.

FIG. 15 illustrates a detailed flow chart of the processing 1510 of the present invention used to generate and display the functional display ring images. The computer system 120, under direction of the present invention, performs the processing blocks of FIG. 15. The processing 1510 is a subset of the processing of block 940 and begins at block 1512. At block 1512 the computer system 120 displays N number of image frames on the display screen 105 of each selected segment. In the typical case the selected segments represent the ED and ES phases of the cardiac cycle. Five image frames for each segment are displayed and constitute the ED series and the ES series. Next at block 1514, the computer system 120 is instructed by the present invention to allow the user (via the cursor 5 and the mouse 107) to 5position or reposition a center point for a ROI (1351*a*) on the first short axis image (1310) of the end-diastole image frame series and to configure or reconfigure the radius of the ROI to align the circumference of the ROI with the edge of the myocardium displayed in the first ED image of the ED image frame series. At processing block 1516, the computer system 120 is instructed by the present invention to allow the user (via the cursor 5 and the mouse 107) to position or reposition a center point for a ROI (1352*a*) on the first short axis image (1312) of the end-systole image frame series and to configure or reconfigure the radius of the ROI to align the circumference of the ROI with the edge of the myocardium displayed in the first ES image of the ES image frame series. At blocks 1514 and 1516, each ROI is sectioned into 8 or 16 individual pie shaped sections.

Once the two ROIs have been defined for the first image of the ED and ES image frame series, the present invention proceeds to block 1518 where the ROIs (1351*b–h*, 1352*b–h*) are defined for each of the remainder image frames of the ED and ES image frame series. The ROIs generated in this step for the remainder frames of the ED and ES series are defined based on the placement of the ROIs in the first image frames. Next, at block 1520 the present invention displays each region of interest for every frame of the ED and ES series that are not yet displayed. At block 1522 the present invention then retrieves (fetches) from memory a first pair of ED and ES images and information regarding their respective regions of interest. The first image and ROI pair in the example of FIG. 13 represent the images within viewports 1310 and 1312.

At block 1524, the perfusion ratios for each of the eight (or 16) sections of the functional display ring are computed by the present invention using the associated section pairs from the two received regions of interest, one ED and one ES. The functions utilized to compute these perfusion ratios for each section pair are shown in discussions above. This process 1524 computes eight (or 16) perfusion ratios, one for each corresponding section pair of the ROIs. For each section pair, the process 1524 utilizes an average function to average the maximum intensity pixels for the current ED section and for the corresponding current ES section and then divides the ES result by the ED result. The perfusion ratios are then entered into a color lookup table (that may reside in memory 102) and a particular color code is assigned for each ratio (see Table I). The above is done for each of the eight section pairs for each ES/ED segment for the current functional display of the present invention.

At block 1526, the computer system 120 then computes the wall motion or displacement values for each section pair of the current functional display ring using the corresponding section pairs of the ED and ES regions of interest that were used above in the well perfusion computations. The present invention first computes the location of the center of mass for each ED section and for each corresponding ES section of the input ROIs and then computes a radial distance for each section (using the distance from the center point of the respective ROI to the computed center of mass). The computer system 120 then takes the difference of the radial distances for each section pair ES/ES and equates this value to the displacement factor for the given section; all eight section pairs (ES/ED) are processed in turn. If the radial distance of the ES section is larger than ED section for given section pair then the displacement factor takes a negative sign, otherwise the value is positive. This radial difference is computed for all associated section pairs of the ED and ES ROIs for the currently processed functional display.

At block 1528, the computer system 120 of the present invention generates the current functional display on the computer screen 105 according to the image format of FIG. 14. The computer displays all eight of the computed arc sections of the functional display ring using (1) the computed arc width for each section determined by the displacement factors of block 1526 and (2) the determined arc colors from the perfusion ratios of block 1524. All eight (or 16) arc sections are displayed in a ring format. Next at block 1530, the computer 120 checks if there are more functional displays to process. The first functional display 1360 (of FIG. 13) utilizes information from the images of viewports 1310 and 1312. If there are more ES/ED image pairs to process, the present invention will advance to the next ES/ED pair (viewports 1314 and 1316) and will return to processing block 1522 to fetch the image data for and to render the next functional display ring 1362. This process will continue in a cyclic fashion by the present invention until the last functional display ring 1365 is rendered using the data associated with viewports 1326 and 1328. At this point, the processing of block 1530 will recognize that no further functional displays are required for rendering and will flow to the exit or return processing block 1532 which returns to the general processing of block 940.

Graph Screen Processing 950

The present invention enters the graph screen processing 950 upon activation of the graph selection region 1380 from the quantify screen processing. The quantify screen processing 940 is the only entry point to the graph screen processing 950. The graph screen of the preferred embodiment of the present invention is illustrated within FIG. 16. The displays within the graph screen allow the user to graphically review the calculated perfusion ratio information in various formats. The first format 1625 is a circumferential plot of the ratios for all eight sections of a selected functional display ring. The second format 1635 is an axis plot of one single section through all image frames of the short axis data set.

Figure 16:
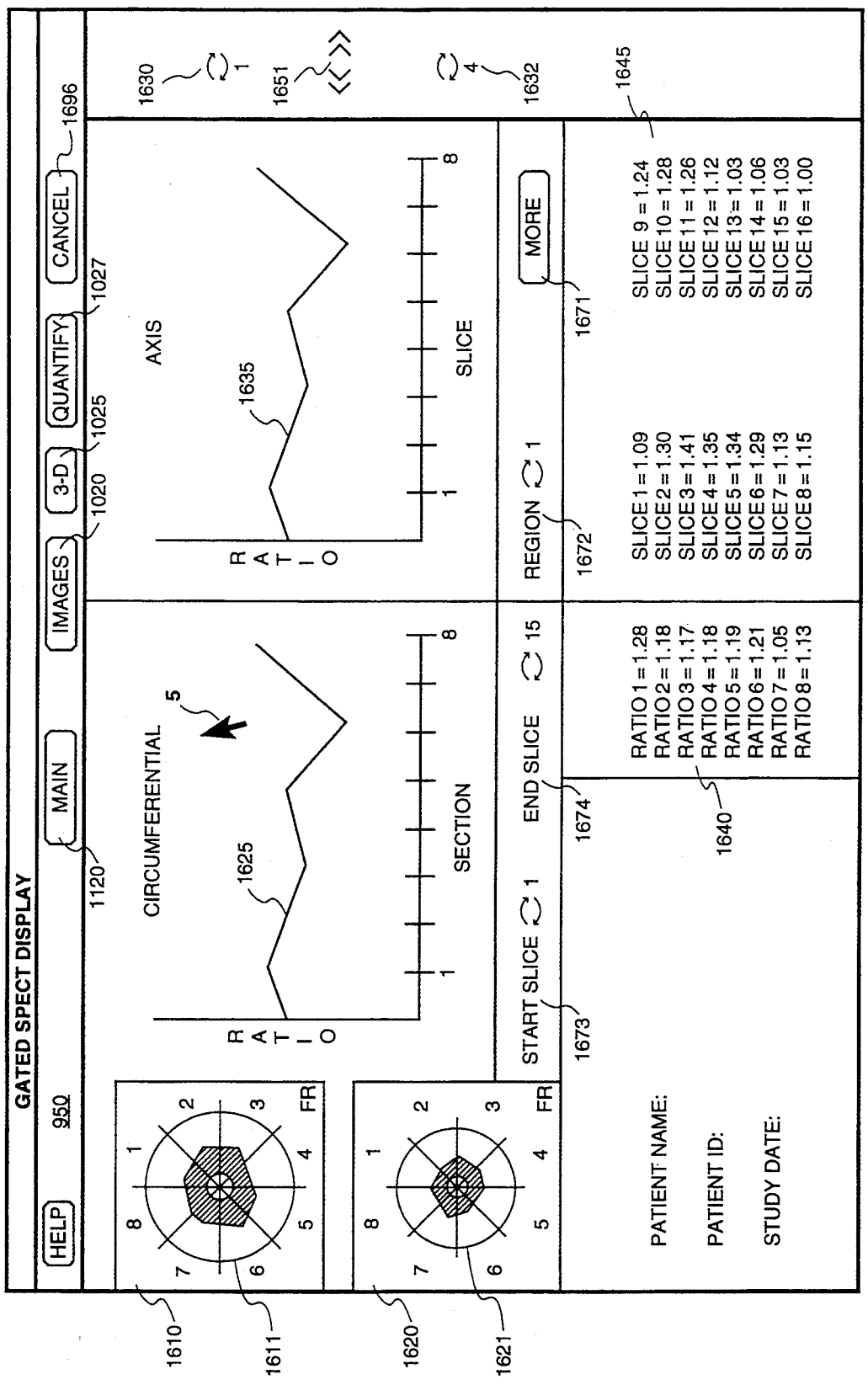
FIG. 16 illustrates the graph screen of the display processing of the present invention for numeric representation of computed perfusion ratios.

Referring to FIG. 16, there are two rows of one viewport each for display of a selected short axis frame for the ED and ES segments (or any other selected segments that have been reconstructed these are 1610 and 1620);. Each viewport displays an image with associated ROI which was defined in the quantify screen. Viewport 1610 illustrates an oblique ED image with ROI 1611 and viewport 1620 illustrates an oblique ES image with ROI 1621. These particular short axis image frames may be incremented or decremented under user control by selection of the advance and decrement arrows 1651. It is appreciated that initially the viewports 1610 and 1620 display the ROI and image data represented in viewports 1310 and 1312 of FIG. 13, respectively. If the image frames are advanced, by cursor selection of the arrow 1651, then the frame numbers in both viewports 1610 and 1620 will advance by one, or decrement by one as the case may be if the decrement arrow was selected. It is appreciated that each time the frames or decrement, the circumferential plot 1625 will change in association with the frames that are displayed. The image frames for ED and ES cannot be advanced independently, the frame number much be matched for both viewports 1610 and 1620.

The user may cine either or both of the series images (of viewports 1610 and 1620) in gated fashion with the use of cine selection regions within the present invention. If the cine function is selected, the circumferential graph will not update. When the cine is stopped, the circumferential graph 1625 updates with the frame that is displayed in the viewport. If only one of the series images is placed in cine motion and then stopped, the series image that was not in motion will advance to the frame number stopped on by the image that was in motion. For example, if viewport 1610 was in cine, viewport 1620 would remain and when viewport 1610 exited cine the frame number of 1620 would modify to the frame number of viewport 1610.

The circumferential graph 1625 plots the ratio values along the vertical and the individual sections along the horizontal for a particular functional display ring. In FIG. 16 there are only 8 sections of the functional display. This graph is a representation of the calculated ratios of all eight of the arc sections associated with one functional display ring. The maximum values for the vertical axis are the maximum ratio for all frames in the oblique set and do not change from frame to frame. The horizontal axis is the number of the pie shaped sections 1-8. Also displayed on the graph screen is a window display 1640 which displays the raw perfusion data in numeric form according to the specific eight sections. This is a numeric representation of the ratio data shown in graph 1625 and the data in the window 1640 will update whenever the graph 1625 updates.

The axis graph 1635 is a representation of calculated perfusion ratios of just one pie shaped section plotted over all of the frames in the short axis data set. This graph allows a physician to observe all the perfusion ratios for a selected section of a ROI across all short axis image frames (or "slices") of the short axis dataset for the reconstructed volume. This display can be used to default or verify suspected abnormal regions of the heart. The vertical axis maximum value of graph 1635 is the maximum ratio value for all regions for all frames. The horizontal axis represents the number of different image frames ("slices") within the short axis dataset. Only 16 slices are displayed at a time for clarity. The range of image frames may be selected using fields 1673 and 1674. More slices can be displayed in the axis graph by activation of the more region 1671. These values of the axis graph update if the user selects a different pie shaped section for display using the cursor 5. Data window 1645 illustrates the ratio data in numeric form that comprise the axis graph 1635 and this data is updated whenever the axis graph 1635 is updated.

The present invention allows some parameter modifications for the axis graph. The region cycle field 1672 is a field that allows the user to select the pie shaped section to apply to all of the frames for the axis graph 1635. The choices are from 1 to 16, depending on the number of sections for a region of interest. The start slice 1673 and end slice 1674 cycle regions allow the user to limit the number of image frames of the short axis dataset from which the ratio data will be plotted for the axis graph. The range is from 1 to n (n being the maximum of frames in the short axis or oblique data set.

Segment selectors 1630 and 1632 are not active in the graph screen. The user cannot alter the segments within the graph screen. To change these segments, the user must return to the quantify screen and select segments. If the user changes segments, then the user is required to define new ROIs for the segment. It is appreciated that the images of viewports 1610 and 1620 may be placed in cine gated motion.

Referring to FIG. 16, from the graph screen, activation of main region 1120 returns to the main screen processing 910, activation of the images region 1020 returns to the images screen processing 950, activation of the 3-D region 1025 returns to the 3-D processing 920 and activation of the quantify 1027 screen returns the user to the quantify screen processing 940 Activation of the cancel field 1696 cancels the current function and returns the user to the prior display screen processing.

The above system for image acquisition, processing and display, provides a physician a valuable tool for diagnosing cardiac disease. The functional display rings of the preferred embodiment of the present invention simultaneously provide quantitative information regarding wall perfusion and wall motion of a selected myocardium structure allowing efficient diagnosis of infarct areas and ischemic areas of the myocardium. Further, such display offers a unique method of detecting otherwise false (infarct) positives. The present invention allows the capacity to simultaneously observe image data of both stress conditions (wall perfusion) and rest conditions (wall motion) with only one imaging session, thus eliminating the requirement for a separate rest and stress imaging session. The quantitative displays of wall motion (arc width) and wall perfusion (arc color) provide the physician with valuable quantitative data for the effective diagnosis of cardiac artery disease (CAD). Further, the various display formats of the present invention offer the physician a number of qualitative analysis tools. Images can be displayed, recalled, compared and placed in cine motion for gated and SPECT image data within the present invention. In short, the preferred embodiment of the present invention provides a powerful tool for both quantitative and qualitative analysis and display of the information of the reconstructed volume of the image heart using gated SPECT imaging techniques and systems.

SECTION V

Semi-List Mode Acquisition

The computer camera system 10 (of FIG. 1) contains a computer system used for acquisition and processing of image data received from the detector 12; this computer system may be implemented within a hardware board of the computer system 110. It is understood that this computer system contains at least those elements of FIG. 2 that are indicated by block 110. To this extent there is a processor, bus, memory unit, input device, data storage device and signal input and output communication device. The camera system 10 utilizes this camera acquisition computer system to interpret and image data (data events) received directly from the imaging detector. The data that the camera acquisition computer system ("CACS") receives from the camera detector 12 is composed of a stream of words (data event words) that are approximately each 32 bits long and are communicated bit serially. Each word contains: an X coordinate store, a Y coordinate store, an energy level, a data/tag flag, and a tag code that 16 types of tags of which four represent 1) R wave time, 2) start command, 3) stop command, or ) a time tag or "tick." These event words are read by the CACS and stored in a memory unit. Data in the above form is called "list" data in "list mode" because each of the events is individually received and stored into a large listing of data in memory. The X and Y coordinate store will indicate the location of each event, if the word represents data. Also indicated, in this case, will be a representation of the energy of the detected event at the location. The energy bit will be summed with other bits at the indicated (x, y) location of a histogram (discussed below) to determine the total counts for a given (x, y) location. The data/tag bit indicates whether or not the word is data or some command tag. The R-wave time tag indicates that the word is the start of a new R wave of data, this indicates the start word of a heartbeat R—R interval dataset. The start command indicates to the CACS that an imaging session is to start. The stop command then indicates when to interrupt the imaging session. The time tag is placed into the data stream at some known interval of time, in the present invention it is introduced every millisecond; it is understood that from 4 to 6 event words may be received between each time tag. The above list is also referred to as event data in list form.

The CACS then, at some point, will take the list data and convert it into a summarized format, such as a histogram, which records the total or summation of the event data for a given X, Y coordinate. It is understood that the term "histogram" and the term "raw image" are interchangeable. The summation histogram for a given projection angle and for a given gated segment eventually is passed to the imaging system 120 for processing and reconstruction. The present invention semi-list mode acquisition is a method and mechanism to increase the efficiency and processing power of the CACS in generating the summation histogram (summation raw image) from the input data stream.

In the past, prior art camera systems would perform a first process of reading in a portion (1/10 or 1/20) of the data representing an R—R interval as data event words, parsing the words, and storing them individually into memory. The system then would then, in real-time with the above process, parse this acquired portion in a binning procedure that would, after processing several portions, create a histogram of the count information per (x, y) location for a given R—R interval of data. After the "beat histogram" was complete, the system would determine, based on the length of the R—R interval, whether the beat was accepted or rejected. If the R—R interval was rejected, the prior art system would erase the beat histogram and continue to process the next R—R interval. If accepted, the prior art system would sum the beat histogram into a summation histogram that included the (x, y) data for all accepted beats for a particular projection angle and gated segment. This system is not efficient because for bad beats the computer system must completely parse the event data to create the beat histogram, that will be ignored and erased. This is terribly inefficient. Further, the data events are parsed twice in the prior art, once for storing them into memory and a second time for binning. Also, because the prior art systems performing the binning process in real-time, they must pause receipt of data words in order to perform the summation. This means prior art systems are unable to collect 100% of the data words for an R—R interval.

Semi-List Mode Acquisition

Figure 17A:
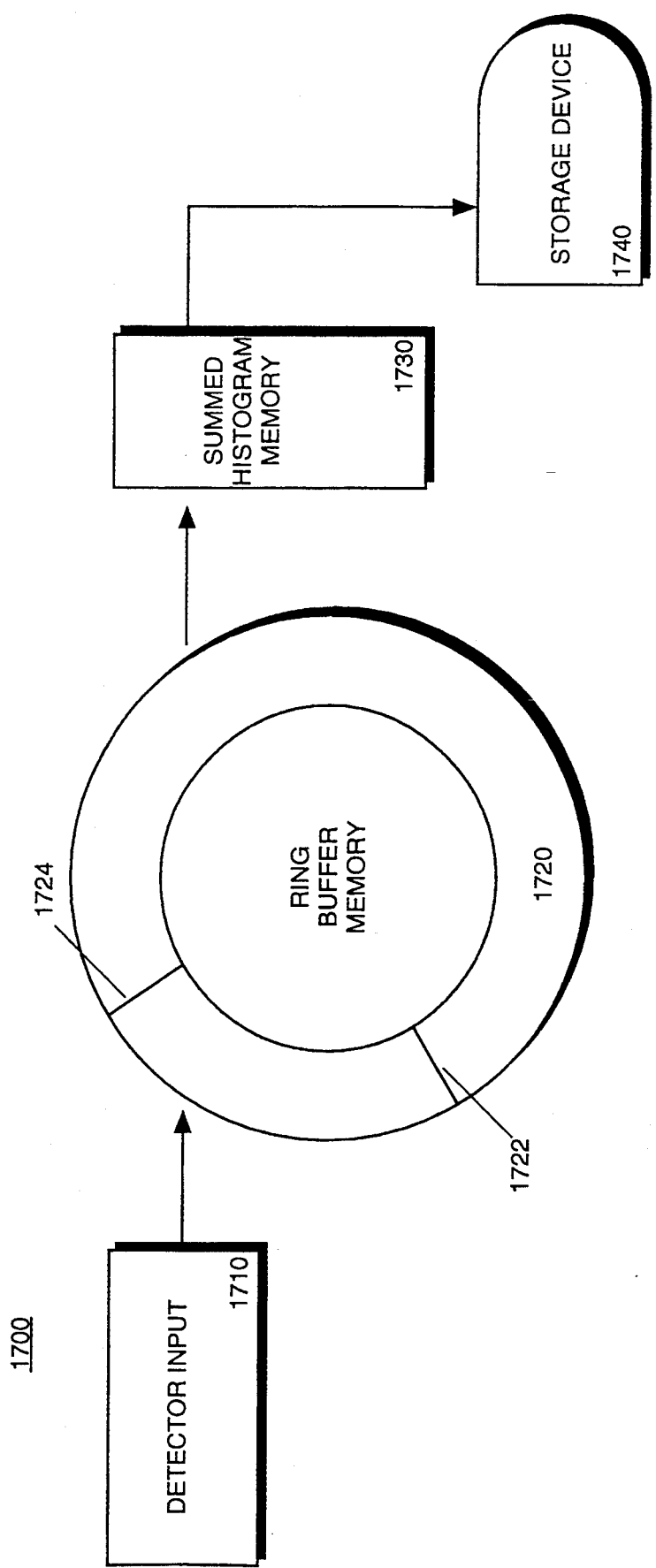
FIG. 17A is a representation of the major processing steps of the semi-list mode acquisition procedure of the present invention.

The present invention solves the above problems by providing a semi-list mode acquisition procedure that is illustrated in FIG. 17A. According to the present invention, the data event words that are received by the CACS from the detector input 1710 are stored individually into successive addresses of a ring buffer 1720 which is part of a memory unit of the CACS. The storage of the received data event words into the ring buffer is accomplished by a first process of the present invention which operates continuously in real-time. A ring buffer and buffering technique are well known in the art of computer processing and utilize a start point 1724 and an end point 1722 that may adjust around the ring buffer as data is received and processed. The ring buffer 1720 is capable of storing approximately 2 to 4 R—R intervals worth of event data. The first process of the present invention also examines the data words as they are received in order to process the tag commands that may be present within the data stream (i.e., start, stop, etc.). The first process of the present invention also detects the start of a new R—R interval and counts the time tags between successive R—R interval markers to determine the duration, in milliseconds, of a particular R—R interval. This is the duration of a given imaged heartbeat. With reference to FIG. 17A the first process of the present invention constructs the data of the ring buffer 1720.

The first process signals to the second process when an complete R—R interval worth of dam words have been received and processed by the first process. When a complete R—R interval worth of data event words are received by the first process, it will perform two very important functions. First, it stores at a memory location (start location 1764) at the beginning of the received R—R interval the address in the ring buffer of the start word of the next R—R interval that will be or has been received. Also, it records at a memory location (count location 1762) at the beginning of the received R—R interval the number of count tags detected for the received R—R interval. This information will be utilized by the second process of the present invention in order to determine when the event words for a given R—R interval dataset have been completely received by the first process.

The second process of the semi-list acquisition mode of the present invention constructs the summed histogram 1730 which is stored within a memory device of the computer system. The second process continually scans the start address of given R—R interval's set of data event words and waits until the set is completely processed by the first process. This is done either by continually polling the count location 1762 until a non-zero value is detected or by continually polling the start location 1764 until a non-zero value is detected, or both. When it is detected that the data event set for a given R—R interval is complete, the second process will perform a critical determination. It determines, based on the count number, whether or not the count for the R—R interval is within the acceptable duration window. If the count exceeds the acceptable duration then the beat is bad and the dataset of event words for the R—R interval must be rejected. The second process will then access the start location 1762 of the R—R to determine the address of the next R—R interval dataset and will go there and poll (as above) until that R—R interval's dataset is completely processed by the first process.

However, if the beat count at count location 1764 is good (i.e., within the acceptable R—R interval window) then second process will successively process each data event word in order to bin the data words of the given R—R interval into the summation histogram 1730 of FIG. 1730. Eventually, when the summation histogram 1730 is complete it will be stored in storage device 1740 and transferred to the other systems of the present invention.

It is appreciated that by providing the beat count in a predetermined location, the present invention provides a mechanism for quickly determining if a bad beat has been imaged, and if so, the second process will skip the data event words for that beat and continue on to the next R—R interval's dataset of event words. In so doing, the present invention does not waste effort in constructing a beat histogram that is never utilized. Rather, the present invention collects complete datasets (of event words) for R—R intervals and while so doing quickly keeps a running tally of the timer tags received to determine the duration of the R—R wave. There is no need, therefore, to perform the time consuming and processing intensive procedure of creating a beat histogram if the R—R duration is outside the allowable range. Only these datasets of event words of good R—R intervals are summed into the summation histogram by the second process. It is understood that the present invention is a "semi-list" data acquisition mode because it stores some data in list mode (i.e., only a few R—R intervals worth) and the remainder in history mode within the summation histogram 1730. The summed histogram is an array of 64×64 or 128×128 memory locations 16 bits deep and records counts per (x,y) location based on the event data words for R—R intervals of acceptable beat duration.

Figure 17B:
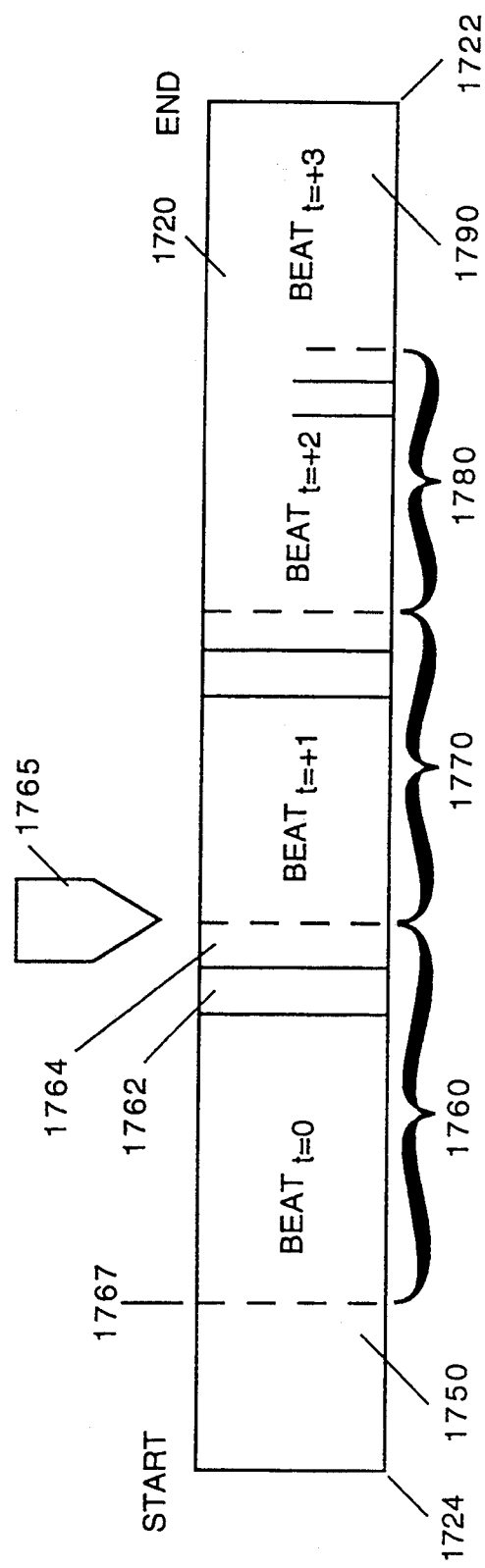
FIG. 17B is a representation of the data structure of the event words of R—R intervals stored within the ring buffer of the present invention.

FIG. 17B illustrates the structure of the ring buffer 1720 and individual event data word sets for R—R intervals. The ring buffer 1720 is shown end-to-end with memory locations of the most recently received data event words illustrated on the left. The most recently complete dataset of event words is memory string 1760 at (t=0) for reference. The dataset 1750 is not yet complete and is data events are still being recorded. A dataset becomes complete when the R-wave tag is encountered indicating a new heartbeat cycle is starting. FIG. 17B illustrates four complete R—R interval datasets 1760, 1770, 1780 and 1790. The first process is then operational near the start of the data stream 1724 because it must read, process and store the data event words as they arrive into the ring buffer in realtime. FIG. 17B also illustrates the count location 1762 and the start address location 1764 for the dataset 1760. Also illustrated is the current pointer location of the second process 1765 which is polling the start address location of dataset 1760 for a non-zero value. It is appreciated that since dataset 1760 is completely received into the ring buffer the start address location 1764 contains the address within the ring buffer of the start of the next R—R interval dataset, or point 1767. It is appreciated that the start address location and count location for dataset 1750 are both zero since the data is not yet complete. It is also understood that the second process could also be polling at the start address of dataset 1770 or 1780 or 1790 depending on the occurrence of other, previous events. That is to say, the processing of the second process is not done in real-time, but can be processing at one, two or three R—R intervals behind the first process.

If, for instance, the count value at 1762 indicated that the duration of the beat represented by dataset 1760 was bad then the second process of the CACS would skip this dataset by reading the start address from 1764 and then jumping to the address indicated by 1767 to process the next R—R interval, without generating any beat histogram. In this case since dataset 1750 is not yet complete, the second process would wait or loop until the start location or count location were non-zero. On the other hand, if the count at 1762 indicated that the R—R interval for dataset 1760 was good then the second process would individually read each of the event words and would bin the data words into the summation histogram 1730 as required. It is appreciated that the first process of the CACS already processed the commands and other tags of the dataset 1760. Assuming the second process is currently polling at dataset 1790, if it found a bad beat, it could jump to the next R—R interval 1780 and skip that one too and then process dataset 1770. Given the above flexibility of data stored in the ring buffer, the present invention semi-list mode acquisition may implement a mechanism for skipping beat information that is received before the occurrence of a bad beat. It is understood that the binning procedure of the second process of the present invention may be implemented using well known binning techniques.

Figure 17C:
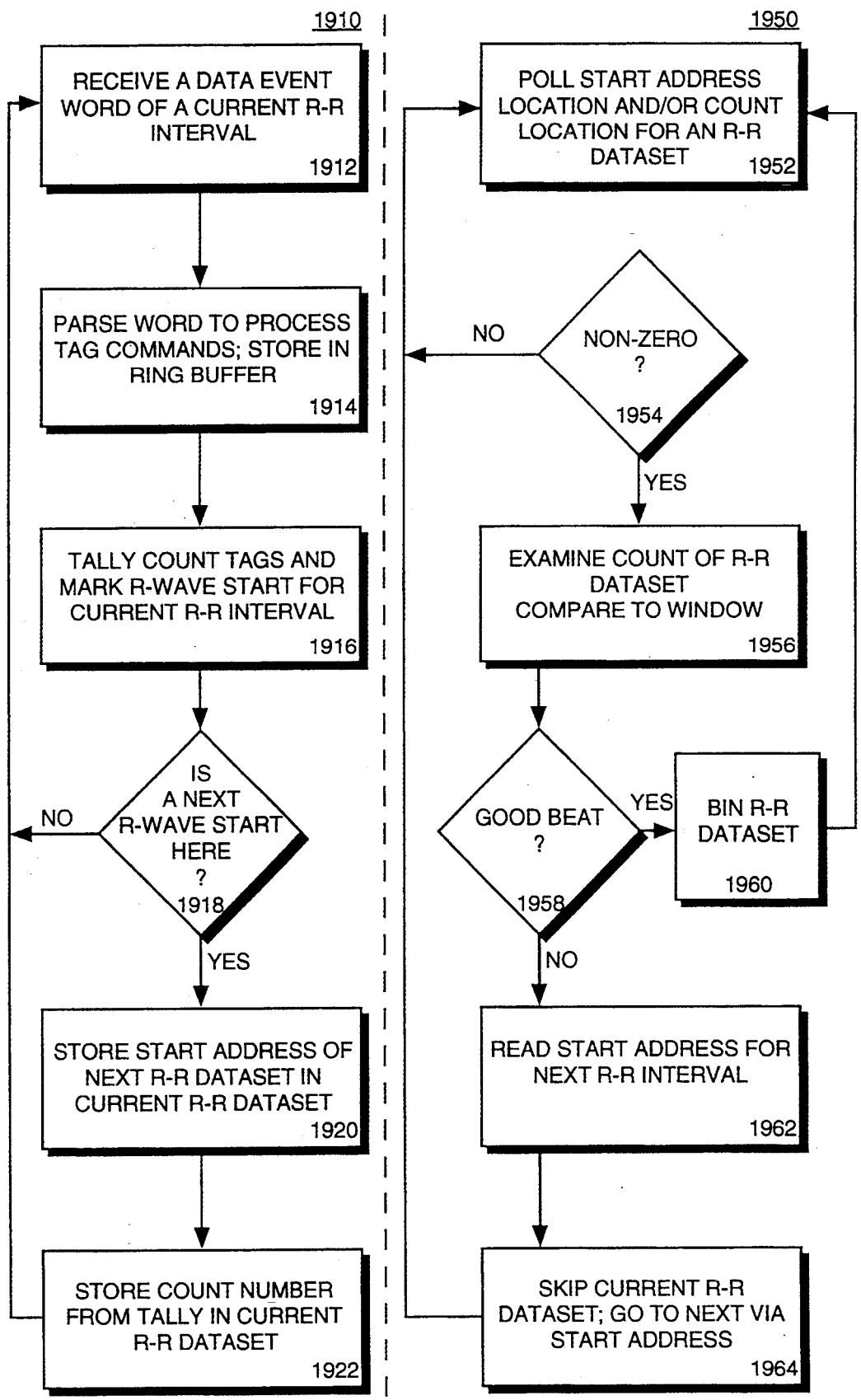
FIG. 17C is a flow diagram of the major processing blocks of the first and second processes of the semi-list mode acquisition procedure of the present invention.

FIG. 17C is a flow dial,ram illustrating major processing steps of the semi-list mode acquisition procedure of the invention. The first process 1910, as described above and implemented by the CACS, is illustrated in more detail flow diagram format. At 1912, the first process receives an event data word from the input stream from detector 12. At 1914, the received data event words are parsed by the processor of the CACS in that any tags are processed for commands and the data words are stored into the ring buffer which holds about 3 to 4 R—R intervals worth of data event words. At 1916, the processor will tally the number of timer count tags received since the last R-wave tag in order to time the duration of the current R—R interval; the start of a new R-wave is also indicted here. At 1918, the processor checks a new R-wave tag is located. If not, the processor returns to 1912 to continue processing and storing data event words into the ring buffer 1720 for the current R—R interval dataset.

At block 1920, the processor determined that a new R-wave tag was discovered. The processor then marks the start address of the ring buffer of where the next R—R interval dataset will begin. At 1922, the: processor then stores the summation of the timer count tags received for the current R—R interval dataset and returns to 1912 to collect this next dataset. At this point the current R—R dataset is complete and may be parsed by the second process 1950. The first process 1910 operates in real-time.

The second process 1950 of the present invention does not function in real-time but may process R—R interval datasets that were previously received by 1910. At 1952, the second process polls the start address and/or the count value (as stored by 1920 and 1922) of a previously processed R—R dataset from the first process. At 1954, if these values are zero then the processor returns to 1952. If the values are not zero then the R—R interval dataset is complete and ready for the second process 1950. At 1956, the second process examine the count value to determine if the value is within the allowable window and the beat is compared at 1958. If the beat is good, then at 1960, the entire R—R interval dataset is binned into the summation histogram 1730 for all valid data for binning. Still at 1960, then the R—R interval dataset is reset and the start address is read for the next R—R interval data and the process returns to 1952.

If the beat was determined bad (outside the window) at 1958, then at 1962 the second process will read the start address of the next R—R interval dataset (as stored by 1920). At 1964, the second process will skip the current bad R—R interval dataset, without creating any histogram binning, and will jump to that start location within the ring buffer and enter block 1952. By eliminating the binning of step 1960 at this point the present invention operates efficiently.

In sum, by providing a first processing system that inputs the data events in realtime and records 1) the number of counts received and 2) the start address within the ring buffer of the next R—R interval, the present invention provides the binning process (the second process) with a mechanism for skipping bad beats. The second process does not perform the time consuming process of generating a beat histogram of a bad beat, but rather, only processes good beats into the summation histogram 1730. Although the memory requirements for the ring buffer 1720 are approximately equivalent to the memory requirements of the prior art beat histogram, the present invention does offer a vast increase in processing speed (about three time faster) over prior art parsing systems. Further, since the binning process of the present invention is not accomplished in real-time, like the prior art systems, the present invention may gather 100% of the R—R interval because it does not have to pause receipt of the data events in order to bin.

Figure 18:
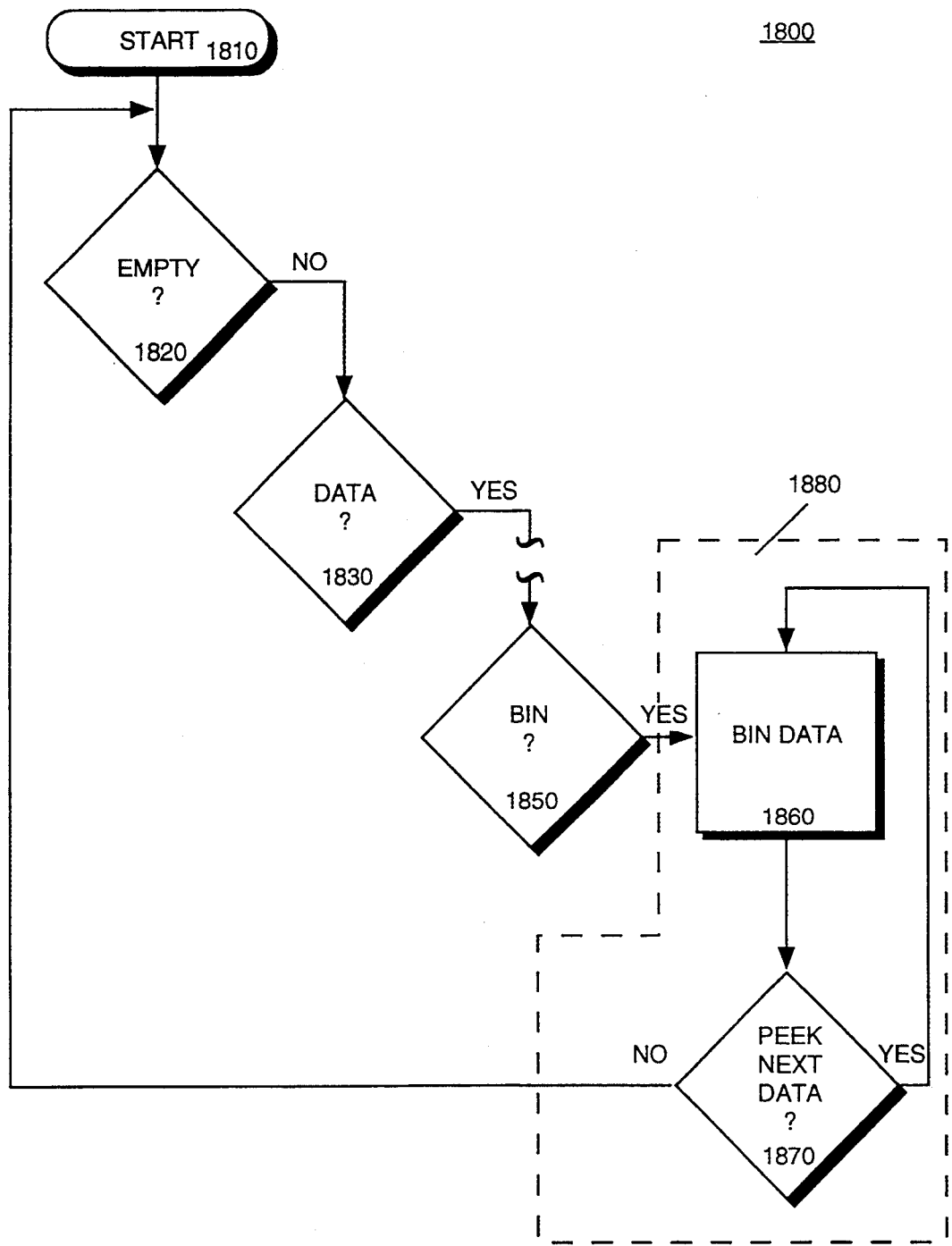
FIG. 18 is a flow diagram of the steps of the binning process of the present invention.

FIG. 18 illustrates a flow diagram of the binning procedure 1800 of the present invention which is the same process as block 1960 (of FIG. 17C). The binning procedure first examines each data word of a good R—R intervals dataset to determine if the data word has data or is empty at state 1820. If the data word is not empty then the computer checks if the data word represents data or a tag; this is done at block 1830. If the data word represents pixel data then the process performs a number of other various checks that are not pertinent to the present invention. If these series are successful the flow reaches block 1850 where the computer determines if binning is required based on the presence of valid data for binning. If so, the process flows to block 1860 where the valid data word is binned into the summation histogram 1730. In prior art systems the process would then flow back to block 1820 to retrieve a new data word. However, the present invention advantageously assumes that since the current data word contains valid data that needed to be binned, the next data word may also have valid data to be binned. This is usually the case since tags are relatively infrequent within the data stream of event words. Therefore, the present invention at block 1870 peeks at the status of the next data word (this is entirely possible because the ring buffer 1720 of the present invention contains the data words for an entire R—R interval) and if this next data word is data then the present invention loops directly back to block 1860 to bin the data. If the test fails at block 1870 then the present invention loops back to block 1820.

It is understood that by not automatically returning to block 1820 after completion of the processing step 1860 the present invention eliminates the need to redundantly execute the parsing steps 1820, 1830 and 1850 (and others) when consecutive data words are encountered that contain data for binning. On the down side an extra condition (block 1870) is imposed within the binning process of the present invention. However, since tags are relatively infrequent within the overall data stream, the time required to execute this extra condition is far outweighed by the same saved by avoiding the other, preliminary, parsing steps. It is also noted that each of the instructions within block 1880 may be placed within an instruction cache memory to further increase the operational speed of the binning process when the invention receives consecutive data words having data for binning. The binning process will then only exit the cache memory upon detection of a tag within detection block 1870.

The preferred embodiment of the present invention, a computer implemented system for image acquisition, processing and display of nuclear medicine images, including functional displays simultaneously presenting quantitative display information regarding perfusion and function and semi-list mode data acquisition capability, is thus described. While the present invention has been described in particular embodiments, it should be appreciated that the present invention should not be construed as limited by such embodiments, but rather construed according to the below claims.

What is claimed is:

1. An apparatus for displaying information used in diagnosing heart disease, said apparatus comprising:
   a processor controlled first display means for displaying a graphical representation of myocardial perfusion for a selected section of myocardium, said representation of said myocardial perfusion displayed in a first area;
   a processor controlled second display means for displaying a graphical representation of myocardial wall movement for said selected myocardium section, said representation of said myocardial wall movement displayed in said first area;
   a processor coupled to control said first and second display means for receiving information detected from said selected section of myocardium, said processor also for computing myocardial perfusion ratios and myocardial wall movement for said selected section of myocardium: and
   said first and said second display means simultaneously displaying said respective myocardial perfusion and said myocardial wall movement graphical representations on a display screen.

2. An apparatus for displaying information as described in claim 1 wherein said myocardial perfusion is represented graphically as a perfusion ratio and wherein said graphical representation of said myocardial perfusion is a color value that is provided from a color lookup table indexed by said perfusion ratio computed by said processor and wherein said first area adopts said color value.

3. An apparatus for displaying information as described in claim 1 wherein said processor further comprises means for displaying a graphical representation of perfusion ratios for individual subsections of said selected section of myocardium for each of a plurality of dataframes within a dataset.

4. An apparatus for displaying information as described in claim 1 wherein said graphical representation of said myocardial wall movement is a width of said first area.

5. An apparatus for displaying information as described in claim 1 wherein:
   said myocardial perfusion is represented graphically as a perfusion ratio and wherein said graphical representation of said myocardial perfusion is a color value that is provided from a color lookup table indexed by said perfusion ratio and wherein said first area adopts said color value; and wherein said graphical representation of said myocardial wall movement is a width of said first area.

6. An apparatus for displaying information as described in claim 5 wherein said first area is an arc section of a functional display ring comprised of a plurality of arc sections and wherein each arc section of said plurality of arc sections displays myocardial perfusion and wall movement graphical representations for a different selected section of myocardium.

7. An apparatus for displaying information as described in claim 5 and further comprising:
   an acquisition processor;
   a memory unit coupled to said acquisition processor;
   at least one detector unit for detecting image events and for supplying image information for storage into said memory Unit; and
   a second processor coupled to said memory unit, said second processor for parsing said image events wherein:
   (i) said second processor is for receiving individual data event words for an entire R—R interval to form a current data event word set;
   (ii) said second processor is for storing said data event words in list form for an entire R—R interval in a buffer of said memory unit; and
   (iii) said second processor is for indicating, within unique locations with said current data event set, a start address for a subsequent data event word set and a count number representative of the duration of said R—R interval of said current data event word set.

8. An apparatus for displaying information as described in claim 1 wherein said first area is an arc section of a functional display ring comprised of a plurality of arc sections.

9. An apparatus for displaying quantitative information used in diagnosing heart disease, said information based on images of a tomographically reconstructed volume of the heart, said apparatus comprising:
- a selector responsive to a user input for selecting a selected section of myocardium;
- a processor for computing a myocardial perfusion ratio for said selected section of myocardium;
- said processor also for computing a wall movement factor for said section of myocardium;
- a display device coupled to said processor for displaying both a quantitative graphical representation of said myocardial perfusion ratio and a quantitative graphical representation of said myocardial wall movement factor in a first area of said display device wherein said first area is associated with said selected section of myocardium.

10. An apparatus for displaying quantitative information as described in claim 9 wherein said quantitative representation of said myocardial perfusion ratio is a color or a color shade that is provided from a lookup table indexed by said perfusion ratio and filled into said first area.

11. An apparatus for displaying quantitative information as described in claim 10 wherein said quantitative representation of said myocardial wall movement factor is a width of said first area.

12. An apparatus for displaying quantitative information as described in claim 9 wherein said first area is an arc section of a functional display ring comprised of a plurality of arc sections.

13. An apparatus for displaying information as described in claim 12 wherein said first area is an arc section of a functional display ring comprised of a plurality of arc sections and wherein each arc section of said plurality of arc sections displays a representation of a myocardial perfusion ratio and a wall movement factor for an individual section of said selected section of myocardium.

14. An apparatus for presenting quantitative image information used for diagnosing heart disease, said quantitative image information based on data obtained using gated SPECT techniques, said apparatus comprising:
- a display system displaying a first image of a myocardial structure during diastolic phase of a cardiac cycle;
- said display system also displaying a second image of said myocardial structure during systolic phase of said cardiac cycle;
- a selection device for selecting a region of interest of said first image and also for selecting a region of interest of said second image;
- a processor coupled to communicate to said display system and to said selection device, said processor for computing perfusion ratios and wall movement factors for individual sections of said myocardial structure defined by said regions of interest; and wherein
- said display system also displaying a functional ring representative of said myocardial structure, said functional ring comprising graphical representations of both said perfusion ratios and said wall movement factors for said individual sections of said myocardial structure.

15. An apparatus for presenting quantitative image information used for diagnosing heart disease as described in claim 14 wherein said first and second images of said myocardial structure are slices of tomographically reconstructed volumes of the head: at diastole and systole, respectively.

16. An apparatus for presenting quantitative image information used for diagnosing heart disease as described in claim 15 wherein said slices are image frames of a short axis orientation.

17. An apparatus for presenting quantitative image information used for diagnosing heart disease as described in claim 14 wherein said region of interest of said first image and said region of interest of said second image are each divided into a plurality of individual sections and wherein a section pair comprises sections of each region of interest that correspond to a same portion of said myocardial structure.

18. An apparatus for presenting quantitative image information used for diagnosing heart disease as described in claim 17 wherein said regions of interest are each divided into a number of pie shaped sections of equal area.

19. An apparatus for presenting quantitative image information used for diagnosing heart disease as described in claim 18 wherein said number of pie shaped sections is 8 or 16.

20. An apparatus for presenting quantitative image information used for diagnosing heart disease as described in claim 17 further comprising a memory device coupled to said processor and wherein:
- said processor is also for computing a first average by averaging maximum intensity pixels within a first section of a section pair;
- said processor is also for computing a second average by averaging maximum intensity pixels within a second section of said section pair; and
- said processor is also for computing a perfusion ratio for said section pair by dividing said first average by said second average, said processor also for storing said perfusion ratio into said memory device.

21. An apparatus for presenting quantitative image information used for diagnosing heart disease as described in claim 17 further comprising a memory device coupled to said processor and wherein:
- said processor is also for computing a location of a first center of mass for a first section of a section pair;
- said processor is also for computing a location of a second center of mass for a second section of said section pair; and
- said processor is also for computing said wall movement factors based on the difference of radial distances between said first center of mass and said region of interest of said first image and said second center of mass and said region of interest of said second image, said processor also for storing said wall movement factors into said memory device.

22. An apparatus for presenting quantitative image information used for diagnosing heart disease as described in claim 17 wherein said display system further comprises a display screen and wherein:
- said processor controls said display system to display a plurality of arc sections on said display screen comprising said functional display ring, wherein each arc section corresponds to an individual section pair;
said processor controls said display system to display coloring in individual arc sections depending on a perfusion ratio for said each arc section; and
said processor controls said display system to display a varying radial width of said each arc section depending on a wall movement factor for said each arc section.

23. An apparatus for presenting quantitative image information used for diagnosing heart disease as described in claim 14 further comprising a memory device coupled to said processor and wherein:
said processor is also for computing said wall movement factors by computing average maximum pixel intensity values for sections of said region of interest of said first image and for sections of said region of interest of said second image; and
said processor is also for computing said perfusion ratios by dividing said average maximum pixel intensity values of corresponding sections of the same myocardial structure, said processor also for storing said perfusion ratios and said wall movement factors into said memory device.

24. An apparatus for presenting quantitative image information used for diagnosing heart disease as described in claim 14 further comprising a memory device coupled to said processor and wherein:
said processor is also for computing centers of mass for sections of said region interest of said first image and for sections of said region of interest of said second image; and
said processor is also for computing said wall movement factors by computing displacements of centers of mass relative to said regions of interest for corresponding sections of a same myocardial structure, said processor also for storing said wall movement factors into said memory device.

25. An apparatus for presenting quantitative image information used for diagnosing heart disease as described in claim 14 wherein representations of said perfusion ratios utilize color coding and wherein said representations of said wall movement factors utilize variable widths.

26. An apparatus for presenting quantitative image information used for diagnosing heart disease as described in claim 14 wherein said display system further comprises a display screen and wherein:
said processor controls said display system to display a plurality of arc sections on said display screen comprising said functional display ring;
said processor controls said display system to display coloring in individual am sections depending on a perfusion ratio for said each arc section; and
said processor controls said display system to display a varying radial width of said each arc section depending on a wall movement factor for said each arc section.

27. An apparatus for presenting quantitative image information used for diagnosing heart disease, said quantitative image information based on data obtained using gated SPECT techniques, said apparatus comprising:
means for displaying a first image of a myocardial structure during diastolic phase of a cardiac cycle;
means for displaying a second image of said myocardial structure during systolic phase of said cardiac cycle;
means for selecting a region of interest of said first image and also for selecting a region of interest of said second image, said region of interest of said first image and said region of interest of said second image each divided into a plurality of individual sections and wherein a section pair comprises sections of each region of interest that correspond to a same portion of said myocardial structure;
means for computing perfusion ratios and wall movement factors for individual sections of said myocardial structure defined by said regions of interest; and
means for displaying a functional ring representative of said myocardial structure, said functional ring comprising a plurality of arc sections color coded for representing perfusion ratios and of variable radial width for representing wall movement factors.

28. An apparatus for presenting quantitative image information used for diagnosing heart disease as described in claim 27 wherein said first and second images of said myocardial structure are short axis slices of tomographically reconstructed volumes of the heart at diastole and systole respectively.

29. An apparatus for presenting quantitative image information used for diagnosing heart disease as described in claim 27 wherein said means for computing perfusion ratios and wall movement factors comprises:
means for computing a first average by averaging maximum intensity pixels within a first section of a section pair;
means for computing a second average by averaging maximum intensity pixels within a second section of said section pair; find
means for computing a perfusion ratio for said section pair by dividing said first average by said second average.

30. An apparatus for presenting quantitative image information used for diagnosing heart disease as described in claim 29 wherein said means for computing perfusion ratios and wall movement factors comprises:
means for computing a first center of mass for a first section of a section pair;
means for computing a second center of mass for a second section of said section pair; and
means for computing said wall motion factor based on the difference of radial distances between said first center of mass and said region of interest of said first image and said second center of mass and said region of interest of said second image.

31. An apparatus for presenting quantitative image information used for diagnosing heart disease as described in claim 27 wherein said means for displaying a functional ring representative of said myocardial structure comprises:
means for displaying a plurality of arc sections comprising said functional display ring, wherein each arc section corresponds to an individual section pair;
means for coloring each arc section depending on a perfusion ratio for said each arc section; and
means for varying radial width of said each arc section depending on a wall movement factor for said each arc section.

32. A system for processing and displaying image information acquired by a nuclear camera system using gated SPECT imaging techniques, said system comprising:

(a) bus means for providing communication, a central processor means coupled to said bus means for processing instructions and commands, a display means coupled to said bus means for displaying information, a memory means coupled to said bus means for storing information, an input means coupled to said bus means for user interface;

(b) means for tomographically reconstructing image data acquired from said gated SPECT nuclear camera system; and (c) means for displaying information based on said reconstructed image data, said means for displaying comprising:

means for displaying a first image of a myocardial structure during diastolic phase of a cardiac cycle;

means for displaying a second image of said myocardial structure during systolic phase of said cardiac cycle;

means for selecting a region of interest of said first image and also for selecting a region of interest of said second image;

means for computing perfusion ratios and wall movement factors for individual sections of said myocardial structure defined by said regions of interest; and means for displaying a functional ring representative of said myocardial structure, said functional ring comprising representations of both said perfusion ratios and said wall movement factors of said individual sections of said myocardial structure.

33. A system for processing and displaying image information acquired by a nuclear camera system using gated SPECT imaging techniques as described in claim 32 wherein said region of interest of said first image and said region of interest of said second image are each divided into a plurality of individual sections and wherein a section pair comprises sections of each region of interest that correspond to a same portion of said myocardial structure.

34. A system for processing and displaying image information acquired by a nuclear camera system using gated SPECT imaging techniques as described in claim 33 wherein said regions of interest are each divided into a number of pie shaped sections of equal area.

35. A system for processing and displaying image information acquired by a nuclear camera system using gated SPECT imaging techniques as described in claim 33 wherein said means for computing perfusion ratios and wall movement factors comprises:

means for computing a first average by averaging maximum intensity pixels within a first section of a section pair;

means for computing a second average by averaging maximum intensity pixels within a second section of said section pair; and means for computing a perfusion ratio for said section pair by dividing said first average by said second average.

36. A system for processing and displaying image information acquired by a nuclear camera system using gated SPECT imaging techniques as described in claim 33 wherein said means for computing perfusion ratios and wall movement factors comprises:

means for computing a first center of mass for a first section of a section pair;

means for computing a second center of mass for a second section of said section pair; and means for computing said wall motion factor based on the difference of radial distances between said first center of mass and said region of interest of said first image and said second center of mass and said region of interest of said second image.

37. A system for processing and displaying image information acquired by a nuclear camera system using gated SPECT imaging techniques as described in claim 33 wherein said means for displaying a functional ring representative of said myocardial structure comprises:

means for displaying a plurality of arc sections comprising said functional display ring, wherein each arc section corresponds to an individual section pair;

means for coloring each arc section depending on a perfusion ratio for said each arc section; and means for varying radial width of said each arc section depending on a wall movement factor for said each arc section.

38. A computer implemented method for rendering information used in diagnosing heart disease on a display screen, said method comprising the computer implemented steps of:

selecting a myocardium section from a tomographically reconstructed volume;

determining myocardial perfusion and myocardial wall movement of said selected myocardium section;

displaying in a first area on said display screen a representation of said myocardial perfusion for said selected section of myocardium; and displaying simultaneously in said first area a representation of said myocardial wall movement for said selected myocardium section.

39. A computer implemented method for rendering information as described in claim 38 wherein said step of determining comprises the steps of:

determining a perfusion ratio for said selected myocardium section; and determining a wall displacement factor for said selected myocardium section.

40. A computer implemented method for rendering information as described in claim 39 wherein said step of displaying said myocardial perfusion comprises the step of filling said first area with a color value corresponding to said perfusion ratio.

41. A computer implemented method for rendering information as described in claim 39 wherein said step of displaying said myocardial perfusion ratio comprises the step of filling said first area with a color shade value corresponding to said perfusion ratio.

42. A computer implemented method for rendering information as described in claim 39 wherein said step of displaying said myocardial wall movement comprises the step of assigning and displaying a width of said first area according to said wall displacement factor.

43. A computer implemented method for rendering information as described in claim 39 wherein said step of displaying said myocardial perfusion comprises the step of filling said first area with a color shade value corresponding to said perfusion ratio and wherein said step of displaying said myocardial wall movement comprises the step of assigning and displaying a width of said first area according to said wall displacement factor.

44. A computer implemented method for rendering information as described in claim 38 wherein said first area is an arc section of a functional display ring comprised of a plurality of arc sections.

45. A computer implemented method for displaying information as described in claim 43 wherein said first area is an arc section of a functional display ring comprised of a plurality of arc sections and further comprising the step of displaying myocardial perfusion and wall movement representations for a different selected section of myocardium in each arc section of said plurality of arc sections.

46. A computer implemented method for displaying information used in diagnosing heart disease on a display device, said method comprising the computer implemented steps of:
    acquiring a raw gSPECT image dataset, said raw gSPECT image dataset comprising data configured by projection angle and gated in segments across a cardiac cycle;
    processing said raw gSPECT image dataset to produce a tomographically reconstructed volume for each gated segment; and
    displaying on said display device a plurality of section arcs coupled together to form a functional display ring based on a particular slice of said reconstructed volume, said step of displaying a plurality of section arcs comprising the steps of:
        filling each arc section with a color depending on a perfusion ratio for said each arc section; and
        adjusting a width of said each arc section based on a wall motion factor for said each arc section.

47. A computer implemented method for displaying information used in diagnosing heart disease on a display device as described in claim 46 further comprising the computer implemented steps of:
    displaying an ED slice of image data from a reconstructed volume for an end-diastole segment;
    selecting an ED region of interest for said ED slice of image data, said ED region of interest comprising ED sections;
    displaying an ES slice of image data from a reconstructed volume for an end-systole segment;
    selecting an ES region of interest for said ES slice of image data, said ES region of interest comprising ES sections wherein individual ED sections and individual ES sections comprise section pairs;
    computing a perfusion ratio for each section pair of said ED and ES regions of interest based on dividing averaged maximum pixel intensities for pixels of said each section pair; and
    computing a wall movement factor for each section pair of said ED and ES regions of interest based on displacements of centers of mass for said pixels of said each section pair.

48. A computer implemented method for displaying information used in diagnosing heart disease on a display screen, said information obtained using gated SPECT imaging techniques and tomographic reconstruction procedures, said method comprising the computer implemented steps of:
    receiving a computed ratio for myocardial perfusion for a selected section of myocardium;
    receiving a computed wall movement factor for myocardial wall movement for said selected section of myocardium;
    displaying in a first area on said display screen a color representation of said myocardial perfusion ratio for said selected section of myocardium; and
    displaying a width of said first area of a particular dimension based on said myocardial wall movement factor for said selected myocardium section.

49. A computer implemented method for displaying information as described in claim 48 wherein said step of displaying a color representation of said myocardial perfusion ratio comprises the steps of:
    selecting a display color based on a magnitude of said perfusion ratio; and
    filling said first area on said display screen with said selected display color.

50. A computer implemented method for displaying information as described in claim 48 wherein said step of displaying a color representation of said myocardial perfusion ratio comprises the steps of:
    selecting a display color shade based on a magnitude of said perfusion ratio; and
    filling said first area on said display screen with said selected display color shade.

51. A computer implemented method for displaying information on a display screen used in diagnosing heart disease, said information obtained using gated SPECT imaging techniques and tomographic reconstruction procedures, said method comprising the computer implemented steps of:
    receiving a plurality of computed ratios representing myocardial perfusion for a selected region of myocardium;
    receiving a plurality of computed wall movement factors representing myocardial wall movement for said selected region of myocardium;
    rendering a functional ring on said display screen, said functional ring comprising a plurality of arc sections, said plurality of arc sections presenting representations of both said computed perfusion ratios and said computed wall movement factors of said selected region of said myocardium.

52. A computer implemented method for displaying information used in diagnosing heart disease as described in claim 51 wherein said step of rendering a functional ring comprises the steps of:
    displaying each of said plurality of arc sections with an individual color representation based on an individual perfusion ratio of said plurality of myocardial perfusion ratios; and
    displaying each of said plurality of arc sections with an individual arc section width based on an individual wall movement factor of said plurality of computed wall movement factors.

53. A computer implemented method for displaying information used in diagnosing heart disease as described in claim 52 wherein said step of displaying each of said arc sections with an individual color representation comprises the step of filling said each arc section with an individual color obtained from a color lookup table indexed by an individual perfusion ratio.

54. A computer implemented method for displaying information used in diagnosing heart disease as described in claim 52 wherein said step of displaying each of said plurality of arc sections with an individual width comprises the steps of:
    generating an arc section width toward a center of said functional display ring for positive wall movement factors; and generating an arc section width away from said center of said functional display ring for negative wall movement factors.

55. In a computer system including bus means for providing communication, a central processor means coupled to said bus means for processing instructions and commands, a display means coupled to said bus means for displaying information, a memory means coupled to said bus means for storing information, and an input means coupled to said bus means for user interface, a method for presenting information used for diagnosing heart disease, said method comprising the computer implemented steps of:

displaying a first image of a myocardial structure during diastolic phase of a cardiac cycle;

displaying a second image of said myocardial structure during systolic phase of said cardiac cycle;

selecting a region of interest of said first image and selecting a region of interest of said second image;

computing perfusion ratios and wall movement factors for individual sections of said myocardial structure defined by said regions of interest; and displaying a functional ring representative of said myocardial structure, said functional ring comprising representations of both said perfusion ratios and said wall movement factors of said individual sections of said myocardial structure.

56. A method for presenting information used for diagnosing heart disease as described in claim 55 wherein said first and second images of said myocardial structure are slices of tomographically reconstructed volumes of the heart at diastole and systole respectively.

57. A method for presenting information used for diagnosing heart disease as described in claim 55 wherein said steps of selecting said regions of interest comprise the step of:

using a cursor to position a center for a region of interest;

using said cursor to select a radial dimension of said region of interest from said center to encompass said myocardial structure; and repeating the above two steps to reconfigure a selected region of interest.

58. A method for presenting information used for diagnosing heart disease as described in claim 55 further comprising the step of dividing each of said region of interest of said first image and said region of interest of said second image into a plurality of individual sections and wherein a section pair comprises sections of each region of interest that correspond to a same portion of said myocardial structure.

59. A method for presenting information used for diagnosing heart disease as described in claim 58 wherein said step of computing perfusion ratios and wall movement factors comprises the step of:

computing a first average by averaging maximum intensity pixels within a first section of a section pair;

computing a second average by averaging maximum intensity pixels within a second section of said section pair; and computing a perfusion ratio for said section pair by dividing said first average by said second average.

60. A method for presenting information used for diagnosing heart disease as described in claim 58 wherein said step of computing perfusion ratios and wall movement factors comprises the steps of:

computing a first center of mass for a first section of a section pair;

computing a second center of mass for a second section of said section pair; and computing said wall motion factor based on the difference of radial distances between said first center of mass and said region of interest of said first image and said second center of mass and said region of interest of said second image.

61. A method for presenting information used for diagnosing heart disease as described in claim 58 wherein said step of displaying a functional ring representative of said myocardial structure comprises the steps of:

displaying a plurality of arc sections comprising said functional display ring, wherein each arc section corresponds to an individual section pair;

coloring each arc section depending on a perfusion ratio for said each arc section; and varying radial width of said each arc section depending on a wall movement factor for said each arc section.

62. In a computer system including bus means for providing communication, a central processor means coupled to said bus means for processing instructions and commands, a display means coupled to said bus means for displaying information, a memory means coupled to said bus means for storing information, and an input means coupled to said bus means for user interface, a method for presenting information used for diagnosing heart disease, said method comprising the computer implemented steps of:

configuring and storing a first set of reconstruction parameters used in tomographical reconstruction processing of raw image information, said first set of reconstruction Parameters defining: (a) slice thickness: and (b) reconstruction limits;

configuring and storing a second set of reconstruction Parameters used in tomographical reconstruction processing of raw image information, said second set of reconstruction parameters defining: (a) slice thickness: and (b) reconstruction limits, wherein said first and second set of reconstruction parameters are different;

acquiring said raw image information from a camera system using gated SPECT imaging techniques;

recalling said stored first set of reconstruction parameters;

reconstructing a first image volume based on said first set of reconstruction parameters and said raw image information;

displaying slices of said first image volume on said computer display means for different imaged segments of a cardiac cycle;

recalling said stored second set of reconstruction parameters:

reconstructing a second image volume based on said second set of reconstruction parameters and said raw image information: and displaying slices of said second image volume on said computer display means for different imaged segments of a cardiac cycle.

* * * * *